(12) United States Patent
Glimcher

(10) Patent No.: US 8,323,970 B2
(45) Date of Patent: Dec. 4, 2012

(54) MODULATION OF T CELL RECRUITMENT

(75) Inventor: Laurie H. Glimcher, West Newton, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 787 days.

(21) Appl. No.: 11/920,868

(22) PCT Filed: May 31, 2006

(86) PCT No.: PCT/US2006/020993
§ 371 (c)(1), (2), (4) Date: Jul. 10, 2009

(87) PCT Pub. No.: WO2006/130620
PCT Pub. Date: Dec. 7, 2006

(65) Prior Publication Data
US 2009/0298091 A1 Dec. 3, 2009

Related U.S. Application Data

(60) Provisional application No. 60/686,222, filed on May 31, 2005.

(51) Int. Cl.
C12N 5/00 (2006.01)
C12N 15/63 (2006.01)
G01N 33/53 (2006.01)
(52) U.S. Cl. ............................... 435/375; 435/455; 435/6
(58) Field of Classification Search .......................... None
See application file for complete search history.

(56) References Cited

U.S. PATENT DOCUMENTS

| 5,844,082 A | 12/1998 | Kishimoto et al. |
| 6,031,078 A | 2/2000 | Khodadoust |
| 6,037,148 A | 3/2000 | Khodadoust |
| 6,207,414 B1 | 3/2001 | Moore |
| 8,048,672 B2 * | 11/2011 | Glimcher et al. ............. 435/375 |
| 2002/0058034 A1 * | 5/2002 | Manjunath et al. ........ 424/144.1 |
| 2003/0186377 A1 | 10/2003 | Glimcher et al. |
| 2004/0001822 A1 * | 1/2004 | Levanon et al. ........... 424/130.1 |

FOREIGN PATENT DOCUMENTS

| WO | WO-99/11783 A2 | 3/1999 |
| WO | WO-00/73453 A1 | 12/2000 |
| WO | WO-03/048379 A1 | 6/2003 |

OTHER PUBLICATIONS

Aune, Thomas M. et al., "Inhibitors of Serotonin Synthesis and Antagonists of Serotonin 1A Receptors Inhibit T Lymphocyte Function in Vitro and Cell-Mediated Immunity In Vivo," The Journal of Immunology, vol. 153(2):489-498 (1994).
Barbulescu, Karina et al., "Cutting Edge: IL-12 and IL-18 Differentially Regulate the Transcriptional Activity of the Human IFN-g Promoter in Primary CD4+ T Lymphocytes," The Journal of Immunology, vol. 160:3642-3647 (1998).
Shoker, Ahmed S. et al., "Analysis of the in vitro effect of exogenous nitric oxide on human lymphocytes," Molecular and Cellular Biochemistry, vol. 171:75-83 (1997).
Yoshimoto, Tomohiro et al., "Interleukin 18 together with interleukin 12 inhibit IgE production by induction of interferon-g production from activated B cells," Proc. Natl. Acad. Sci. USA, vol. 94:3948-3953 (1997).
Ali, Majid et al., "Tyrosylprotein sulfotransferase-1 (TPST-1) does not regulate P-selectin-dependent rolling in vivo," The FASEB Journal, vol. 17(5):A796, Abstract No. 512.2 (2003).
Arakawa, S. et al., "Differential expression of mRNA for Th1 and Th2 cytokine-associated transcription factors and suppressors of cytokine signalling in peripheral blood mononuclear cells of patients with atopic dermatitis," Clin. Exp. Immunol., vol. 135:505-510 (2004).
Avni, Orly et al., "$T_H$ cell differentiation is accompanied by dynamic changes in histone acetylation of cytokine genes," Nature Immunology, vol. 3:643-651 (2002).
Bulfone, Alessandro et al., "*T-Brain*-1: A Homolog of Brachyury Whose Expression Defines Molecularly Distinct Domains within the Cerebral Cortex," Neuron, vol. 15:63-78 (1995).
Chen, Chang-Hung et al., "Transforming Growth Factor β Blocks Tec Kinase Phosphorylation, $Ca^{2+}$Influx, and NFATc Translocation Causing Inhibition of T Cell Differentiation," J. Exp. Med., vol. 197(12):1689-1699 (2003).
Ehrhardt, Carsten et al., "Selectins—an emerging target for drug delivery," Advanced Drug Delivery Reviews, vol. 56:527-549 (2004).
EMBL Accession No. AF093098, Zhang, W.X. et al., "Cloning and Characterization of a New Member of the T-Box Gene Family," Genomics, vol. 70(1):41-48 (2000).
Fargeas, Christine et al., "Differential effect of transforming growth factor β on the synthesis of $T_h1$- and $T_h2$-like lymphokines by human T lymphocytes," Eur. J. Immunol., vol. 22:2173-2176 (1992).
Finotto, Susetta et al., "Development of Spontaneous Airway Changes Consistent with Human Asthma in Mice Lacking T-bet," Science, vol. 295:336-338 (2002).
Geng, Jian-Guo et al., "P-selectin Cell Adhesion Molecule in Inflammation, Thrombosis, Cancer Growth and Metastasis," Current Medicinal Chemistry, vol. 11:2153-2160 (2004).
Glimcher, Laurie H. et al., "Transcription Factors in Lymphocyte Development—T and B Cells Get Together," Cell, vol. 96:13-23 (1999).
Hsieh, Chyi-Song et al., "Development of $T_H1$ CD4+ T Cells Through IL-12 Produced by *Listeria*-Induced Macrophages," Science, vol. 260:547-549 (1993).

(Continued)

Primary Examiner — Michail Belyavskyi
(74) Attorney, Agent, or Firm — Nelson Mullins Riley & Scarborough LLP; Debra J. Milasincic, Esq.

(57) ABSTRACT

The instant invention is based, at least in part, on the discovery that T-bet controls Th1 cell recruitment to sites of inflammation. This invention pertains to, inter alia, methods of identifying agents that modulate the effects of T-bet on the recruitment of T cells to sites of inflammation by modulating P-selectin-mediated T cell rolling and/or stable adherence of a T cell to a vascular endothelial cell, as well as methods of use therefore.

9 Claims, No Drawings

OTHER PUBLICATIONS

Hwang, Eun Sook et al., "IL-2 production in developing Th1 cells is regulated by heterodimerization of RelA and T-bet and requires T-bet serine residue 508," *JEM*, vol. 202(9):1289-1300 (2005).

Hwang, Eun Sook et al., "T Helper Cell Fate Specified by Kinase-Mediated Interaction of T-bet with GATA-3," *Science*, vol. 307:430-433 (2005).

Li, B. et al., "T-bet expression is upregulated in active Behçet's disease," *Br. J. Ophthalmol.*, vol. 87:1264-1267 (2003).

Lord, Graham M. et al., "T-bet is required for optimal proinflammatory CD4+ T-cell trafficking," *Blood*, vol. 106(10):3432-3439 (2005).

Lutters, Bianca C.H. et al., "Blocking endothelial adhesion molecules: a potential therapeutic strategy to combat atherogenesis," *Current Opinion in Lipidology*, vol. 15:545-552 (2004).

Macatonia, Steven E. et al., "Dendritic cells and macrophages are required for Th1 development of CD4+ T cells from αβ TCR transgenic mice: IL-12 substitution for macrophages to stimulate IFN-γ production is IFN-γ-dependent," *International Immunology*, vol. 5(9):1119-1128 (1993).

Maggi, Enrico et al., "Reciprocal Regulatory Effects of IFN-γ and IL-4 on the In Vitro Development of Human Th1 and Th2 Clones," *The Journal of Immunology*, vol. 148(7):2142-2147 (1992).

Manetti, Roberto et al., "Natural Killer Cell Stimulatory Factor (Interleukin 12 [IL-12]) Induces T Helper Type 1 (Th1)-specific Immune Responses and Inhibits the Development of IL-4-producing Th Cells," *J. Exp. Med.*, vol. 177:1199-1204 (1993).

Miller, Andrew T. et al., "Signaling through Itk Promotes T Helper 2 Differentiation via Negative Regulation of T-bet," *Immunity*, vol. 21:67-80 (2004).

Mullen, Alan C. et al., "Role of T-bet in Commitment of $T_H1$ Cells Before IL-12-Dependent Selection," *Science*, vol. 292:1907-1910 (2001).

Neurath, M.F. et al., "The Transcription Factor T-bet Regulates Mucosal T Cell Activation in Experimental Colitis and Crohn's Disease," *J. Exp. Med.*, vol. 195(9):1129-1143 (2002).

O'Garra, Anne, "Cytokines Induce the Development of Functionally Heterogeneous T Helper Cell Subsets," *Immunity*, vol. 8:275-283 (1998).

Owaki, Toshiyuki et al., "IL-27 Induces Th1 Differentiation via p38 MAPK/T-bet- and Intercellular Adhesion Molecule-1/LFA-1/ERK1/2-Dependent Pathways," *The Journal of Immunology*, vol. 177:7579-7587 (2006).

Parronchi, Paola et al., "IL-4 and IFN (α and γ) Exert Opposite Regulatory Effects on the Development of Cytolytic Potential by Th1 or Th2 Human T Cell Clones," *The Journal of Immunity*, vol. 149(9):2977-2983 (1992).

Paul, William E. et al., "Lymphocyte Responses and Cytokines," *Cell*, vol. 76:241-251 (1994).

Peng, Stanford L. et al., "T-bet regulates IgG class switching and pathogenic autoantibody production," *PNAS*, vol. 99(8):5545-5550 (2002).

Powrie, Fiona et al., "Cytokine regulation of T-cell function: potential for therapeutic intervention," *Immunology Today*, vol. 14(6):270-274 (1993).

Rao, R.M. et al., "The transcription T-bet is required for optimal proinflammatory trafficking of CD4+ T cells," *Arthritis Research & Therapy*, vol. 7(Suppl. 1):S6-S7, Abstract No. P5 (2005).

Scott, Phillip, "IFN-γ Modulates the Early Development of Th1 and Th2 Responses in a Murine Model of Cutaneous Leishmaniasis," *The Journal of Immunology*, vol. 147(9):3149-3155 (1991).

Seder, Robert A. et al., "Acquisition of Lymphokine-Producing Phenotype by CD4+ T Cells," *Annu. Rev. Immunol.*, vol. 12:635-673 (1994).

Seder, Robert A. et al., "Interleukin 12 acts directly on CD4+ T cells to enhance priming for interferon γ production and diminishes interleukin 4 inhibition of such priming," *Proc. Natl. Acad. Sci. USA*, vol. 90:10188-10192 (1993).

Smith, Jim, "T-box genes, what they do and how they do it," *TIG*, vol. 15(4):154-158 (1999).

Snapp, Karen R. et al., "A Novel P-Selectin Glycoprotein Ligand-1 Monoclonal Antibody Recognizes an Epitope Within the Tyrosine Sulfate Motif of Human PSGL-1 and Blocks Recognition of Both P- and L-Selectin," *Blood*, vol. 91(1):154-164 (1998).

Szabo, Susanne J. et al., "A Novel Transcription Factor, T-bet, Directs Th1 Lineage Commitment," *Cell*, vol. 100:655-669 (2000).

Szabo, Susanne J. et al., "Distinct Effects of T-bet in $T_H1$ Lineage Commitment and IFN-γ Production in CD4 and CD8 T Cells," *Science*, vol. 295:338-342 (2002).

Szabo, Susanne J. et al., "Genes that regulate interleukin-4 expression in T cells," *Current Opinion in Immunology*, vol. 9:776-781 (1997).

Szabo, Susanne J. et al., "Molecular Mechanisms Regulating Th1 Immune Responses," *Annu. Rev. Immunol.*, vol. 21:713-758 (2003).

Thomas, Clare E. et al., "Progress and Problems with the Use of Viral Vectors for Gene Therapy," *Nature*, vol. 4:346-358 (2003).

Trinchieri, Giorgio, "Interleukin-12 and its role in the generation of $T_H1$ cells," *Immunology Today*, vol. 14(7):335-338 (1993).

Webster's New World Dictionary of American English, Third College Edition, "Prosthetic," Webster's New World, New York, Victoria Neufeldt et al., Ed., p. 1080 (1988).

Wu, Chang-You et al., "IL-12 Induces the Production of IFN-γ by Neonatal Human CD4 T Cells," *The Journal of Immunology*, vol. 151(4):1938-1949 (1993).

Yin, Zhinan et al., "T-Bet Expression and Failure of GATA-3 Cross-Regulation Lead to Default Producton in IFN-γ by γδ T Cells," *The Journal of Immunology*, vol. 168:1566-1571 (2002).

Zheng, Wei-ping et al., "The Transcription Factor GATA-3 Is Necessary and Sufficient for Th2 Cytokine Gene Expression in CD4 T Cells," *Cell*, vol. 89:587-596 (1997).

Zhang, Wen-xiang et al., "Cloning and Characterization of a New Member of the T-Box Gene Family," *Genomics*, vol. 70:41-48 (2000).

International Search Report for Application No. PCT/US06/02917, dated Jan. 11, 2007.

Waffler, Sigrid et al., "A Combined Analysis of Genomic and Primary Protein Structure Defines the Phylogenetic Relationship of New Members of the T-Box Family," *Genomics*, vol. 48:24-33 (1998).

Japanese Office Action for Application No. 2009-200540, dated Dec. 8, 2009.

\* cited by examiner

SEQUENCE LISTING

<160> NUMBER OF SEQ ID NOS: 41

<210> SEQ ID NO 1
<211> LENGTH: 1608
<212> TYPE: DNA
<213> ORGANISM: Homo sapiens
<220> FEATURE:
<221> NAME/KEY: CDS
<222> LOCATION: (1)..(1605)

<400> SEQUENCE: 1

| | | | | | | | | | | | | | | | | |
|---|---|---|---|---|---|---|---|---|---|---|---|---|---|---|---|---|
| atg | ggc | atc | gtg | gag | ccg | ggt | tgc | gga | gac | atg | ctg | acg | ggc | acc | gag | 48 |
| Met | Gly | Ile | Val | Glu | Pro | Gly | Cys | Gly | Asp | Met | Leu | Thr | Gly | Thr | Glu | |
| 1 | | | | 5 | | | | | 10 | | | | | 15 | | |
| ccg | atg | ccg | ggg | agc | gac | gag | ggc | cgg | gcg | cct | ggc | gcc | gac | ccg | cag | 96 |
| Pro | Met | Pro | Gly | Ser | Asp | Glu | Gly | Arg | Ala | Pro | Gly | Ala | Asp | Pro | Gln | |
| | | | 20 | | | | | 25 | | | | | 30 | | | |
| cac | cgc | tac | ttc | tac | ccg | gag | ccg | ggc | gcg | cag | gac | gcg | gac | gag | cgt | 144 |
| His | Arg | Tyr | Phe | Tyr | Pro | Glu | Pro | Gly | Ala | Gln | Asp | Ala | Asp | Glu | Arg | |
| | | | | 35 | | | | | 40 | | | | | 45 | | |
| cgc | ggg | ggc | ggc | agc | ctg | ggg | tct | ccc | tac | ccg | ggg | ggc | gcc | ttg | gtg | 192 |
| Arg | Gly | Gly | Gly | Ser | Leu | Gly | Ser | Pro | Tyr | Pro | Gly | Gly | Ala | Leu | Val | |
| 50 | | | | | 55 | | | | | 60 | | | | | | |
| ccc | gcc | ccg | ccg | agc | cgc | ttc | ctt | gga | gcc | tac | gcc | tac | ccg | ccg | cga | 240 |
| Pro | Ala | Pro | Pro | Ser | Arg | Phe | Leu | Gly | Ala | Tyr | Ala | Tyr | Pro | Pro | Arg | |
| 65 | | | | | 70 | | | | | 75 | | | | | 80 | |
| ccc | cag | gcg | gcc | ggc | ttc | ccc | ggc | gcg | ggc | gag | tcc | ttc | ccg | ccg | ccc | 288 |
| Pro | Gln | Ala | Ala | Gly | Phe | Pro | Gly | Ala | Gly | Glu | Ser | Phe | Pro | Pro | Pro | |
| | | | | 85 | | | | | 90 | | | | | 95 | | |
| gcg | gac | gcc | gag | ggc | tac | cag | ccg | ggc | gag | ggc | tac | gcc | gcc | ccg | gac | 336 |
| Ala | Asp | Ala | Glu | Gly | Tyr | Gln | Pro | Gly | Glu | Gly | Tyr | Ala | Ala | Pro | Asp | |
| | | | 100 | | | | | 105 | | | | | 110 | | | |
| ccg | cgc | gcc | ggg | ctc | tac | ccg | ggg | ccg | cgt | gag | gac | tac | gcg | cta | ccc | 384 |
| Pro | Arg | Ala | Gly | Leu | Tyr | Pro | Gly | Pro | Arg | Glu | Asp | Tyr | Ala | Leu | Pro | |
| | | | | 115 | | | | | 120 | | | | | 125 | | |
| gcg | gga | ctg | gag | gtg | tcg | ggg | aaa | ctg | agg | gtc | gcg | ctc | aac | aac | cac | 432 |
| Ala | Gly | Leu | Glu | Val | Ser | Gly | Lys | Leu | Arg | Val | Ala | Leu | Asn | Asn | His | |
| 130 | | | | | 135 | | | | | 140 | | | | | | |
| ctg | ttg | tgg | tcc | aag | ttt | aat | cag | cac | cag | aca | gag | atg | atc | atc | acc | 480 |
| Leu | Leu | Trp | Ser | Lys | Phe | Asn | Gln | His | Gln | Thr | Glu | Met | Ile | Ile | Thr | |
| 145 | | | | | 150 | | | | | 155 | | | | | 160 | |
| aag | cag | gga | cgg | cgg | atg | ttc | cca | ttc | ctg | tca | ttt | act | gtg | gcc | ggg | 528 |
| Lys | Gln | Gly | Arg | Arg | Met | Phe | Pro | Phe | Leu | Ser | Phe | Thr | Val | Ala | Gly | |
| | | | | 165 | | | | | 170 | | | | | 175 | | |
| ctg | gag | ccc | acc | agc | cac | tac | agg | atg | ttt | gtg | gac | gtg | gtc | ttg | gtg | 576 |
| Leu | Glu | Pro | Thr | Ser | His | Tyr | Arg | Met | Phe | Val | Asp | Val | Val | Leu | Val | |
| | | | 180 | | | | | 185 | | | | | 190 | | | |
| gac | cag | cac | cac | tgg | cgg | tac | cag | agc | ggc | aag | tgg | gtg | cag | tgt | gga | 624 |
| Asp | Gln | His | His | Trp | Arg | Tyr | Gln | Ser | Gly | Lys | Trp | Val | Gln | Cys | Gly | |
| | | | | 195 | | | | | 200 | | | | | 205 | | |
| aag | gcc | gag | ggc | agc | atg | cca | gga | aac | cgc | ctg | tac | gtc | cac | ccg | gac | 672 |
| Lys | Ala | Glu | Gly | Ser | Met | Pro | Gly | Asn | Arg | Leu | Tyr | Val | His | Pro | Asp | |
| | | | 210 | | | | | 215 | | | | | 220 | | | |
| tcc | ccc | aac | aca | gga | gcg | cac | tgg | atg | cgc | cag | gaa | gtt | tca | ttt | ggg | 720 |
| Ser | Pro | Asn | Thr | Gly | Ala | His | Trp | Met | Arg | Gln | Glu | Val | Ser | Phe | Gly | |
| 225 | | | | | 230 | | | | | 235 | | | | | 240 | |
| aaa | cta | aag | ctc | aca | aac | aac | aag | ggg | gcg | tcc | aac | aat | gtg | acc | cag | 768 |
| Lys | Leu | Lys | Leu | Thr | Asn | Asn | Lys | Gly | Ala | Ser | Asn | Asn | Val | Thr | Gln | |
| | | | | 245 | | | | | 250 | | | | | 255 | | |

```
atg att gtg ctc cag tcc ctc cat aag tac cag ccc cgg ctg cat atc      816
Met Ile Val Leu Gln Ser Leu His Lys Tyr Gln Pro Arg Leu His Ile
        260                 265                 270 gtt gag gtg aac gac gga gag cca gag gca gcc tgc aac gct tcc aac      864
Val Glu Val Asn Asp Gly Glu Pro Glu Ala Ala Cys Asn Ala Ser Asn
    275                 280                 285 acg cat atc ttt act ttc caa gaa acc cag ttc att gcc gtg act gcc      912
Thr His Ile Phe Thr Phe Gln Glu Thr Gln Phe Ile Ala Val Thr Ala
290                 295                 300 tac cag aat gcc gag att act cag ctg aaa att gat aat aac ccc ttt      960
Tyr Gln Asn Ala Glu Ile Thr Gln Leu Lys Ile Asp Asn Asn Pro Phe
305                 310                 315                 320 gcc aaa gga ttc cgg gag aac ttt gag tcc atg tac aca tct gtt gac     1008
Ala Lys Gly Phe Arg Glu Asn Phe Glu Ser Met Tyr Thr Ser Val Asp
                325                 330                 335 acc agc atc ccc tcc ccg cct gga ccc aac tgt caa ttc ctt ggg gga     1056
Thr Ser Ile Pro Ser Pro Pro Gly Pro Asn Cys Gln Phe Leu Gly Gly
            340                 345                 350 gat cac tac tct cct ctc cta ccc aac cag tat cct gtt ccc agc cgc     1104
Asp His Tyr Ser Pro Leu Leu Pro Asn Gln Tyr Pro Val Pro Ser Arg
        355                 360                 365 ttc tac ccc gac ctt cct ggc cag gcg aag gat gtg gtt ccc cag gct     1152
Phe Tyr Pro Asp Leu Pro Gly Gln Ala Lys Asp Val Val Pro Gln Ala
370                 375                 380 tac tgg ctg ggg gcc ccc cgg gac cac agc tat gag gct gag ttt cga     1200
Tyr Trp Leu Gly Ala Pro Arg Asp His Ser Tyr Glu Ala Glu Phe Arg
385                 390                 395                 400 gca gtc agc atg aag cct gca ttc ttg ccc tct gcc cct ggg ccc acc     1248
Ala Val Ser Met Lys Pro Ala Phe Leu Pro Ser Ala Pro Gly Pro Thr
                405                 410                 415 atg tcc tac tac cga ggc cag gag gtc ctg gca cct gga gct ggc tgg     1296
Met Ser Tyr Tyr Arg Gly Gln Glu Val Leu Ala Pro Gly Ala Gly Trp
            420                 425                 430 cct gtg gca ccc cag tac cct ccc aag atg ggc ccg gcc agc tgg ttc     1344
Pro Val Ala Pro Gln Tyr Pro Pro Lys Met Gly Pro Ala Ser Trp Phe
        435                 440                 445 cgc cct atg cgg act ctg ccc atg gaa ccc ggc cct gga ggc tca gag     1392
Arg Pro Met Arg Thr Leu Pro Met Glu Pro Gly Pro Gly Gly Ser Glu
450                 455                 460 gga cgg gga cca gag gac cag ggt ccc ccc ttg gtg tgg act gag att     1440
Gly Arg Gly Pro Glu Asp Gln Gly Pro Pro Leu Val Trp Thr Glu Ile
465                 470                 475                 480 gcc ccc atc cgg ccg gaa tcc agt gat tca gga ctg ggc gaa gga gac     1488
Ala Pro Ile Arg Pro Glu Ser Ser Asp Ser Gly Leu Gly Glu Gly Asp
                485                 490                 495 tct aag agg agg cgc gtg tcc ccc tat cct tcc agt ggt gac agc tcc     1536
Ser Lys Arg Arg Arg Val Ser Pro Tyr Pro Ser Ser Gly Asp Ser Ser
            500                 505                 510 tcc cct gct ggg gcc cct tct cct ttt gat aag gaa gct gaa gga cag     1584
Ser Pro Ala Gly Ala Pro Ser Pro Phe Asp Lys Glu Ala Glu Gly Gln
        515                 520                 525 ttt tat aac tat ttt ccc aac tga                                     1608
Phe Tyr Asn Tyr Phe Pro Asn
530                 535

<210> SEQ ID NO 2
<211> LENGTH: 535
<212> TYPE: PRT
<213> ORGANISM: Homo sapiens
```

-continued

<400> SEQUENCE: 2

```
Met Gly Ile Val Glu Pro Gly Cys Gly Asp Met Leu Thr Gly Thr Glu
1               5                   10                  15

Pro Met Pro Gly Ser Asp Glu Gly Arg Ala Pro Gly Ala Asp Pro Gln
            20                  25                  30

His Arg Tyr Phe Tyr Pro Glu Pro Gly Ala Gln Asp Ala Asp Glu Arg
        35                  40                  45

Arg Gly Gly Gly Ser Leu Gly Ser Pro Tyr Pro Gly Gly Ala Leu Val
    50                  55                  60

Pro Ala Pro Pro Ser Arg Phe Leu Gly Ala Tyr Ala Tyr Pro Pro Arg
65                  70                  75                  80

Pro Gln Ala Ala Gly Phe Pro Gly Ala Gly Glu Ser Phe Pro Pro Pro
                85                  90                  95

Ala Asp Ala Glu Gly Tyr Gln Pro Gly Glu Gly Tyr Ala Ala Pro Asp
            100                 105                 110

Pro Arg Ala Gly Leu Tyr Pro Gly Pro Arg Glu Asp Tyr Ala Leu Pro
        115                 120                 125

Ala Gly Leu Glu Val Ser Gly Lys Leu Arg Val Ala Leu Asn Asn His
    130                 135                 140

Leu Leu Trp Ser Lys Phe Asn Gln His Gln Thr Glu Met Ile Ile Thr
145                 150                 155                 160

Lys Gln Gly Arg Arg Met Phe Pro Phe Leu Ser Phe Thr Val Ala Gly
                165                 170                 175

Leu Glu Pro Thr Ser His Tyr Arg Met Phe Val Asp Val Val Leu Val
            180                 185                 190

Asp Gln His His Trp Arg Tyr Gln Ser Gly Lys Trp Val Gln Cys Gly
        195                 200                 205

Lys Ala Glu Gly Ser Met Pro Gly Asn Arg Leu Tyr Val His Pro Asp
    210                 215                 220

Ser Pro Asn Thr Gly Ala His Trp Met Arg Gln Glu Val Ser Phe Gly
225                 230                 235                 240

Lys Leu Lys Leu Thr Asn Asn Lys Gly Ala Ser Asn Asn Val Thr Gln
                245                 250                 255

Met Ile Val Leu Gln Ser Leu His Lys Tyr Gln Pro Arg Leu His Ile
            260                 265                 270

Val Glu Val Asn Asp Gly Glu Pro Glu Ala Ala Cys Asn Ala Ser Asn
        275                 280                 285

Thr His Ile Phe Thr Phe Gln Glu Thr Gln Phe Ile Ala Val Thr Ala
    290                 295                 300

Tyr Gln Asn Ala Glu Ile Thr Gln Leu Lys Ile Asp Asn Asn Pro Phe
305                 310                 315                 320

Ala Lys Gly Phe Arg Glu Asn Phe Glu Ser Met Tyr Thr Ser Val Asp
                325                 330                 335

Thr Ser Ile Pro Ser Pro Pro Gly Pro Asn Cys Gln Phe Leu Gly Gly
            340                 345                 350

Asp His Tyr Ser Pro Leu Leu Pro Asn Gln Tyr Pro Val Pro Ser Arg
        355                 360                 365

Phe Tyr Pro Asp Leu Pro Gly Gln Ala Lys Asp Val Val Pro Gln Ala
    370                 375                 380

Tyr Trp Leu Gly Ala Pro Arg Asp His Ser Tyr Glu Ala Glu Phe Arg
385                 390                 395                 400

Ala Val Ser Met Lys Pro Ala Phe Leu Pro Ser Ala Pro Gly Pro Thr
                405                 410                 415
```

```
Met Ser Tyr Tyr Arg Gly Gln Glu Val Leu Ala Pro Gly Ala Gly Trp
            420                 425                 430

Pro Val Ala Pro Gln Tyr Pro Lys Met Gly Pro Ala Ser Trp Phe
                435                 440                 445

Arg Pro Met Arg Thr Leu Pro Met Glu Pro Gly Pro Gly Gly Ser Glu
    450                 455                 460

Gly Arg Gly Pro Glu Asp Gln Gly Pro Pro Leu Val Trp Thr Glu Ile
465                 470                 475                 480

Ala Pro Ile Arg Pro Glu Ser Ser Asp Ser Gly Leu Gly Glu Gly Asp
                485                 490                 495

Ser Lys Arg Arg Val Ser Pro Tyr Pro Ser Ser Gly Asp Ser Ser
                500                 505                 510

Ser Pro Ala Gly Ala Pro Ser Pro Phe Asp Lys Glu Ala Glu Gly Gln
            515                 520                 525

Phe Tyr Asn Tyr Phe Pro Asn
            530                 535

<210> SEQ ID NO 3
<211> LENGTH: 1593
<212> TYPE: DNA
<213> ORGANISM: Mus musculus
<220> FEATURE:
<221> NAME/KEY: CDS
<222> LOCATION: (1)..(1590)

<400> SEQUENCE: 3
```

| | | | | | | | | | | | | | | | | |
|---|---|---|---|---|---|---|---|---|---|---|---|---|---|---|---|---|
| atg | ggc | atc | gtg | gag | ccg | ggc | tgc | gga | gac | atg | ctg | acc | ggc | acc | gag | 48 |
| Met | Gly | Ile | Val | Glu | Pro | Gly | Cys | Gly | Asp | Met | Leu | Thr | Gly | Thr | Glu | |
| 1 | | | | 5 | | | | | 10 | | | | | 15 | | |
| ccg | atg | ccg | agt | gac | gag | ggc | cgg | ggg | ccc | gga | gcg | gac | caa | cag | cat | 96 |
| Pro | Met | Pro | Ser | Asp | Glu | Gly | Arg | Gly | Pro | Gly | Ala | Asp | Gln | Gln | His | |
| | | 20 | | | | | 25 | | | | | 30 | | | | |
| cgt | ttc | ttc | tat | ccc | gag | ccg | ggc | gca | cag | gac | ccg | acc | gat | cgc | cgc | 144 |
| Arg | Phe | Phe | Tyr | Pro | Glu | Pro | Gly | Ala | Gln | Asp | Pro | Thr | Asp | Arg | Arg | |
| | 35 | | | | | 40 | | | | | 45 | | | | | |
| gca | ggt | agc | agc | ctg | ggg | acg | ccc | tac | tct | ggg | ggc | gcc | ctg | gtg | cct | 192 |
| Ala | Gly | Ser | Ser | Leu | Gly | Thr | Pro | Tyr | Ser | Gly | Gly | Ala | Leu | Val | Pro | |
| 50 | | | | | 55 | | | | | 60 | | | | | | |
| gcc | gcg | ccg | ggt | cgc | ttc | ctt | gga | tcc | ttc | gcc | tac | ccg | ccc | cgg | gct | 240 |
| Ala | Ala | Pro | Gly | Arg | Phe | Leu | Gly | Ser | Phe | Ala | Tyr | Pro | Pro | Arg | Ala | |
| 65 | | | | 70 | | | | | 75 | | | | | 80 | | |
| cag | gtg | gct | ggc | ttt | ccc | ggg | cct | ggc | gag | ttc | ttc | ccg | ccg | ccc | gcg | 288 |
| Gln | Val | Ala | Gly | Phe | Pro | Gly | Pro | Gly | Glu | Phe | Phe | Pro | Pro | Pro | Ala | |
| | | | 85 | | | | | 90 | | | | | 95 | | | |
| ggt | gcg | gag | ggc | tac | ccg | ccc | gtg | gat | ggc | tac | cct | gcc | cct | gac | ccg | 336 |
| Gly | Ala | Glu | Gly | Tyr | Pro | Pro | Val | Asp | Gly | Tyr | Pro | Ala | Pro | Asp | Pro | |
| | | 100 | | | | | 105 | | | | | 110 | | | | |
| cgc | gcg | ggg | ctc | tac | cca | ggg | ccg | cgc | gag | gac | tac | gca | ttg | ccc | gcg | 384 |
| Arg | Ala | Gly | Leu | Tyr | Pro | Gly | Pro | Arg | Glu | Asp | Tyr | Ala | Leu | Pro | Ala | |
| | 115 | | | | | 120 | | | | | 125 | | | | | |
| ggg | ttg | gag | gtg | tct | ggg | aag | ctg | aga | gtc | gcg | ctc | agc | aac | cac | ctg | 432 |
| Gly | Leu | Glu | Val | Ser | Gly | Lys | Leu | Arg | Val | Ala | Leu | Ser | Asn | His | Leu | |
| 130 | | | | | 135 | | | | | 140 | | | | | | |
| ttg | tgg | tcc | aag | ttc | aac | cag | cac | cag | aca | gag | atg | atc | atc | act | aag | 480 |
| Leu | Trp | Ser | Lys | Phe | Asn | Gln | His | Gln | Thr | Glu | Met | Ile | Ile | Thr | Lys | |
| 145 | | | | 150 | | | | | 155 | | | | | 160 | | |
| caa | gga | cgg | cga | atg | ttc | cca | ttc | ctg | tcc | ttc | acc | gtg | gcc | ggg | ctg | 528 |
| Gln | Gly | Arg | Arg | Met | Phe | Pro | Phe | Leu | Ser | Phe | Thr | Val | Ala | Gly | Leu | |
| | | | 165 | | | | | 170 | | | | | 175 | | | |
| gag | ccc | aca | agc | cat | tac | agg | atg | ttt | gtg | gat | gtg | gtc | ttg | gtg | gac | 576 |

```
                                                              -continued

Glu Pro Thr Ser His Tyr Arg Met Phe Val Asp Val Leu Val Asp
            180                 185                 190 cag cac cac tgg cgg tac cag agc ggc aag tgg gtg cag tgt gga aag       624
Gln His His Trp Arg Tyr Gln Ser Gly Lys Trp Val Gln Cys Gly Lys
            195                 200                 205 gca gaa ggc agc atg cca ggg aac cgc tta tat gtc cac cca gac tcc       672
Ala Glu Gly Ser Met Pro Gly Asn Arg Leu Tyr Val His Pro Asp Ser
            210                 215                 220 ccc aac acc gga gcc cac tgg atg cgc cag gaa gtt tca ttt ggg aag       720
Pro Asn Thr Gly Ala His Trp Met Arg Gln Glu Val Ser Phe Gly Lys
225                 230                 235                 240 cta aag ctc acc aac aac aag ggg gct tcc aac aat gtg acc cag atg       768
Leu Lys Leu Thr Asn Asn Lys Gly Ala Ser Asn Asn Val Thr Gln Met
                245                 250                 255 atc gtc ctg cag tct ctc cac aag tac cag ccc cgg ctg cac atc gtg       816
Ile Val Leu Gln Ser Leu His Lys Tyr Gln Pro Arg Leu His Ile Val
                260                 265                 270 gag gtg aat gat gga gag cca gag gct gcc tgc agt gct tct aac aca       864
Glu Val Asn Asp Gly Glu Pro Glu Ala Ala Cys Ser Ala Ser Asn Thr
                275                 280                 285 cac gtc ttt act ttc caa gag acc cag ttc att gca gtg act gcc tac       912
His Val Phe Thr Phe Gln Glu Thr Gln Phe Ile Ala Val Thr Ala Tyr
            290                 295                 300 cag aac gca gag atc act cag ctg aaa atc gac aac aac ccc ttt gcc       960
Gln Asn Ala Glu Ile Thr Gln Leu Lys Ile Asp Asn Asn Pro Phe Ala
305                 310                 315                 320 aaa gga ttc cgg gag aac ttt gag tcc atg tac gca tct gtt gat acg      1008
Lys Gly Phe Arg Glu Asn Phe Glu Ser Met Tyr Ala Ser Val Asp Thr
                325                 330                 335 agt gtc ccc tcg cca cct gga ccc aac tgt caa ctg ctt ggg gga gac      1056
Ser Val Pro Ser Pro Pro Gly Pro Asn Cys Gln Leu Leu Gly Gly Asp
                340                 345                 350 ccc ttc tca cct ctt cta tcc aac cag tat cct gtt ccc agc cgt ttc      1104
Pro Phe Ser Pro Leu Leu Ser Asn Gln Tyr Pro Val Pro Ser Arg Phe
            355                 360                 365 tac ccc gac ctt cca ggc cag ccc aag gat atg atc tca cag cct tac      1152
Tyr Pro Asp Leu Pro Gly Gln Pro Lys Asp Met Ile Ser Gln Pro Tyr
    370                 375                 380 tgg ctg ggg aca cct cgg gaa cac agt tat gaa gcg gag ttc cga gct      1200
Trp Leu Gly Thr Pro Arg Glu His Ser Tyr Glu Ala Glu Phe Arg Ala
385                 390                 395                 400 gtg agc atg aag ccc aca ctc cta ccc tct gcc ccg ggg ccc act gtg      1248
Val Ser Met Lys Pro Thr Leu Leu Pro Ser Ala Pro Gly Pro Thr Val
                405                 410                 415 ccc tac tac cgg ggc caa gac gtc ctg gcg cct gga gct ggt tgg ccc      1296
Pro Tyr Tyr Arg Gly Gln Asp Val Leu Ala Pro Gly Ala Gly Trp Pro
            420                 425                 430 gtg gcc cct caa tac ccg ccc aag atg agc cca gct ggc tgg ttc cgg      1344
Val Ala Pro Gln Tyr Pro Pro Lys Met Ser Pro Ala Gly Trp Phe Arg
            435                 440                 445 ccc atg cga act ctg ccc atg gac ccg ggc ctg gga tcc tca gag gaa      1392
Pro Met Arg Thr Leu Pro Met Asp Pro Gly Leu Gly Ser Ser Glu Glu
    450                 455                 460 cag ggc tcc tcc ccc tcg ctg tgg cct gag gtc acc tcc ctc cag ccg      1440
Gln Gly Ser Ser Pro Ser Leu Trp Pro Glu Val Thr Ser Leu Gln Pro
465                 470                 475                 480 gag ccc agc gac tca gga cta ggc gaa gga gac act aag agg agg agg      1488
Glu Pro Ser Asp Ser Gly Leu Gly Glu Gly Asp Thr Lys Arg Arg Arg
                485                 490                 495 ata tcc ccc tat cct tcc agt ggc gac agc tcc tct ccc gct ggg gcc      1536
```

```
                                 -continued

Ile Ser Pro Tyr Pro Ser Ser Gly Asp Ser Ser Pro Ala Gly Ala
            500                 505                 510 cct tct cct ttt gat aag gaa acc gaa ggc cag ttt tat aat tat ttt        1584
Pro Ser Pro Phe Asp Lys Glu Thr Glu Gly Gln Phe Tyr Asn Tyr Phe
            515                 520                 525 ccc aac tga                                                             1593
Pro Asn
530

<210> SEQ ID NO 4
<211> LENGTH: 530
<212> TYPE: PRT
<213> ORGANISM: Mus musculus

<400> SEQUENCE: 4

Met Gly Ile Val Glu Pro Gly Cys Gly Asp Met Leu Thr Gly Thr Glu
1               5                   10                  15

Pro Met Pro Ser Asp Glu Gly Arg Gly Pro Ala Asp Gln Gln His
            20                  25                  30

Arg Phe Phe Tyr Pro Glu Pro Gly Ala Gln Asp Pro Thr Asp Arg Arg
            35                  40                  45

Ala Gly Ser Ser Leu Gly Thr Pro Tyr Ser Gly Gly Ala Leu Val Pro
50                      55                  60

Ala Ala Pro Gly Arg Phe Leu Gly Ser Phe Ala Tyr Pro Pro Arg Ala
65                  70                  75                  80

Gln Val Ala Gly Phe Pro Gly Pro Gly Glu Phe Phe Pro Pro Pro Ala
                85                  90                  95

Gly Ala Glu Gly Tyr Pro Pro Val Asp Gly Tyr Pro Ala Pro Asp Pro
            100                 105                 110

Arg Ala Gly Leu Tyr Pro Gly Pro Arg Glu Asp Tyr Ala Leu Pro Ala
            115                 120                 125

Gly Leu Glu Val Ser Gly Lys Leu Arg Val Ala Leu Ser Asn His Leu
130                 135                 140

Leu Trp Ser Lys Phe Asn Gln His Gln Thr Glu Met Ile Ile Thr Lys
145                 150                 155                 160

Gln Gly Arg Arg Met Phe Pro Phe Leu Ser Phe Thr Val Ala Gly Leu
                165                 170                 175

Glu Pro Thr Ser His Tyr Arg Met Phe Val Asp Val Val Leu Val Asp
            180                 185                 190

Gln His His Trp Arg Tyr Gln Ser Gly Lys Trp Val Gln Cys Gly Lys
            195                 200                 205

Ala Glu Gly Ser Met Pro Gly Asn Arg Leu Tyr Val His Pro Asp Ser
210                 215                 220

Pro Asn Thr Gly Ala His Trp Met Arg Gln Glu Val Ser Phe Gly Lys
225                 230                 235                 240

Leu Lys Leu Thr Asn Asn Lys Gly Ala Ser Asn Asn Val Thr Gln Met
                245                 250                 255

Ile Val Leu Gln Ser Leu His Lys Tyr Gln Pro Arg Leu His Ile Val
            260                 265                 270

Glu Val Asn Asp Gly Glu Pro Glu Ala Ala Cys Ser Ala Ser Asn Thr
            275                 280                 285

His Val Phe Thr Phe Gln Glu Thr Gln Phe Ile Ala Val Thr Ala Tyr
290                 295                 300

Gln Asn Ala Glu Ile Thr Gln Leu Lys Ile Asp Asn Asn Pro Phe Ala
305                 310                 315                 320

Lys Gly Phe Arg Glu Asn Phe Glu Ser Met Tyr Ala Ser Val Asp Thr
```

|   |   |   | 325 |   |   |   | 330 |   |   |   | 335 |
|---|---|---|---|---|---|---|---|---|---|---|---|

Ser Val Pro Ser Pro Gly Pro Asn Cys Gln Leu Leu Gly Gly Asp
                        340                      345                      350

Pro Phe Ser Pro Leu Leu Ser Asn Gln Tyr Pro Val Pro Ser Arg Phe
            355                      360                      365

Tyr Pro Asp Leu Pro Gly Gln Pro Lys Asp Met Ile Ser Gln Pro Tyr
    370                      375                      380

Trp Leu Gly Thr Pro Arg Glu His Ser Tyr Glu Ala Glu Phe Arg Ala
385                      390                      395                      400

Val Ser Met Lys Pro Thr Leu Leu Pro Ser Ala Pro Gly Pro Thr Val
                405                      410                      415

Pro Tyr Tyr Arg Gly Gln Asp Val Leu Ala Pro Gly Ala Gly Trp Pro
        420                      425                      430

Val Ala Pro Gln Tyr Pro Pro Lys Met Ser Pro Ala Gly Trp Phe Arg
            435                      440                      445

Pro Met Arg Thr Leu Pro Met Asp Pro Gly Leu Gly Ser Ser Glu Glu
    450                      455                      460

Gln Gly Ser Ser Pro Ser Leu Trp Pro Glu Val Thr Ser Leu Gln Pro
465                      470                      475                      480

Glu Pro Ser Asp Ser Gly Leu Gly Glu Gly Asp Thr Lys Arg Arg Arg
                485                      490                      495

Ile Ser Pro Tyr Pro Ser Ser Gly Asp Ser Ser Pro Ala Gly Ala
        500                      505                      510

Pro Ser Pro Phe Asp Lys Glu Thr Glu Gly Gln Phe Tyr Asn Tyr Phe
            515                      520                      525

Pro Asn
    530

<210> SEQ ID NO 5
<211> LENGTH: 3199
<212> TYPE: DNA
<213> ORGANISM: Homo sapiens

<400> SEQUENCE: 5

```
gttttctaa acagcctgac actgagggga ggcagtgaga ctgtaagcag tctgggttgg      60
gcagaaggca gaaaccagc agagtcacag aggagatggc caactgccaa atagccatct     120
tgtaccagag attccagaga gtggtctttg gaatttccca actcctttgc ttcagtgccc     180
tgatctctga actaacaaac cagaaagaag tggcagcatg gacttatcat tacagcacaa     240
aagcatactc atggaatatt tcccgtaaat actgccagaa tcgctacaca gacttagtgg     300
ccatccagaa taaaatgaa attgattacc tcaataaggt cctaccctac tacagctcct     360
actactggat tgggatccga agaacaata agacatggac atgggtggga accaaaaagg     420
ctctcaccaa cgaggctgag aactgggctg ataatgaacc taacaacaaa ggaacaacg     480 aggactgcgt ggagatatac atcaagagtc cgtcagcccc tggcaagtgg aatgatgagc     540
actgcttgaa gaaaaagcac gcattgtgtt cacagcctc ctgccaggac atgtcctgca     600
gcaaacaagg agagtgcctc gagaccatcg gaactacac ctgctcctgt tacccctggat     660 tctatgggcc agaatgtgaa tacgtgagag agtgtggaga acttgagctc cctcaacacg     720
tgctcatgaa ctgcagccac cctctgggaa acttctcttt taactcgcag tgcagcttcc     780
actgcactga cgggtaccaa gtaaatgggc ccagcaagct ggaatgcttg gcttctggaa     840
tctggacaaa taagcctcca cagtgtttag ctgcccagtg cccaccctg aagattcctg     900 aacgaggaaa catgatctgc cttcattctg caaaagcatt ccagcatcag tctagctgca     960
```

```
gcttcagttg tgaagaggga tttgcattag ttggaccgga agtggtgcaa tgcacagcct    1020
cgggggtatg gacagcccca gccccagtgt gtaaagctgt gcagtgtcag cacctggaag    1080
cccccagtga aggaaccatg gactgtgttc atccgctcac tgcttttgcc tatggctcca    1140
gctgcaaatt tgagtgccag cccggctaca gagtgagggg cttggacatg ctccgctgca    1200
ttgactctgg acactggtct gcacccttgc caacctgtga ggctatttcg tgtgagccgc    1260
tggagagtcc tgtccacgga agcatggatt gctctccatc cttgagagcg tttcagtatg    1320
acaccaactg tagcttccgc tgtgctgaag gtttcatgct gagaggagcc gatatagttc    1380
ggtgtgataa cttgggacag tggacagcac cagccccagt ctgtcaagct tgcagtgcc    1440
aggatctccc agttccaaat gaggcccggg tgaactgctc ccacccttc ggtgccttta    1500
ggtaccagtc agtctgcagc ttcacctgca atgaaggctt gctcctggtg ggagcaagtg    1560
tgctacagtg cttggctact ggaaactgga attctgttcc tccagaatgc caagccattc    1620
cctgcacacc tttgctaagc cctcagaatg gaacaatgac ctgtgttcaa cctcttggaa    1680
gttccagtta taaatccaca tgtcaattca tctgtgacga gggatattct ttgtctggac    1740
cagaaagatt ggattgtact cgatcgggac gctggacaga ctccccacca atgtgtgaag    1800
ccatcaagtg cccagaactc tttgccccag agcagggcag cctggattgt tctgacactc    1860
gtggagaatt caatgttggc tccacctgtc atttctcttg taacaatggc tttaagctgg    1920
aggggcccaa taatgtggaa tgcacaactt ctggaagatg gtcagctact ccaccaacct    1980
gcaaaggcat agcatcactt cctactccag ggttgcaatg tccagccctc accactcctg    2040
ggcagggaac catgtactgt aggcatcatc cgggaacctt tggttttaat accacttgtt    2100
actttggctg caacgctgga ttcacactca taggagacag cactctcagc tgcagacctt    2160
caggacaatg gacagcagta actccagcat gcagagctgt gaaatgctca gaactacatg    2220
ttaataagcc aatagcgatg aactgctcca acctctgggg aaacttcagt tatggatcaa    2280
tctgctcttt ccattgtcta gagggccagt tacttaatgg ctctgcacaa acagcatgcc    2340
aagagaatgg ccactggtca actaccgtgc caacctgcca agcaggacca ttgactatcc    2400
aggaagccct gacttacttt ggtggagcgg tggcttctac aataggtctg ataatgggtg    2460
ggacgctcct ggctttgcta agaaaagcgtt tcagacaaaa agatgatggg aaatgcccct    2520
tgaatcctca cagccaccta ggaacatatg gagtttttac aaacgctgca tttgacccga    2580
gtccttaagg tttccataaa acccatgaa tcaaagacat ggaattacct tagattagct    2640
ctggaccagc ctgttggacc cgctctggac caaccctgtt tcctgagttt gggattgtgg    2700
tacaatctca aattctcaac ctaccacccc ttcctgtccc acctcttctc ttcctgtaac    2760
acaagccaca gaagccagga gcaaatgttt ctgcagtagt ctctgtgctt tgactcacct    2820
gttacttgaa ataccagtga accaaagaga ctggagcatc tgactcacaa gaagaccaga    2880
ctgtggagaa ataaaaatac ctctttattt tttgattgaa ggaaggtttt ctccactttg    2940
ttggaaagca ggtggcatct ctaattggaa gaaattcctg tagcatcttc tggagtctcc    3000
agtggttgct gttgatgagg cctccttgac ctctgctctg aggcttccag agagtcctct    3060
ggatggcacc agaggctgca gaaggccaag aatcaagcta gaaggccaca tgtcaccgtg    3120
gaccttcctg ccaccagtca ctgtccctca aatgacccaa agaccaatat tcaaatgcgt    3180
aattaaaaga attttcccc                                                 3199
```

<210> SEQ ID NO 6
<211> LENGTH: 830

<212> TYPE: PRT
<213> ORGANISM: Homo sapiens

<400> SEQUENCE: 6

```
Met Ala Asn Cys Gln Ile Ala Ile Leu Tyr Gln Arg Phe Gln Arg Val
1               5                   10                  15

Val Phe Gly Ile Ser Gln Leu Leu Cys Phe Ser Ala Leu Ile Ser Glu
            20                  25                  30

Leu Thr Asn Gln Lys Glu Val Ala Ala Trp Thr Tyr His Tyr Ser Thr
        35                  40                  45

Lys Ala Tyr Ser Trp Asn Ile Ser Arg Lys Tyr Cys Gln Asn Arg Tyr
50                  55                  60

Thr Asp Leu Val Ala Ile Gln Asn Lys Asn Glu Ile Asp Tyr Leu Asn
65                  70                  75                  80

Lys Val Leu Pro Tyr Tyr Ser Tyr Tyr Trp Ile Gly Ile Arg Lys
                85                  90                  95

Asn Asn Lys Thr Trp Thr Trp Val Gly Thr Lys Ala Leu Thr Asn
                100                 105                 110

Glu Ala Glu Asn Trp Ala Asp Asn Glu Pro Asn Asn Lys Arg Asn Asn
            115                 120                 125

Glu Asp Cys Val Glu Ile Tyr Ile Lys Ser Pro Ser Ala Pro Gly Lys
130                 135                 140

Trp Asn Asp Glu His Cys Leu Lys Lys Lys His Ala Leu Cys Tyr Thr
145                 150                 155                 160

Ala Ser Cys Gln Asp Met Ser Cys Ser Lys Gln Gly Glu Cys Leu Glu
                165                 170                 175

Thr Ile Gly Asn Tyr Thr Cys Ser Cys Tyr Pro Gly Phe Tyr Gly Pro
            180                 185                 190

Glu Cys Glu Tyr Val Arg Glu Cys Gly Glu Leu Glu Leu Pro Gln His
        195                 200                 205

Val Leu Met Asn Cys Ser His Pro Leu Gly Asn Phe Ser Phe Asn Ser
210                 215                 220

Gln Cys Ser Phe His Cys Thr Asp Gly Tyr Gln Val Asn Gly Pro Ser
225                 230                 235                 240

Lys Leu Glu Cys Leu Ala Ser Gly Ile Trp Thr Asn Lys Pro Pro Gln
                245                 250                 255

Cys Leu Ala Ala Gln Cys Pro Pro Leu Lys Ile Pro Glu Arg Gly Asn
            260                 265                 270

Met Ile Cys Leu His Ser Ala Lys Ala Phe Gln His Gln Ser Ser Cys
        275                 280                 285

Ser Phe Ser Cys Glu Glu Gly Phe Ala Leu Val Gly Pro Glu Val Val
290                 295                 300

Gln Cys Thr Ala Ser Gly Val Trp Thr Ala Pro Ala Pro Val Cys Lys
305                 310                 315                 320

Ala Val Gln Cys Gln His Leu Glu Ala Pro Ser Glu Gly Thr Met Asp
                325                 330                 335

Cys Val His Pro Leu Thr Ala Phe Ala Tyr Gly Ser Ser Cys Lys Phe
            340                 345                 350

Glu Cys Gln Pro Gly Tyr Arg Val Arg Gly Leu Asp Met Leu Arg Cys
        355                 360                 365

Ile Asp Ser Gly His Trp Ser Ala Pro Leu Pro Thr Cys Glu Ala Ile
370                 375                 380

Ser Cys Glu Pro Leu Glu Ser Pro Val His Gly Ser Met Asp Cys Ser
385                 390                 395                 400
```

-continued

```
Pro Ser Leu Arg Ala Phe Gln Tyr Asp Thr Asn Cys Ser Phe Arg Cys
            405                 410                 415

Ala Glu Gly Phe Met Leu Arg Gly Ala Asp Ile Val Arg Cys Asp Asn
            420                 425                 430

Leu Gly Gln Trp Thr Ala Pro Ala Pro Val Cys Gln Ala Leu Gln Cys
            435                 440                 445

Gln Asp Leu Pro Val Pro Asn Glu Ala Arg Val Asn Cys Ser His Pro
            450                 455                 460

Phe Gly Ala Phe Arg Tyr Gln Ser Val Cys Ser Phe Thr Cys Asn Glu
465                 470                 475                 480

Gly Leu Leu Leu Val Gly Ala Ser Val Leu Gln Cys Leu Ala Thr Gly
            485                 490                 495

Asn Trp Asn Ser Val Pro Pro Glu Cys Gln Ala Ile Pro Cys Thr Pro
            500                 505                 510

Leu Leu Ser Pro Gln Asn Gly Thr Met Thr Cys Val Gln Pro Leu Gly
            515                 520                 525

Ser Ser Ser Tyr Lys Ser Thr Cys Gln Phe Ile Cys Asp Glu Gly Tyr
            530                 535                 540

Ser Leu Ser Gly Pro Glu Arg Leu Asp Cys Thr Arg Ser Gly Arg Trp
545                 550                 555                 560

Thr Asp Ser Pro Pro Met Cys Glu Ala Ile Lys Cys Pro Glu Leu Phe
            565                 570                 575

Ala Pro Glu Gln Gly Ser Leu Asp Cys Ser Asp Thr Arg Gly Glu Phe
            580                 585                 590

Asn Val Gly Ser Thr Cys His Phe Ser Cys Asn Asn Gly Phe Lys Leu
            595                 600                 605

Glu Gly Pro Asn Asn Val Glu Cys Thr Thr Ser Gly Arg Trp Ser Ala
            610                 615                 620

Thr Pro Pro Thr Cys Lys Gly Ile Ala Ser Leu Pro Thr Pro Gly Leu
625                 630                 635                 640

Gln Cys Pro Ala Leu Thr Thr Pro Gly Gln Gly Thr Met Tyr Cys Arg
            645                 650                 655

His His Pro Gly Thr Phe Gly Phe Asn Thr Thr Cys Tyr Phe Gly Cys
            660                 665                 670

Asn Ala Gly Phe Thr Leu Ile Gly Asp Ser Thr Leu Ser Cys Arg Pro
            675                 680                 685

Ser Gly Gln Trp Thr Ala Val Thr Pro Ala Cys Arg Ala Val Lys Cys
            690                 695                 700

Ser Glu Leu His Val Asn Lys Pro Ile Ala Met Asn Cys Ser Asn Leu
705                 710                 715                 720

Trp Gly Asn Phe Ser Tyr Gly Ser Ile Cys Ser Phe His Cys Leu Glu
            725                 730                 735

Gly Gln Leu Leu Asn Gly Ser Ala Gln Thr Ala Cys Gln Glu Asn Gly
            740                 745                 750

His Trp Ser Thr Thr Val Pro Thr Cys Gln Ala Gly Pro Leu Thr Ile
            755                 760                 765

Gln Glu Ala Leu Thr Tyr Phe Gly Gly Ala Val Ala Ser Thr Ile Gly
            770                 775                 780

Leu Ile Met Gly Gly Thr Leu Leu Ala Leu Leu Arg Lys Arg Phe Arg
785                 790                 795                 800

Gln Lys Asp Asp Gly Lys Cys Pro Leu Asn Pro His Ser His Leu Gly
            805                 810                 815

Thr Tyr Gly Val Phe Thr Asn Ala Ala Phe Asp Pro Ser Pro
            820                 825                 830
```

<210> SEQ ID NO 7
<211> LENGTH: 3075
<212> TYPE: DNA
<213> ORGANISM: Mus musculus

<400> SEQUENCE: 7

| | | | | | |
|---|---|---|---|---|---|
| agagaggaca | tggctggctg | cccaaaaggt | tcctggacgc | caagactccg | gagtgtgatc | 60 |
| ctgggagggg | ctcaactcat | ctggttcagt | gctttgatct | ctgagcttgt | aaatcagaag | 120 |
| gaagtggctg | cgtggaccta | taactacagc | acaaaggcat | actcatggaa | taactcacgg | 180 |
| gtgttctgta | ggaggcactt | cacagactta | gtggccatcc | agaataagaa | tgaaatcgct | 240 |
| cacctcaatg | acgtcatccc | attcttcaac | tcttactact | ggattggtat | ccgaaagatc | 300 |
| aacaataagt | ggacctgggt | gggaacaaat | aagacactca | cggaggaggc | tgagaactgg | 360 |
| gccgacaacg | agcccaacaa | caagaagaac | aatcaggact | gtgtggagat | ctacatcaag | 420 |
| agtaactcgg | cccctggcaa | gtggaatgat | gaaccctgtt | ttaaacgaaa | gcgggccctg | 480 |
| tgctacacag | cctcctgcca | ggacatgtcc | tgcagcaacc | aaggggagtg | catcgagacc | 540 |
| attgggagct | atacctgctc | ctgctaccca | ggcttctatg | gccagagtg | tgaatacgtc | 600 |
| aaggagtgtg | gaaaagtcaa | catccctcaa | catgttctca | tgaactgcag | ccatcccctg | 660 |
| ggggagttct | ccttcaactc | acagtgcacc | ttcagctgtg | ctgagggcta | cgagctggac | 720 |
| ggacccggcg | agctgcaatg | tttggcttct | gggatctgga | caaataaccc | cccgaagtgt | 780 |
| gacgctgtgc | aatgtcagag | cctggaagcc | cctccccatg | gaaccatggc | ctgtatgcac | 840 |
| ccaattgctg | cctttgccta | cgactccagc | tgtaaatttg | agtgccagcc | tggatataga | 900 |
| gcgaggggct | ccaacacact | ccactgcact | ggctctggtc | agtggagtga | accactgcca | 960 |
| acctgtgaag | ctattgcgtg | tgaacctccg | gagatcccca | tccatgggag | catggactgc | 1020 |
| gtcccatcta | caggaaccct | tgggtacaac | agcagctgca | ctttctctg | tgcagagggg | 1080 |
| ttcgtgctga | agggaaatga | tgccattcag | tgtgctgact | ccgggcagtg | gacagcccca | 1140 |
| gccccattct | gtgaagcgtt | gcaatgtcca | gagtttccgg | ttcccagtaa | agcccaggtg | 1200 |
| aactgctcgg | atcccttcgg | taccttgacg | taccagtcag | tctgcagctt | ttcctgtgat | 1260 |
| gaaggctcgc | tcttggtggg | agcaagtgtg | ataagatgcc | tggctactgg | acactggaat | 1320 |
| ggggctcctc | ccgaatgtca | agctgtgtcc | tgtgccccta | tgctcagtcc | tgagaatgga | 1380 |
| tccatgacct | gcgttcagcc | tcttgggaat | tccacctaca | atccacatg | ccagttcatg | 1440 |
| tgcgatgaag | gattttatct | atctggaccg | gaaagactgg | attgttctcc | atctggacac | 1500 |
| tggacaggca | cccctcccac | gtgtgaagcc | atcaagtgtc | caggaatctt | cgccccagag | 1560 |
| caaggcaacc | tggattgttc | tcatgtccac | ggagagtttg | gtgttggctc | tatctgtcac | 1620 |
| ttctcctgca | atgaggactt | tgagctactg | ggatctgaaa | atgtgaaatg | cacagtgtct | 1680 |
| ggaagatggt | cagcacctcc | gccaacctgc | aaaggcataa | catcacttcc | tgccccagca | 1740 |
| gtccgatgcc | ctgccctcac | gactcctgga | cagggcacaa | tgtcctgcca | acaccacctg | 1800 |
| ggaagctttg | gtccgaacac | cacttgttac | tttgggtgca | aaaccggatt | tacactcagg | 1860 |
| ggagccaact | cgctccgctg | cagggcttca | ggacaatgga | cagcagtgac | ccccatgtgc | 1920 |
| agagcggtca | atgctccga | attgcacatg | gacacagcag | tagcaatgaa | ctgttccaat | 1980 |
| ccctggggaa | actttagcta | tggatcaacc | tgcaccttcc | agtgcccaga | ggggcagtca | 2040 |
| ctgaacggct | ctgtgagagc | aacctgccga | gaggacggtc | actggtcaga | tgccatgcca | 2100 |
| acctgccaag | cagggacact | gacaatccag | gaagctctga | cgtacttggg | tggtgcagtg | 2160 |

```
gcttctacaa caggcctggc agtgggcggg acactcctgg ctctgctaag aaagcgtctc    2220
agaaagaaag atgatggaaa atgccccttg aaccctcaca gccacctagg aacatacgga    2280
gtcttcacta acgctgcata tgacccaacc ccttaagaaa cccggtctgc caatgtctca    2340
ttcgatttct caggattcca catgcaagtg tcaagtttcc tgtcacactt gactgtaact    2400
ccatggcatt tgggcatttg ctgaggttct ctgtagttta aacaaaaaaa caaaacaaaa    2460
caaaaaaaag gacaggaacc tagaaaaaga actatgcact tcccacctc tccacccacc     2520 ccttcctgct ccgcccctca ccttcctcca gctccgcccc ttcctgctcc gcccctcacc    2580
ttcctccagc tccgcccctt cctgctccgc ccctcacctt cctccagctc agccacagac    2640
ccaggagcaa atgtttctgc tctggtctgt ggcttgttgt tactttgctg ttgctgaaaa    2700
cgggagagtc caaggccctg gagcatcttc ctcaccaggt gaccaggctc tggaaaaccg    2760
aaggtctttc tcttgggatt gcagagtagc aatgttggtg ggcaggcaga cctctagttt    2820
aaggggatgc ctgctttaag atctcctggg tcttccatgt ttcatatcaa tgaggttgtt    2880
tacacctctg ctgctgagac tttcacagaa acctccagat ggtactaggg gacacagaag    2940
atctggaaca gagccaagac gtcacatctg actgcagact ttccctccac caaagcaccc    3000
aaagatcatt gtttggatgt ataaataact caacttcccc aaaaaaaaaa aaaaaaaaa     3060 aaaaaaaaaa aaaaa                                                     3075

<210> SEQ ID NO 8
<211> LENGTH: 761
<212> TYPE: PRT
<213> ORGANISM: Mus musculus

<400> SEQUENCE: 8

Met Ala Gly Cys Pro Lys Gly Ser Trp Thr Pro Arg Leu Arg Ser Val
1               5                   10                  15

Ile Leu Gly Gly Ala Gln Leu Ile Trp Phe Ser Ala Leu Ile Ser Glu
            20                  25                  30

Leu Val Asn Gln Lys Glu Val Ala Ala Trp Thr Tyr Asn Tyr Ser Thr
        35                  40                  45

Lys Ala Tyr Ser Trp Asn Asn Ser Arg Val Phe Cys Arg Arg His Phe
    50                  55                  60

Thr Asp Leu Val Ala Ile Gln Asn Lys Asn Glu Ile Ala His Leu Asn
65                  70                  75                  80

Asp Val Ile Pro Phe Phe Asn Ser Tyr Tyr Trp Ile Gly Ile Arg Lys
                85                  90                  95

Ile Asn Asn Lys Trp Thr Trp Val Gly Thr Asn Lys Thr Leu Thr Glu
            100                 105                 110

Glu Ala Glu Asn Trp Ala Asp Asn Glu Pro Asn Asn Lys Lys Asn Asn
        115                 120                 125

Gln Asp Cys Val Glu Ile Tyr Ile Lys Ser Asn Ser Ala Pro Gly Lys
    130                 135                 140

Trp Asn Asp Glu Pro Cys Phe Lys Arg Lys Arg Ala Leu Cys Tyr Thr
145                 150                 155                 160

Ala Ser Cys Gln Asp Met Ser Cys Ser Asn Gln Gly Glu Cys Ile Glu
                165                 170                 175

Thr Ile Gly Ser Tyr Thr Cys Ser Cys Tyr Pro Gly Phe Tyr Gly Pro
            180                 185                 190

Glu Cys Glu Tyr Val Lys Glu Cys Gly Lys Val Asn Ile Pro Gln His
        195                 200                 205
```

-continued

```
Val Leu Met Asn Cys Ser His Pro Leu Gly Glu Phe Ser Phe Asn Ser
    210                 215                 220
Gln Cys Thr Phe Ser Cys Ala Glu Gly Tyr Glu Leu Asp Gly Pro Gly
225                 230                 235                 240
Glu Leu Gln Cys Leu Ala Ser Gly Ile Trp Thr Asn Asn Pro Pro Lys
                245                 250                 255
Cys Asp Ala Val Gln Cys Gln Ser Leu Glu Ala Pro Pro His Gly Thr
            260                 265                 270
Met Ala Cys Met His Pro Ile Ala Ala Phe Ala Tyr Asp Ser Ser Cys
        275                 280                 285
Lys Phe Glu Cys Gln Pro Gly Tyr Arg Ala Arg Gly Ser Asn Thr Leu
    290                 295                 300
His Cys Thr Gly Ser Gly Gln Trp Ser Glu Pro Leu Pro Thr Cys Glu
305                 310                 315                 320
Ala Ile Ala Cys Glu Pro Pro Glu Ile Pro Ile His Gly Ser Met Asp
                325                 330                 335
Cys Val Pro Ser Thr Gly Thr Phe Gly Tyr Asn Ser Ser Cys Thr Phe
            340                 345                 350
Leu Cys Ala Glu Gly Phe Val Leu Lys Gly Asn Asp Ala Ile Gln Cys
        355                 360                 365
Ala Asp Ser Gly Gln Trp Thr Ala Pro Ala Pro Phe Cys Glu Ala Leu
    370                 375                 380
Gln Cys Pro Glu Phe Pro Val Pro Ser Lys Ala Gln Val Asn Cys Ser
385                 390                 395                 400
Asp Pro Phe Gly Thr Leu Thr Tyr Gln Ser Val Cys Ser Phe Ser Cys
                405                 410                 415
Asp Glu Gly Ser Leu Leu Val Gly Ala Ser Val Ile Arg Cys Leu Ala
            420                 425                 430
Thr Gly His Trp Asn Gly Ala Pro Pro Glu Cys Gln Ala Val Ser Cys
        435                 440                 445
Ala Pro Met Leu Ser Pro Glu Asn Gly Ser Met Thr Cys Val Gln Pro
    450                 455                 460
Leu Gly Asn Ser Thr Tyr Lys Ser Thr Cys Gln Phe Met Cys Asp Glu
465                 470                 475                 480
Gly Phe Tyr Leu Ser Gly Pro Glu Arg Leu Asp Cys Ser Pro Ser Gly
                485                 490                 495
His Trp Thr Gly Thr Pro Pro Thr Cys Glu Ala Ile Lys Cys Pro Gly
            500                 505                 510
Ile Phe Ala Pro Glu Gln Gly Asn Leu Asp Cys Ser His Val His Gly
        515                 520                 525
Glu Phe Gly Val Gly Ser Ile Cys His Phe Ser Cys Asn Glu Asp Phe
    530                 535                 540
Glu Leu Leu Gly Ser Glu Asn Val Glu Cys Thr Val Ser Gly Arg Trp
545                 550                 555                 560
Ser Ala Pro Pro Pro Thr Cys Lys Gly Ile Thr Ser Leu Pro Ala Pro
                565                 570                 575
Ala Val Arg Cys Pro Ala Leu Thr Thr Pro Gly Gln Gly Thr Met Ser
            580                 585                 590
Cys Gln His His Leu Gly Ser Phe Gly Pro Asn Thr Thr Cys Tyr Phe
        595                 600                 605
Gly Cys Lys Thr Gly Phe Thr Leu Arg Gly Ala Asn Ser Leu Arg Cys
    610                 615                 620
Arg Ala Ser Gly Gln Trp Thr Ala Val Thr Pro Met Cys Arg Ala Val
625                 630                 635                 640
```

```
Lys Cys Ser Glu Leu His Met Asp Thr Ala Val Ala Met Asn Cys Ser
            645                 650                 655

Asn Pro Trp Gly Asn Phe Ser Tyr Gly Ser Thr Cys Thr Phe Gln Cys
            660                 665                 670

Pro Glu Gly Gln Ser Leu Asn Gly Ser Val Arg Ala Thr Cys Arg Glu
            675                 680                 685

Asp Gly His Trp Ser Asp Ala Met Pro Thr Cys Gln Ala Gly Thr Leu
            690                 695                 700

Thr Ile Gln Glu Ala Leu Thr Tyr Leu Gly Gly Ala Val Ala Ser Thr
705                 710                 715                 720

Thr Gly Leu Ala Val Gly Gly Thr Leu Leu Ala Leu Leu Arg Lys Arg
                725                 730                 735

Leu Arg Lys Lys Asp Asp Gly Lys Cys Pro Leu Asn Pro His Ser His
            740                 745                 750

Leu Gly Thr Tyr Gly Val Phe Thr Asn
            755                 760

<210> SEQ ID NO 9
<211> LENGTH: 3834
<212> TYPE: DNA
<213> ORGANISM: Homo sapiens

<400> SEQUENCE: 9
cctgagacag aggcagcagt gatacccacc tgagagatcc tgtgtttgaa caactgcttc      60
ccaaaacgga agtatttcca agcctaaacc tttgggtgaa agaactcttg aagtcatga     120
ttgcttcaca gtttctctca gctctcactt tggtgcttct cattaaagag agtggagcct     180
ggtcttacaa cacctccacg gaagctatga cttatgatga ggccagtgct tattgtcagc     240
aaaggtacac acacctggtt gcaattcaaa acaaagaaga gattgagtac ctaaactcca     300
tattgagcta ttcaccaagt tattactgga ttggaatcag aaaagtcaac aatgtgtggg     360
tctgggtagg aacccagaaa cctctgacag aagaagccaa gaactgggct ccaggtgaac     420
ccaacaatag gcaaaaagat gaggactgcg tggagatcta catcaagaga gaaaaagatg     480
tgggcatgtg gaatgatgag aggtgcagca agaagaagct tgccctatgc tacacagctg     540
cctgtaccaa tacatcctgc agtggccacg gtgaatgtgt agagaccatc aataattaca     600
cttgcaagtg tgaccctggc ttcagtggac tcaagtgtga gcaaattgtg aactgtacag     660
ccctggaatc ccctgagcat ggaagcctgg tttgcagtca cccactggga aacttcagct     720
acaattcttc ctgctctatc agctgtgata ggggttacct gccaagcagc atggagacca     780
tgcagtgtat gtcctctgga aatggagtg ctcctattcc agcctgcaat gtggttgagt     840
gtgatgctgt gacaaatcca gccaatgggt tcgtggaatg tttccaaaac cctggaagct     900
tcccatggaa cacaacctgt acatttgact gtgaagaagg atttgaacta atgggagccc     960
agagccttca gtgtacctca tctgggaatt gggacaacga gaagccaacg tgtaaagctg    1020
tgacatgcag ggccgtccgc cagcctcaga atgctctgt gaggtgcagc cattcccctg    1080
ctggagagtt caccttcaaa tcatcctgca acttcacctg tgaggaaggc ttcatgttgc    1140
agggaccagc ccaggttgaa tgcaccactc aagggcagtg gacacagcaa atcccagttt    1200
gtgaagcttt ccagtgcaca gccttgtcca acccgagcg aggctacatg aattgtcttc    1260
ctagtgcttc tggcagtttc cgttatgggt ccagctgtga ttctcctgt gagcagggtt    1320
ttgtgttgaa gggatccaaa aggctccaat gtggccccac aggggagtgg acaacgaga    1380
agcccacatg tgaagctgtg agatgcgatg ctgtccacca gcccccgaag ggtttggtga    1440
```

-continued

```
ggtgtgctca ttcccctatt ggagaattca cctacaagtc ctcttgtgcc ttcagctgtg    1500
aggagggatt tgaattatat ggatcaactc aacttgagtg cacatctcag ggacaatgga    1560
cagaagaggt tccttcctgc caagtggtaa aatgttcaag cctggcagtt ccgggaaaga    1620
tcaacatgag ctgcagtggg gagcccgtgt ttggcactgt gtgcaagttc gcctgtcctg    1680
aaggatggac gctcaatggc tctgcagctc ggacatgtgg agccacagga cactggtctg    1740
gcctgctacc tacctgtgaa gctcccactg agtccaacat tcccttggta gctggacttt    1800
ctgctgctgg actctcccct ctgacattag caccatttct cctctggctt cggaaatgct    1860
tacggaaagc aaagaaattt gttcctgcca gcagctgcca aagccttgaa tcagacggaa    1920
gctaccaaaa gccttcttac atcctttaag ttcaaaagaa tcagaaacag gtgcatctgg    1980
ggaactagag ggatacactg aagttaacag agacagataa ctctcctcgg gtctctggcc    2040
cttcttgcct actatgccag atgcctttat ggctgaaacc gcaacaccca tcaccacttc    2100
aatagatcaa agtccagcag gcaaggacgg ccttcaactg aaaagactca gtgttccctt    2160
tcctactctc aggatcaaga aagtgttggc taatgaaggg aaaggatatt ttcttccaag    2220
caaaggtgaa gagaccaaga ctctgaaatc tcagaattcc ttttctaact ctcccttgct    2280
cgctgtaaaa tcttggcaca gaaacacaat attttgtggc tttctttctt tgcccttca    2340 cagtgtttcg acagctgatt acacagttgc tgtcataaga atgaataata attatccaga    2400
gtttagagga aaaaaatgac taaaaatatt ataacttaaa aaaatgacag atgttgaatg    2460
cccacaggca aatgcatgga gggttgttaa tggtgcaaat cctactgaat gctctgtgcg    2520
agggttacta tgcacaattt aatcactttc atccctatgg gattcagtgc ttcttaaaga    2580
gttcttaagg attgtgatat ttttacttgc attgaatata ttataatctt ccatacttct    2640
tcattcaata caagtgtggt agggacttaa aaaacttgta aatgctgtca actatgatat    2700
ggtaaaagtt acttattcta gattacccccc tcattgttta ttaacaaatt atgttacatc    2760
tgttttaaat ttatttcaaa aagggaaact attgtcccct agcaaggcat gatgttaacc    2820
agaataaagt tctgagtgtt tttactacag ttgttttttg aaaacatggt agaattggag    2880
agtaaaaact gaatggaagg tttgtatatt gtcagatatt ttttcagaaa tatgtggttt    2940
ccacgatgaa aaacttccat gaggccaaac gttttgaact aataaaagca taaatgcaaa    3000
cacacaaagg tataatttta tgaatgtctt tgttggaaaa gaatacagaa agatggatgt    3060
gctttgcatt cctacaaaga tgtttgtcag atgtgatatg taaacataat tcttgtatat    3120 tatgaagat tttaaattca caatagaaac tcaccatgta aaagagtcat ctggtagatt    3180
tttaacgaat gaagatgtct aatagttatt ccctatttgt tttcttctgt atgttagggt    3240
gctctggaag agaggaatgc ctgtgtgagc aagcatttat gtttatttat aagcagattt    3300
aacaattcca aaggaatctc cagtttttcag ttgatcactg gcaatgaaaa attctcagtc    3360
agtaattgcc aaagctgctc tagccttgag gagtgtgaga atcaaaactc tcctacactt    3420
ccattaactt agcatgtgtt gaaaaaaaaa gttcagaga agttctggct gaacactggc    3480
aacgacaaag ccaacagtca aaacagagat gtgataagga tcagaacagc agaggttctt    3540 ttaaagggc agaaaactc tgggaaataa gagagaacaa ctactgtgat caggctatgt    3600
atggaataca gtgttatttt ctttgaaatt gtttaagtgt tgtaaatatt tatgtaaact    3660
gcattagaaa ttagctgtgt gaaataccag tgtggtttgt gtttgagttt tattgagaat    3720
tttaaattat aacttaaaat attttataat ttttaaagta tatatttatt taagcttatg    3780
tcagacctat ttgacataac actataaagg ttgacaataa atgtgcttat gttt          3834
```

-continued

```
<210> SEQ ID NO 10
<211> LENGTH: 610
<212> TYPE: PRT
<213> ORGANISM: Homo sapiens

<400> SEQUENCE: 10

Met Ile Ala Ser Gln Phe Leu Ser Ala Leu Thr Leu Val Leu Leu Ile
1               5                   10                  15

Lys Glu Ser Gly Ala Trp Ser Tyr Asn Thr Ser Thr Glu Ala Met Thr
            20                  25                  30

Tyr Asp Glu Ala Ser Ala Tyr Cys Gln Gln Arg Tyr Thr His Leu Val
        35                  40                  45

Ala Ile Gln Asn Lys Glu Glu Ile Glu Tyr Leu Asn Ser Ile Leu Ser
    50                  55                  60

Tyr Ser Pro Ser Tyr Tyr Trp Ile Gly Ile Arg Lys Val Asn Asn Val
65                  70                  75                  80

Trp Val Trp Val Gly Thr Gln Lys Pro Leu Thr Glu Glu Ala Lys Asn
                85                  90                  95

Trp Ala Pro Gly Glu Pro Asn Asn Arg Gln Lys Asp Glu Asp Cys Val
            100                 105                 110

Glu Ile Tyr Ile Lys Arg Glu Lys Asp Val Gly Met Trp Asn Asp Glu
        115                 120                 125

Arg Cys Ser Lys Lys Lys Leu Ala Leu Cys Tyr Thr Ala Ala Cys Thr
    130                 135                 140

Asn Thr Ser Cys Ser Gly His Gly Glu Cys Val Glu Thr Ile Asn Asn
145                 150                 155                 160

Tyr Thr Cys Lys Cys Asp Pro Gly Phe Ser Gly Leu Lys Cys Glu Gln
                165                 170                 175

Ile Val Asn Cys Thr Ala Leu Glu Ser Pro Glu His Gly Ser Leu Val
            180                 185                 190

Cys Ser His Pro Leu Gly Asn Phe Ser Tyr Asn Ser Ser Cys Ser Ile
        195                 200                 205

Ser Cys Asp Arg Gly Tyr Leu Pro Ser Ser Met Glu Thr Met Gln Cys
    210                 215                 220

Met Ser Ser Gly Glu Trp Ser Ala Pro Ile Pro Ala Cys Asn Val Val
225                 230                 235                 240

Glu Cys Asp Ala Val Thr Asn Pro Ala Asn Gly Phe Val Glu Cys Phe
                245                 250                 255

Gln Asn Pro Gly Ser Phe Pro Trp Asn Thr Thr Cys Thr Phe Asp Cys
            260                 265                 270

Glu Glu Gly Phe Glu Leu Met Gly Ala Gln Ser Leu Gln Cys Thr Ser
        275                 280                 285

Ser Gly Asn Trp Asp Asn Glu Lys Pro Thr Cys Lys Ala Val Thr Cys
    290                 295                 300

Arg Ala Val Arg Gln Pro Gln Asn Gly Ser Val Arg Cys Ser His Ser
305                 310                 315                 320

Pro Ala Gly Glu Phe Thr Phe Lys Ser Ser Cys Asn Phe Thr Cys Glu
                325                 330                 335

Glu Gly Phe Met Leu Gln Gly Pro Ala Gln Val Glu Cys Thr Thr Gln
            340                 345                 350

Gly Gln Trp Thr Gln Gln Ile Pro Val Cys Glu Ala Phe Gln Cys Thr
        355                 360                 365

Ala Leu Ser Asn Pro Glu Arg Gly Tyr Met Asn Cys Leu Pro Ser Ala
    370                 375                 380
```

| | | | | | | | | | | | |
|---|---|---|---|---|---|---|---|---|---|---|---|
|Ser|Gly|Ser|Phe|Arg|Tyr|Gly|Ser|Ser|Cys|Glu|Phe Ser Cys Glu Gln|
|385| | | |390| | | |395| | |400|

Gly Phe Val Leu Lys Gly Ser Lys Arg Leu Gln Cys Gly Pro Thr Gly
              405                 410                 415

Glu Trp Asp Asn Glu Lys Pro Thr Cys Glu Ala Val Arg Cys Asp Ala
        420                 425                 430

Val His Gln Pro Pro Lys Gly Leu Val Arg Cys Ala His Ser Pro Ile
    435                 440                 445

Gly Glu Phe Thr Tyr Lys Ser Ser Cys Ala Phe Ser Cys Glu Glu Gly
        450                 455                 460

Phe Glu Leu Tyr Gly Ser Thr Gln Leu Glu Cys Thr Ser Gln Gly Gln
465                 470                 475                 480

Trp Thr Glu Glu Val Pro Ser Cys Gln Val Val Lys Cys Ser Ser Leu
                485                 490                 495

Ala Val Pro Gly Lys Ile Asn Met Ser Cys Ser Gly Glu Pro Val Phe
            500                 505                 510

Gly Thr Val Cys Lys Phe Ala Cys Pro Glu Gly Trp Thr Leu Asn Gly
        515                 520                 525

Ser Ala Ala Arg Thr Cys Gly Ala Thr Gly His Trp Ser Gly Leu Leu
    530                 535                 540

Pro Thr Cys Glu Ala Pro Thr Glu Ser Asn Ile Pro Leu Val Ala Gly
545                 550                 555                 560

Leu Ser Ala Ala Gly Leu Ser Leu Leu Thr Leu Ala Pro Phe Leu Leu
                565                 570                 575

Trp Leu Arg Lys Cys Leu Arg Lys Ala Lys Lys Phe Val Pro Ala Ser
            580                 585                 590

Ser Cys Gln Ser Leu Glu Ser Asp Gly Ser Tyr Gln Lys Pro Ser Tyr
        595                 600                 605

Ile Leu
    610

<210> SEQ ID NO 11
<211> LENGTH: 2911
<212> TYPE: DNA
<213> ORGANISM: Mus musculus

<400> SEQUENCE: 11
cacagcaaaa ctgcgagaag aacggataga gagaagcagg agcaatacac ctaagggatc      60
caacgccaga caacaattc cactgaacag aaagtttctc cagtctagcg cctggatgaa     120
agcaactgct ggagtcatga atgcctcgcg ctttctctct gctcttgttt ttgttctcct     180
cgctggagag agcacagctt ggtactacaa tgcctccagt gagctcatga cgtatgatga     240
agccagtgca tactgtcagc gggactacac acatctggtg gcgattcaga acaaggaaga     300
gatcaactac cttaactcca atctgaaaca ttcaccgagt tactactgga ttggaatcag     360
aaaagtcaat aacgtatgga tctgggtggg gacggggaag cctctgacag aggaagctca     420
gaactgggct ccaggtgaac caaacaacaa acaaagaaat gaggactgtg tagagattta     480
catccaacga accaaagact cgggcatgtg aatgacgag agatgtaaca aaaagaagct     540
ggctctgtgc tacacagctt cgtgtaccaa tgcatcctgc agtggtcatg gtgaatgcat     600
agagaccatc aatagttaca cctgcaagtg ccaccctggc ttcctgggac ccaactgtga     660
gcaagctgtg acttgcaaac cacaggaaca ccctgactat ggaagcctga actgctccca     720
cccgttcggc cccttcagct ataattcctc ctgctccttt ggctgtaaaa ggggctacct     780

| | |
|---|---|
| gcccagcagc atggagacca ccgtgcggtg tacgtcctct ggagagtgga gtgcgcctgc | 840 |
| tccagcctgc catgtggttg aatgtgaagc tttgacccac cctgcccacg gtatcaggaa | 900 |
| atgttcctca atcctggga gctacccatg aacacgaca tgcacgtttg actgtgtgga | 960 |
| agggtacagg cgagttggag ctcagaatct acagtgtacc tcatctggca tctgggataa | 1020 |
| cgagacgcca tcatgcaaag ctgtgacctg tgacgccatc cctcagcctc agaatggctt | 1080 |
| tgtgagctgc agccactcaa cagctggaga acttgcgttt aagtcatcct gtaacttcac | 1140 |
| ctgtgagcag agtttcacgt tgcaggggcc agcgcaggtt gaatgcagcg cacaagggca | 1200 |
| gtggacacca caaatcccag tctgcaaagc tgtccagtgt gaagccttat ctgcgccaca | 1260 |
| gcagggcaac atgaaatgtc ttcccagtgc ttctggacct ttccaaaatg ggtccagttg | 1320 |
| tgagttctcc tgcgaagaag gatttgaact gaagggatca agaagacttc agtgtggtcc | 1380 |
| aagagggaa tgggatagca agaagcccac gtgttcagct gtgaaatgtg atgatgtccc | 1440 |
| tcggccccag aatggcgtca tggagtgtgc tcatgctact actggagaat tcacctacaa | 1500 |
| gtcctcatgt gcctttcaat gcaatgaggg ctttagcttg catggctcag ctcaacttga | 1560 |
| gtgcacatct cagggaaagt ggacccagga agtcccctcc tgccaagtgg tacaatgtcc | 1620 |
| aagccttgac gtcccgggaa agatgaacat gagctgcagc ggaacagcag ttttcggcac | 1680 |
| agtgtgtgag tttacatgtc ctgatgattg gacactcaat ggatctgcag ttctgacgtg | 1740 |
| tggtgccacg ggacgctggt ctgggatgcc gcctacctgt gaagcccag tcagcccac | 1800 |
| ccgtcccttg gtagttgcac tttctgcggc aggaacctca ctcctgacat cgtcctcatt | 1860 |
| gctctacttg ttgatgagat actttcggaa gaaagcaaag aaatttgttc ctgctagcag | 1920 |
| ctgccaaagc cttcaatcat ttgaaaacta ccatgtgcct tcttacaacg tctaggttca | 1980 |
| aaacaatcag gaacacaaat gcatcgtggg aaatagaatg ataagctgaa gacagcagga | 2040 |
| aatgaactgt ctacagaatc ctggttcctc ttgcctgctt aaaaactggg atcccgactc | 2100 |
| catggatcaa aactgagtga caaggccagc cctctaccag aatgactcag tttcctcttt | 2160 |
| cctagttagt gacagtatga agaacatgct gccacagaag gtggaggtgc tctcttcaaa | 2220 |
| agagagtgaa tggacggggg agagcgcgag ctggaatagc agaatccatt ctgactctta | 2280 |
| gtcatgctag aatttgggaa cagaaacagc gttttattgc tttgtttctt tctcttgttc | 2340 |
| cccacacagt gtgtcaacag ctaattccag tattgttgtc acaggcgtaa ataatattta | 2400 |
| tcagcagttt tgagcaaatg attttctatt tctatcttga aaacaaaaa aggcagaatt | 2460 |
| gccatattct caggttatgg cctaggagtg tcattacggg tacaaggtgc agttcctggt | 2520 |
| gaatataaca tgttaagact gctaggcaga catattggct ttatcccatg ggattcagtg | 2580 |
| gctgccgaag tattcttgaa cattgtgttc tgtgtcctgg cactgaagcc agcatgagat | 2640 |
| ccatcattct tatgtcagct caagggtcaa aaggacttaa aaaaaaatca gaatcctgtg | 2700 |
| gcctatcaca tggcaaaagt tatcctaaat cttttttta attagaaaat ccctaaatct | 2760 |
| aaaattaatg ttatatctgc agcccactta ttttcaaaat gagaaattaa taatcagtgt | 2820 |
| gaaatcctga gtatttaacg gtagctggtt ttaagacatg gtactatcag aagaatagaa | 2880 |
| agtgaagaga gagtttagat atttgatccc c | 2911 |

<210> SEQ ID NO 12
<211> LENGTH: 619
<212> TYPE: PRT
<213> ORGANISM: Mus musculus

<400> SEQUENCE: 12

```
Met Lys Ala Thr Ala Gly Val Met Asn Ala Ser Arg Phe Leu Ser Ala
1               5                   10                  15

Leu Val Phe Val Leu Leu Ala Gly Glu Ser Thr Ala Trp Tyr Tyr Asn
            20                  25                  30

Ala Ser Ser Glu Leu Met Thr Tyr Asp Glu Ala Ser Ala Tyr Cys Gln
        35                  40                  45

Arg Asp Tyr Thr His Leu Val Ala Ile Gln Asn Lys Glu Glu Ile Asn
    50                  55                  60

Tyr Leu Asn Ser Asn Leu Lys His Ser Pro Ser Tyr Tyr Trp Ile Gly
65                  70                  75                  80

Ile Arg Lys Val Asn Asn Val Trp Ile Trp Val Gly Thr Gly Lys Pro
                85                  90                  95

Leu Thr Glu Glu Ala Gln Asn Trp Ala Pro Gly Glu Pro Asn Asn Lys
            100                 105                 110

Gln Arg Asn Glu Asp Cys Val Glu Ile Tyr Ile Gln Arg Thr Lys Asp
        115                 120                 125

Ser Gly Met Trp Asn Asp Glu Arg Cys Asn Lys Lys Lys Leu Ala Leu
    130                 135                 140

Cys Tyr Thr Ala Ser Cys Thr Asn Ala Ser Cys Ser Gly His Gly Glu
145                 150                 155                 160

Cys Ile Glu Thr Ile Asn Ser Tyr Thr Cys Lys Cys His Pro Gly Phe
                165                 170                 175

Leu Gly Pro Asn Cys Glu Gln Ala Val Thr Cys Lys Pro Gln Glu His
            180                 185                 190

Pro Asp Tyr Gly Ser Leu Asn Cys Ser His Pro Phe Gly Pro Phe Ser
        195                 200                 205

Tyr Asn Ser Ser Cys Ser Phe Gly Cys Lys Arg Gly Tyr Leu Pro Ser
    210                 215                 220

Ser Met Glu Thr Thr Val Arg Cys Thr Ser Ser Gly Glu Trp Ser Ala
225                 230                 235                 240

Pro Ala Pro Ala Cys His Val Val Glu Cys Glu Ala Leu Thr His Pro
                245                 250                 255

Ala His Gly Ile Arg Lys Cys Ser Ser Asn Pro Gly Ser Tyr Pro Trp
            260                 265                 270

Asn Thr Thr Cys Thr Phe Asp Cys Val Glu Gly Tyr Arg Arg Val Gly
        275                 280                 285

Ala Gln Asn Leu Gln Cys Thr Ser Ser Gly Ile Trp Asp Asn Glu Thr
    290                 295                 300

Pro Ser Cys Lys Ala Val Thr Cys Asp Ala Ile Pro Gln Pro Gln Asn
305                 310                 315                 320

Gly Phe Val Ser Cys Ser His Ser Thr Ala Gly Glu Leu Ala Phe Lys
                325                 330                 335

Ser Ser Cys Asn Phe Thr Cys Glu Gln Ser Phe Thr Leu Gln Gly Pro
            340                 345                 350

Ala Gln Val Glu Cys Ser Ala Gln Gly Gln Trp Thr Pro Gln Ile Pro
        355                 360                 365

Val Cys Lys Ala Val Gln Cys Glu Ala Leu Ser Ala Pro Gln Gln Gly
    370                 375                 380

Asn Met Lys Cys Leu Pro Ser Ala Ser Gly Pro Phe Gln Asn Gly Ser
385                 390                 395                 400

Ser Cys Glu Phe Ser Cys Glu Glu Gly Phe Glu Leu Lys Gly Ser Arg
                405                 410                 415

Arg Leu Gln Cys Gly Pro Arg Gly Glu Trp Asp Ser Lys Lys Pro Thr
            420                 425                 430
```

```
Cys Ser Ala Val Lys Cys Asp Asp Val Pro Arg Pro Gln Asn Gly Val
        435                 440                 445
Met Glu Cys Ala His Ala Thr Thr Gly Glu Phe Thr Tyr Lys Ser Ser
    450                 455                 460
Cys Ala Phe Gln Cys Asn Glu Gly Phe Ser Leu His Gly Ser Ala Gln
465                 470                 475                 480
Leu Glu Cys Thr Ser Gln Gly Lys Trp Thr Gln Glu Val Pro Ser Cys
                485                 490                 495
Gln Val Val Gln Cys Pro Ser Leu Asp Val Pro Gly Lys Met Asn Met
            500                 505                 510
Ser Cys Ser Gly Thr Ala Val Phe Gly Thr Val Cys Glu Phe Thr Cys
        515                 520                 525
Pro Asp Asp Trp Thr Leu Asn Gly Ser Ala Val Leu Thr Cys Gly Ala
        530                 535                 540
Thr Gly Arg Trp Ser Gly Met Pro Pro Thr Cys Glu Ala Pro Val Ser
545                 550                 555                 560
Pro Thr Arg Pro Leu Val Val Ala Leu Ser Ala Ala Gly Thr Ser Leu
                565                 570                 575
Leu Thr Ser Ser Ser Leu Leu Tyr Leu Leu Met Arg Tyr Phe Arg Lys
                580                 585                 590
Lys Ala Lys Lys Phe Val Pro Ala Ser Ser Cys Gln Ser Leu Gln Ser
            595                 600                 605
Phe Glu Asn Tyr His Val Pro Ser Tyr Asn Val
        610                 615

<210> SEQ ID NO 13
<211> LENGTH: 2324
<212> TYPE: DNA
<213> ORGANISM: Homo sapiens

<400> SEQUENCE: 13
ctcccttggg gcaaggacct gagacccttg tgctaagtca agaggctcaa tgggctgcag     60
aagaactaga gaaggaccaa gcaaagccat gatatttcca tggaaatgtc agagcaccca    120
gagggactta tggaacatct tcaagttgtg ggggtggaca atgctctgtt gtgatttcct    180
ggcacatcat ggaaccgact gctggactta ccattattct gaaaaaccca tgaactggca    240
aagggctaga agattctgcc gagacaatta cacagattta gttgccatac aaaacaaggc    300
ggaaattgag tatctggaga agactctgcc tttcagtcgt tcttactact ggataggaat    360
ccggaagata ggaggaatat ggacgtgggt gggaaccaac aaatctctta ctgaagaagc    420
agagaactgg ggagatggtg agcccaacaa caagaagaac aaggaggact gcgtggagat    480
ctatatcaag agaaacaaag atgcaggcaa atggaacgat gacgcctgcc acaaactaaa    540
ggcagcccct cgttacacag cttcttgcca gccctggtca tgcagtggcc atggagaatg    600
tgtagaaatc atcaataatt acacctgcaa ctgtgatgtg gggtactatg ggccccagtg    660
tcagtttgtg attcagtgtg agcctttgga ggccccagag ctgggtacca tggactgtac    720
tcaccctttg ggaaacttca gcttcagctc acagtgtgcc ttcagctgct ctgaggaac     780 aaacttaact gggattgaag aaaccacctg tggaccattt ggaaactggt catctccaga    840
accaacctgt caagtgattc agtgtgagcc tctatcagca ccagattggg ggatcatgaa    900
ctgtagccat ccctggcca gcttcagctt tacctctgca tgtaccttca tctgctcaga    960
aggaactgag ttaattggga agaagaaaac catttgtgaa tcatctggaa tctggtcaaa   1020
tcctagtcca atatgtcaaa aattggacaa agtttctca atgattaagg agggtgatta   1080
```

-continued

```
taacccctc ttcattccag tggcagtcat ggttactgca ttctctgggt tggcatttat      1140
catttggctg gcaaggagat taaaaaaagg caagaaatcc aagagaagta tgaatgaccc      1200
atattaaatc gcccttggtg aaagaaaatt cttggaatac taaaaatcat gagatccttt      1260
aaatccttcc atgaaacgtt ttgtgtggtg gcacctccta cgtcaaacat gaagtgtgtt      1320
tccttcagtg catctgggaa gatttctacc tgaccaacag ttccttcagc ttccatttcg      1380 ccctcattt atccctcaac ccccagccca caggtgttta cagctcag cttttttgtct      1440 tttctgagga gaaacaaata agaccataaa gggaaaggat tcatgtggaa tataaagatg      1500
gctgactttg ctctttcttg actcttgttt tcagtttcaa ttcagtgctg tacttgatga      1560
cagacacttc taaatgaagt gcaaatttga tacatatgtg aatatggact cagttttctt      1620
gcagatcaaa tttcacgtcg tcttctgtat actgtggagg tacactctta tagaaagttc      1680
aaaaagtcta cgctctcctt tctttctaac tccagtgaag taatgggtc ctgctcaagt       1740 tgaaagagtc ctatttgcac tgtagcctcg ccgtctgtga attggaccat cctatttaac      1800
tggcttcagc ctccccacct tcttcagcca cctctcttt tcagttggct gacttccaca      1860
cctagcatct catgagtgcc aagcaaaagg agagaagaga gaaatagcct gcgctgtttt      1920
ttagtttggg ggttttgctg tttccttta tgagacccat tcctatttct tatagtcaat      1980
gtttctttta tcacgatatt attagtaaga aaacatcact gaaatgctag ctgcaagtga      2040
catctctttg atgtcatatg gaagagttaa aacaggtgga gaaattcctt gattcacaat      2100
gaaatgctct ccttccccct gcccccagac ctttatcca cttacctaga ttctacatat       2160
tctttaaatt tcatctcagg cctccctcaa ccccaccact tctttataa ctagtccttt       2220 actaatccaa cccatgatga gctcctcttc ctggcttctt actgaaaggt taccctgtaa      2280
catgcaattt tgcatttgaa taaagcctgc ttttaagtg ttaa                       2324
```

<210> SEQ ID NO 14
<211> LENGTH: 372
<212> TYPE: PRT
<213> ORGANISM: Homo sapiens

<400> SEQUENCE: 14

```
Met Ile Phe Pro Trp Lys Cys Gln Ser Thr Gln Arg Asp Leu Trp Asn
1               5                   10                  15

Ile Phe Lys Leu Trp Gly Trp Thr Met Leu Cys Cys Asp Phe Leu Ala
            20                  25                  30

His His Gly Thr Asp Cys Trp Thr Tyr His Tyr Ser Glu Lys Pro Met
        35                  40                  45

Asn Trp Gln Arg Ala Arg Arg Phe Cys Arg Asp Asn Tyr Thr Asp Leu
    50                  55                  60

Val Ala Ile Gln Asn Lys Ala Glu Ile Glu Tyr Leu Glu Lys Thr Leu
65                  70                  75                  80

Pro Phe Ser Arg Ser Tyr Tyr Trp Ile Gly Ile Arg Lys Ile Gly Gly
                85                  90                  95

Ile Trp Thr Trp Val Gly Thr Asn Lys Ser Leu Thr Glu Glu Ala Glu
            100                 105                 110

Asn Trp Gly Asp Gly Glu Pro Asn Asn Lys Lys Asn Lys Glu Asp Cys
        115                 120                 125

Val Glu Ile Tyr Ile Lys Arg Asn Lys Asp Ala Gly Lys Trp Asn Asp
    130                 135                 140

Asp Ala Cys His Lys Leu Lys Ala Ala Leu Cys Tyr Thr Ala Ser Cys
145                 150                 155                 160
```

```
Gln Pro Trp Ser Cys Ser Gly His Gly Glu Cys Val Glu Ile Ile Asn
                165                 170                 175
Asn Tyr Thr Cys Asn Cys Asp Val Gly Tyr Tyr Gly Pro Gln Cys Gln
            180                 185                 190
Phe Val Ile Gln Cys Glu Pro Leu Glu Ala Pro Glu Leu Gly Thr Met
        195                 200                 205
Asp Cys Thr His Pro Leu Gly Asn Phe Ser Ser Gln Cys Ala
    210                 215                 220
Phe Ser Cys Ser Glu Gly Thr Asn Leu Thr Gly Ile Glu Glu Thr Thr
225                 230                 235                 240
Cys Gly Pro Phe Gly Asn Trp Ser Ser Pro Glu Pro Thr Cys Gln Val
                245                 250                 255
Ile Gln Cys Glu Pro Leu Ser Ala Pro Asp Leu Gly Ile Met Asn Cys
            260                 265                 270
Ser His Pro Leu Ala Ser Phe Ser Phe Thr Ser Ala Cys Thr Phe Ile
        275                 280                 285
Cys Ser Glu Gly Thr Glu Leu Ile Gly Lys Lys Thr Ile Cys Glu
    290                 295                 300
Ser Ser Gly Ile Trp Ser Asn Pro Ser Pro Ile Cys Gln Lys Leu Asp
305                 310                 315                 320
Lys Ser Phe Ser Met Ile Lys Glu Gly Asp Tyr Asn Pro Leu Phe Ile
                325                 330                 335
Pro Val Ala Val Met Val Thr Ala Phe Ser Gly Leu Ala Phe Ile Ile
            340                 345                 350
Trp Leu Ala Arg Arg Leu Lys Lys Gly Lys Lys Ser Lys Arg Ser Met
        355                 360                 365
Asn Asp Pro Tyr
    370

<210> SEQ ID NO 15
<211> LENGTH: 2199
<212> TYPE: DNA
<213> ORGANISM: Mus musculus

<400> SEQUENCE: 15
gaattctcga gctcgtcgac cacgccctcc ttgtgcaaga actctgagcc ccaggtgcag      60
gaggctgagg cctgcagaga gacttgcaga gagacccagc aagccatggt gtttccatgg     120
agatgtgagg gtacttactg gggctcgagg aacatcctga agctgtgggt ctggacactg     180
ctctgttgtg acttcctgat acaccatgga actcactgtt ggacttacca ttattctgaa     240
aagcccatga ctgggaaaaa tgctagaaag ttctgcaagc aaaattacac agatttagtc     300
gccatacaaa acaagagaga aattgagtat ttagagaata cattgcccaa aagcccttat     360
tactactgga taggaatcag gaaaattggg aaaatgtgga catgggtggg aaccaacaaa     420
actctcacta agaagcaga gaactggggt gctgggagc ccaacaacaa gaagtccaag      480
gaggactgtg tggagatcta tatcaagagg gaacgagact ctgggaaatg gaacgatgac     540
gcctgtcaca acgaaaggc agctctctgc tacacagcct cttgccagcc agggtcttgc      600
aatggccgtg gagaatgtgt ggaaactatc aacaatcaca cgtgcatctg tgatgcaggg     660
tattacgggc ccagtgtca gtatgtggtc cagtgtgagc ctttggaggc ccctgagttg      720
ggtaccatgg actgcatcca ccccttggga aacttcagct ccagtccaa gtgtgctttc      780 aactgttctg agggaagaga gctacttggg actgcagaaa cacagtgtgg agcatctgga     840
aactggtcat ctccagagcc aatctgccaa gtggtccagt gtgagccttt ggaggcccct     900
```

-continued

```
gagttgggta ccatggactg catccacccc ttgggaaact tcagcttcca gtccaagtgt    960
gctttcaact gttctgaggg aagagagcta cttgggactg cagaaacaca gtgtggagca   1020
tctggaaact ggtcatctcc agagccaatc tgccaagaga caaacagaag tttctcaaag   1080
atcaaagaag gtgactacaa ccccctcttc attcctgtag ccgtcatggt caccgcattc   1140
tcggggctgg catttctcat ttggctggca aggcggttaa aaaaaggcaa gaaatctcaa   1200
gaaaggatgg atgatccata ctgattcatc ctttgtgaaa ggaaagccat gaagtgctaa   1260
agacaaaaca ttggaaaata acgtcaagtc ctcccgtgaa gattttacac gcaggcatct   1320
cccacattag agatgcagtg tttgctcaac gaatctggaa ggatttcttc atgaccaaca   1380
gctcctccta atttcccctc gctcattcat cccattaacc ctatcccata atgtgtgtct   1440
atacagagta gtattttatc atcttttctg tggaggaaca agcaaaagtg ttactgtaga   1500
atataaagac agctgctttt actctttcct aactcttgtt tcctagttca attcagcaca   1560
gaagctaatg ccaaacacag tgaaaatatg atccatgagt aattggaaac tcagactcct   1620
tgcgcatagt acgtacccta tgtaacatcg acaaaaatct ttcatttcca cctccaaaga   1680
acagtgctct attcaagttg ggaaagtcct acttcctctg tagacccact atctgtgagt   1740
gacagccact gtagctgttc acattaacct tccccatctc cttttcctag gagaataatt   1800
ccacacactg caccccatga tggccaccaa acatcaaaga agggaaaatc tcctgcattg   1860
agttttagtt ttgagttttc ccttctcttt attagatctc tgatggttcc ttgaagtcag   1920
tgttctgatg attattaata gttaatgata acacaaccca ctctcttgga gctgatgtta   1980
tgaagacaac aggtagaaaa attcctgggc tcaggctgga gtgacaccct tttctttccc   2040
taacatcttc tactcagata cctaaattta agattcagga cagctgtccc caactcttac   2100
catgtctttt ataacttgct ccttaacttg cccaacctgt aggctatctc attttctcgc   2160
ttcactctgc aaggtttata acatgatgaa tttaaatac                          2199
```

<210> SEQ ID NO 16
<211> LENGTH: 372
<212> TYPE: PRT
<213> ORGANISM: Mus musculus

<400> SEQUENCE: 16

```
Met Val Phe Pro Trp Arg Cys Glu Gly Thr Tyr Trp Gly Ser Arg Asn
  1               5                  10                  15

Ile Leu Lys Leu Trp Val Trp Thr Leu Leu Cys Cys Asp Phe Leu Ile
             20                  25                  30

His His Gly Thr His Cys Trp Thr Tyr His Tyr Ser Glu Lys Pro Met
         35                  40                  45

Asn Trp Glu Asn Ala Arg Lys Phe Cys Lys Gln Asn Tyr Thr Asp Leu
     50                  55                  60

Val Ala Ile Gln Asn Lys Arg Glu Ile Glu Tyr Leu Glu Asn Thr Leu
 65                  70                  75                  80

Pro Lys Ser Pro Tyr Tyr Tyr Trp Ile Gly Ile Arg Lys Ile Gly Lys
                 85                  90                  95

Met Trp Thr Trp Val Gly Thr Asn Lys Thr Leu Thr Lys Glu Ala Glu
            100                 105                 110

Asn Trp Gly Ala Gly Glu Pro Asn Asn Lys Ser Lys Glu Asp Cys
        115                 120                 125

Val Glu Ile Tyr Ile Lys Arg Glu Arg Asp Ser Gly Lys Trp Asn Asp
    130                 135                 140
```

Asp Ala Cys His Lys Arg Lys Ala Ala Leu Cys Tyr Thr Ala Ser Cys
145                 150                 155                 160

Gln Pro Gly Ser Cys Asn Gly Arg Gly Glu Cys Val Glu Thr Ile Asn
            165                 170                 175

Asn His Thr Cys Ile Cys Asp Ala Gly Tyr Tyr Gly Pro Gln Cys Gln
        180                 185                 190

Tyr Val Val Gln Cys Glu Pro Leu Glu Ala Pro Glu Leu Gly Thr Met
    195                 200                 205

Asp Cys Ile His Pro Leu Gly Asn Phe Ser Phe Gln Ser Lys Cys Ala
210                 215                 220

Phe Asn Cys Ser Glu Gly Arg Glu Leu Leu Gly Thr Ala Glu Thr Gln
225                 230                 235                 240

Cys Gly Ala Ser Gly Asn Trp Ser Ser Pro Glu Pro Ile Cys Gln Val
            245                 250                 255

Val Gln Cys Glu Pro Leu Glu Ala Pro Glu Leu Gly Thr Met Asp Cys
        260                 265                 270

Ile His Pro Leu Gly Asn Phe Ser Phe Gln Ser Lys Cys Ala Phe Asn
    275                 280                 285

Cys Ser Glu Gly Arg Glu Leu Leu Gly Thr Ala Glu Thr Gln Cys Gly
290                 295                 300

Ala Ser Gly Asn Trp Ser Ser Pro Glu Pro Ile Cys Gln Glu Thr Asn
305                 310                 315                 320

Arg Ser Phe Ser Lys Ile Lys Glu Gly Asp Tyr Asn Pro Leu Phe Ile
            325                 330                 335

Pro Val Ala Val Met Val Thr Ala Phe Ser Gly Leu Ala Phe Leu Ile
        340                 345                 350

Trp Leu Ala Arg Arg Leu Lys Lys Gly Lys Lys Ser Gln Glu Arg Met
    355                 360                 365

Asp Asp Pro Tyr
    370

<210> SEQ ID NO 17
<211> LENGTH: 2041
<212> TYPE: DNA
<213> ORGANISM: Homo sapiens

<400> SEQUENCE: 17
gccacttctt ctgggcccac gaggcagctg tcccatgctc tgctgagcac ggtggtgcca      60
tgcctctgca actcctcctg ttgctgatcc tactgggccc tggcaacagc ttgcagctgt     120
gggacacctg gcagatgaa gccgagaaag ccttgggtcc cctgcttgcc cgggaccgga     180
gacaggccac cgaatatgag tacctagatt atgatttcct gccagaaacg gagcctccag     240
aaatgctgag gaacagcact gacaccactc ctctgactgg gcctggaacc cctgagtcta     300
ccactgtgga gcctgctgca aggcgttcta ctggcctgga tgcaggaggg gcagtcacag     360
agctgaccac ggagctggcc aacatgggga acctgtccac ggattcagca gctatggaga     420
tacagaccac tcaaccagca gccacggagg cacagaccac tccactggca gccacagagg     480
cacagacaac tcgactgacg gccacggagg cacagaccac tccactggca gccacagagg     540
cacagaccac tccaccagca gccacggaag cacagaccac tcaacccaca ggcctggagg     600
cacagaccac tgcaccagca gccatggagg cacagaccac tgcaccagca gccatggaag     660
cacagaccac tccaccagca gccatggagg cacagaccac tcaaaccaca gccatggagg     720
cacagaccac tgcaccagaa gccacggagg cacagaccac tcaacccaca gccacggagg     780
cacagaccac tccactggca gccatggagg ccctgtccac agaacccagt gccacagagg     840

```
cctgtccat ggaacctact accaaaagag gtctgttcat acccttttct gtgtcctctg     900
ttactcacaa gggcattccc atggcagcca gcaatttgtc cgtcaactac ccagtggggg    960
ccccagacca catctctgtg aagcagtgcc tgctggccat cctaatcttg gcgctggtgg   1020
ccactatctt cttcgtgtgc actgtggtgc tggcggtccg cctctcccgc aagggccaca   1080
tgtaccccgt gcgtaattac tcccccaccg agatggtctg catctcatcc ctgttgcctg   1140
atggggtga ggggccctct gccacagcca atggggcct gtccaaggcc aagagcccgg     1200
gcctgacgcc agagcccagg gaggaccgtg aggggggatga cctcaccctg cacagcttcc  1260
tcccttagct cactctgcca tctgttttgg caagacccca cctccacggg ctctcctggg   1320
ccaccctga gtgcccagac cccaatccac agctctgggc ttcctcggag accctgggg     1380
atgggatct tcagggaagg aactctggcc acccaaacag gacaagagca gcctggggcc   1440
aagcagacgg gcaagtggag ccacctcttt cctccctccg cggatgaagc ccagccacat   1500
ttcagccgag gtccaaggca ggaggccatt tacttgagac agattctctc cttttttcctg  1560
tcccccatct tctctgggtc cctctaacat ctcccatggc tctccccgct tctcctggtc   1620
actggagtct cctccccatg tacccaagga agatggagct cccccatccc acacgcactg   1680
cactgccatt gtcttttggt tgccatggtc accaaacagg aagtggacat tctaagggag   1740
gagtactgaa gagtgacgga cttctgaggc tgtttcctgc tgctcctctg acttggggca   1800
gcttgggtct tcttgggcac ctctctggga aaacccaggg tgaggttcag cctgtgaggg   1860
ctgggatggg tttcgtgggc ccaaagggca gacctttctt tgggactgtg tggaccaagg   1920
agcttccatc tagtgacaag tgaccccag ctatcgcctc ttgccttccc ctgtggccac    1980
tttccagggt ggactctgtc ttgttcactg cagtatccca actgcaggtc cagtgcaggc   2040
a                                                                    2041
```

<210> SEQ ID NO 18
<211> LENGTH: 402
<212> TYPE: PRT
<213> ORGANISM: Homo sapiens

<400> SEQUENCE: 18

```
Met Pro Leu Gln Leu Leu Leu Leu Ile Leu Leu Gly Pro Gly Asn
1               5                   10                  15

Ser Leu Gln Leu Trp Asp Thr Trp Ala Asp Glu Ala Glu Lys Ala Leu
            20                  25                  30

Gly Pro Leu Ala Arg Asp Arg Arg Gln Ala Thr Glu Tyr Glu Tyr
        35                  40                  45

Leu Asp Tyr Asp Phe Leu Pro Glu Thr Glu Pro Pro Glu Met Leu Arg
    50                  55                  60

Asn Ser Thr Asp Thr Thr Pro Leu Thr Gly Pro Gly Thr Pro Glu Ser
65                  70                  75                  80

Thr Thr Val Glu Pro Ala Ala Arg Arg Ser Thr Gly Leu Asp Ala Gly
                85                  90                  95

Gly Ala Val Thr Glu Leu Thr Thr Glu Leu Ala Asn Met Gly Asn Leu
            100                 105                 110

Ser Thr Asp Ser Ala Ala Met Glu Ile Gln Thr Thr Gln Pro Ala Ala
        115                 120                 125

Thr Glu Ala Gln Thr Thr Pro Leu Ala Ala Thr Glu Ala Gln Thr Thr
    130                 135                 140

Arg Leu Thr Ala Thr Glu Ala Gln Thr Thr Pro Leu Ala Ala Thr Glu
145                 150                 155                 160
```

Ala Gln Thr Thr Pro Ala Ala Thr Glu Ala Gln Thr Thr Gln Pro
            165                 170                 175

Thr Gly Leu Glu Ala Gln Thr Thr Ala Pro Ala Ala Met Glu Ala Gln
        180                 185                 190

Thr Thr Ala Pro Ala Ala Met Glu Ala Gln Thr Thr Pro Pro Ala Ala
            195                 200                 205

Met Glu Ala Gln Thr Thr Gln Thr Thr Ala Met Glu Ala Gln Thr Thr
210                 215                 220

Ala Pro Glu Ala Thr Glu Ala Gln Thr Gln Pro Thr Ala Thr Glu
225                 230                 235                 240

Ala Gln Thr Thr Pro Leu Ala Ala Met Glu Ala Leu Ser Thr Glu Pro
            245                 250                 255

Ser Ala Thr Glu Ala Leu Ser Met Glu Pro Thr Thr Lys Arg Gly Leu
        260                 265                 270

Phe Ile Pro Phe Ser Val Ser Ser Val Thr His Lys Gly Ile Pro Met
    275                 280                 285

Ala Ala Ser Asn Leu Ser Val Asn Tyr Pro Val Gly Ala Pro Asp His
        290                 295                 300

Ile Ser Val Lys Gln Cys Leu Leu Ala Ile Leu Ile Leu Ala Leu Val
305                 310                 315                 320

Ala Thr Ile Phe Phe Val Cys Thr Val Val Leu Ala Val Arg Leu Ser
            325                 330                 335

Arg Lys Gly His Met Tyr Pro Val Arg Asn Tyr Ser Pro Thr Glu Met
            340                 345                 350

Val Cys Ile Ser Ser Leu Leu Pro Asp Gly Gly Glu Gly Pro Ser Ala
        355                 360                 365

Thr Ala Asn Gly Gly Leu Ser Lys Ala Lys Ser Pro Gly Leu Thr Pro
        370                 375                 380

Glu Pro Arg Glu Asp Arg Glu Gly Asp Asp Leu Thr Leu His Ser Phe
385                 390                 395                 400

Leu Pro

<210> SEQ ID NO 19
<211> LENGTH: 1734
<212> TYPE: DNA
<213> ORGANISM: Mus musculus

<400> SEQUENCE: 19

```
gcagtgtgga ctggggccct gtcactgagg cagagtcgtt tgcttctggg ccccgaggca    60
gctgccccat gctctgttgg gcacggtacc atgtccccaa gcttccttgt gctgctgacc   120
atcttgggcc ctggcaacag ccttcagctg caggacccct gggggcatga accaaggaa    180
gccccgggtc ctgtgcatct ccgggaacgg aggcaggtgg ttggggatga cgattttgag   240
gaccctgact atacgtataa cacagacccc ccagaattgc tgaaaaatgt caccaacacc   300
gtggctgctc accctgagct gccaaccacc gtggtcatgc tagagagaga ttccacgagc   360
gctggaacct ccgagagagc cactgagaag attgccacca ctgaccctac tgccccaggt   420
acaggaggga cagctgttgg gatgctgagc acagactctg ccacacagtg gagtctaacc   480
tcagtagaga ccgtccaacc agcatccaca gaggtagaga cctcgcagcc aacacccatg   540
gaggcagaca cctcaaagcc agcacccatg gaggcagaga cctcgcagcc agcacccatg   600
gaggcagaga cctcgcagcc agcacccatg gaggcagaga cctcgcagcc agcacccatg   660
gaggcagaga cctctcagcc agcacccaac gaggcagaga cctcaaaacc agcacccacg   720
```

| | |
|---|---|
| gaggcagaga cctcaaaacc agcacccacg gaggcagaga ccacccagct tcccaggatt | 780 |
| caggctgtaa aaactctgtt tacaacgtct gcagccaccg aagtcccttc cacagaacct | 840 |
| accaccatgg agacggcgtc cacagagtct aacgagtcta ccatcttcct tgggccatcc | 900 |
| gtgactcact tacctgacag cggcctgaag aaagggctga ttgtgacccc tgggagttca | 960 |
| cctgccccaa ccctgccagg gagttcagat ctcatcccgg tgaagcaatg tctgctgatt | 1020 |
| atcctcatct tggcttctct ggccaccatc ttcctcgtgt gcacagtggt gctggcggtc | 1080 |
| cgtctgtccc gtaagaccca catgtaccca gtgcggaact actcccccac ggagatgatc | 1140 |
| tgcatctcgt ccctgctacc tgagggggga cgggggccc ctgtcacagc caatgggggc | 1200 |
| ctgcccaagg tccaggacct gaagacagag cccagtgggg accgggatgg ggacgacctc | 1260 |
| accctgcaca gcttcctccc ttagactccc ctgcccgccc acctaagcga gacctttgct | 1320 |
| agctccactc tcacccgctg gtcacggagg tcatagatct gggcttcctg ggtgaaatgt | 1380 |
| attcacggga gtctttagag cgcccaccgc tgtgtgtctc cctgcaggtc actggatacc | 1440 |
| tgtccttgcg ttctccagaa agactcagct cccttattcc actcccaaaa gctactctgt | 1500 |
| tggttgccat ggtaacccgg taagagagga gctttgtggg aggccgccat gtctgcttct | 1560 |
| ctgattccag tggcaggtag ctcggctttc ccaggtccct ggcttggagg gatggtcctt | 1620 |
| cctttgggcc cgtgtgaacc aacgagtttc cgtacagtga cagaatgacc tcgcgctgcg | 1680 |
| gcctggccca gcacaggcat ccaataaaca tattataata aaaaaaaaaa aaaa | 1734 |

<210> SEQ ID NO 20
<211> LENGTH: 397
<212> TYPE: PRT
<213> ORGANISM: Mus musculus

<400> SEQUENCE: 20

```
Met Ser Pro Ser Phe Leu Val Leu Thr Ile Leu Gly Pro Gly Asn
1               5                   10                  15

Ser Leu Gln Leu Gln Asp Pro Trp Gly His Glu Thr Lys Glu Ala Pro
            20                  25                  30

Gly Pro Val His Leu Arg Glu Arg Arg Gln Val Val Gly Asp Asp Asp
        35                  40                  45

Phe Glu Asp Pro Asp Tyr Thr Tyr Asn Thr Asp Pro Pro Glu Leu Leu
    50                  55                  60

Lys Asn Val Thr Asn Thr Val Ala Ala His Pro Glu Leu Pro Thr Thr
65                  70                  75                  80

Val Val Met Leu Glu Arg Asp Ser Thr Ser Ala Gly Thr Ser Glu Arg
                85                  90                  95

Ala Thr Glu Lys Ile Ala Thr Thr Asp Pro Thr Ala Pro Gly Thr Gly
            100                 105                 110

Gly Thr Ala Val Gly Met Leu Ser Thr Asp Ser Ala Thr Gln Trp Ser
        115                 120                 125

Leu Thr Ser Val Glu Thr Val Gln Pro Ala Ser Thr Glu Val Glu Thr
    130                 135                 140

Ser Gln Pro Thr Pro Met Glu Ala Asp Thr Ser Lys Pro Ala Pro Met
145                 150                 155                 160

Glu Ala Glu Thr Ser Gln Pro Ala Pro Met Glu Ala Glu Thr Ser Gln
                165                 170                 175

Pro Ala Pro Met Glu Ala Glu Thr Ser Gln Pro Ala Pro Met Glu Ala
            180                 185                 190

Glu Thr Ser Gln Pro Ala Pro Asn Glu Ala Glu Thr Ser Lys Pro Ala
        195                 200                 205
```

Pro Thr Glu Ala Glu Thr Ser Lys Pro Ala Pro Thr Glu Ala Glu Thr
    210                 215                 220
Thr Gln Leu Pro Arg Ile Gln Ala Val Lys Thr Leu Phe Thr Thr Ser
225                 230                 235                 240
Ala Ala Thr Glu Val Pro Ser Thr Glu Pro Thr Thr Met Glu Thr Ala
                245                 250                 255
Ser Thr Glu Ser Asn Glu Ser Thr Ile Phe Leu Gly Pro Ser Val Thr
            260                 265                 270
His Leu Pro Asp Ser Gly Leu Lys Lys Gly Leu Ile Val Thr Pro Gly
        275                 280                 285
Ser Ser Pro Ala Pro Thr Leu Pro Gly Ser Ser Asp Leu Ile Pro Val
    290                 295                 300
Lys Gln Cys Leu Leu Ile Ile Leu Ile Leu Ala Ser Leu Ala Thr Ile
305                 310                 315                 320
Phe Leu Val Cys Thr Val Val Leu Ala Val Arg Leu Ser Arg Lys Thr
                325                 330                 335
His Met Tyr Pro Val Arg Asn Tyr Ser Pro Thr Glu Met Ile Cys Ile
            340                 345                 350
Ser Ser Leu Leu Pro Glu Gly Gly Asp Gly Ala Pro Val Thr Ala Asn
        355                 360                 365
Gly Gly Leu Pro Lys Val Gln Asp Leu Lys Thr Glu Pro Ser Gly Asp
    370                 375                 380
Arg Asp Gly Asp Asp Leu Thr Leu His Ser Phe Leu Pro
385                 390                 395

<210> SEQ ID NO 21
<211> LENGTH: 1910
<212> TYPE: DNA
<213> ORGANISM: Homo sapiens

<400> SEQUENCE: 21
cttccccggc tggggcggct ggagagccgg gagtcgctgg gtgcgtgggg ctgcctcgcc      60
gcgtctcgcc acgggctctg ccagcagaca gccttggcac acaggcacaa gggctggagc     120
ccagagatga gagtgcccaa gggagatgtg agcctggcgg gctgcccgct aacctgtcgc     180
tgaagcccca gaagcgggcc ctcaggccag gcctaccctg cctccggccc agcatgcgcc     240
tgtcggtgcg gagggtgctg ctggcagccg gctgcgccct ggtcctggtg ctggcggttc     300
agctgggaca gcaggtgcta gagtgccggg cggtgctggc gggcctgcgg agccccggg     360
gggccatgcg gcctgagcag gaggagctgg tgatggtggg caccaaccac gtggaatacc     420
gctatggcaa ggccatgccg ctcatcttcg tgggtggcgt gcctcgcagt ggcaccacgt     480
tgatgcgcgc catgctggac gcgcaccccg aggtgcgctg cggcgaggag acccgcatca     540
tcccgcgcgt gctggccatg cgccaggcct ggtccaagtc tggccgtgag aagctgcggc     600
tggatgaggc gggggtgacg gatgaggtgc tggacgccgc catgcaggcc ttcatcctgg     660
aggtgattgc caagcacgga gagccggccc gcgtgctctg caacaaggac ccatttacgc     720
tcaagtcctc ggtctacctg tcgcgcctgt tccccaactc caagttcctg ctgatggtgc     780
gggacggccg ggcctccgtg cactccatga tcacgcgcaa agtcaccatt gcgggctttg     840
acctcagcag ctaccgtgac tgcctcacca agtggaacaa ggccatcgag gtgatgtacg     900
cccagtgcat ggaggtaggc aaggagaagt gcctgcctgt gtactacgag cagctggtgc     960
tgcaccccag gcgctcactc aagctcatcc tcgacttcct cggcatcgcc tggagcgacg    1020
ctgtcctcca ccatgaagac ctcattggca agcccggtgg tgtctccctg tccaagatcg    1080

```
agcggtccac ggaccaggtc atcaagcctg ttaacctgga agcgctctcc aagtggactg    1140
gccacatccc tggggatgtg gtgcgggaca tggcccagat cgcccccatg ctggctcagc    1200
tcggctatga cccttatgca aaccccccca actatggcaa ccctgacccc ttcgtcatca    1260
acaacacaca gcgggtcttg aaaggggact ataaaacacc agccaatctg aaaggatatt    1320
ttcaggtgaa ccagaacagc acctcctccc acttaggaag ctcgtgattt ccagatctcc    1380
gcaaatgact tcattgccaa gaagagaaga aaatgcattt aagtggaaat cggacctcta    1440
atccaagcat attgcttgct attaatcgcc aaaacaggac tgctgatgag gaatgtatt t    1500 gcatatgttt gcaaaagctg aatcattgaa acgtaccttt gaaactctct atctctggac    1560
actccagggt agagaatgaa gggtatgaa gtagtccggc ttttgaaact taggtatttt    1620
atatttttcc cctcaagaac ttttttttaa gagacagatt tgccatcctc cttaatttgc    1680
aggactgcct tggtggcttt gtttgctggg acaaggccca caacctgtgc ctctcctatt    1740
gacccttact ttgaattcaa agaatctatt taagagttta atatatgagg ctttctttga    1800
ttcctcctca gttctaccta gtttcacaga ggaaaaaaat actctttgaa taaagtgaac    1860
agaggctcat ttgtttgtgc cttactttac tgaaaaaaaa aaaaaaaaaa                1910
```

<210> SEQ ID NO 22
<211> LENGTH: 377
<212> TYPE: PRT
<213> ORGANISM: Homo sapiens

<400> SEQUENCE: 22

```
Met Arg Leu Ser Val Arg Arg Val Leu Leu Ala Ala Gly Cys Ala Leu
1               5                   10                  15

Val Leu Val Leu Ala Val Gln Leu Gly Gln Gln Val Leu Glu Cys Arg
            20                  25                  30

Ala Val Leu Ala Gly Leu Arg Ser Pro Arg Gly Ala Met Arg Pro Glu
        35                  40                  45

Gln Glu Glu Leu Val Met Val Gly Thr Asn His Val Glu Tyr Arg Tyr
    50                  55                  60

Gly Lys Ala Met Pro Leu Ile Phe Val Gly Val Pro Arg Ser Gly
65                  70                  75                  80

Thr Thr Leu Met Arg Ala Met Leu Asp Ala His Pro Glu Val Arg Cys
                85                  90                  95

Gly Glu Glu Thr Arg Ile Ile Pro Arg Val Leu Ala Met Arg Gln Ala
            100                 105                 110

Trp Ser Lys Ser Gly Arg Glu Lys Leu Arg Leu Asp Glu Ala Gly Val
        115                 120                 125

Thr Asp Glu Val Leu Asp Ala Ala Met Gln Ala Phe Ile Leu Glu Val
    130                 135                 140

Ile Ala Lys His Gly Glu Pro Ala Arg Val Leu Cys Asn Lys Asp Pro
145                 150                 155                 160

Phe Thr Leu Lys Ser Ser Val Tyr Leu Ser Arg Leu Phe Pro Asn Ser
                165                 170                 175

Lys Phe Leu Leu Met Val Arg Asp Gly Arg Ala Ser Val His Ser Met
            180                 185                 190

Ile Thr Arg Lys Val Thr Ile Ala Gly Phe Asp Leu Ser Ser Tyr Arg
        195                 200                 205

Asp Cys Leu Thr Lys Trp Asn Lys Ala Ile Glu Val Met Tyr Ala Gln
    210                 215                 220

Cys Met Glu Val Gly Lys Glu Lys Cys Leu Pro Val Tyr Tyr Glu Gln
```

```
                225                 230                 235                 240
Leu Val Leu His Pro Arg Arg Ser Leu Lys Leu Ile Leu Asp Phe Leu
                245                 250                 255

Gly Ile Ala Trp Ser Asp Ala Val Leu His His Glu Asp Leu Ile Gly
            260                 265                 270

Lys Pro Gly Gly Val Ser Leu Ser Lys Ile Glu Arg Ser Thr Asp Gln
        275                 280                 285

Val Ile Lys Pro Val Asn Leu Glu Ala Leu Ser Lys Trp Thr Gly His
    290                 295                 300

Ile Pro Gly Asp Val Val Arg Asp Met Ala Gln Ile Ala Pro Met Leu
305                 310                 315                 320

Ala Gln Leu Gly Tyr Asp Pro Tyr Ala Asn Pro Asn Tyr Gly Asn
                325                 330                 335

Pro Asp Pro Phe Val Ile Asn Asn Thr Gln Arg Val Leu Lys Gly Asp
            340                 345                 350

Tyr Lys Thr Pro Ala Asn Leu Lys Gly Tyr Phe Gln Val Asn Gln Asn
        355                 360                 365

Ser Thr Ser Ser His Leu Gly Ser Ser
    370                 375

<210> SEQ ID NO 23
<211> LENGTH: 1829
<212> TYPE: DNA
<213> ORGANISM: Mus musculus

<400> SEQUENCE: 23
cccacgcgtc cggccggcag ggagccggag tctgcgcggg cgccgatttg gcacggact      60 gtcagggcag gaagccgtgg tgaccaggct cgaggactgg cgcttgaaaa tgagggcgcc     120
caggggagat gtataccagg tgggcctgct gacccgtcca tgaggcgggc ccctggctg     180 ggcctgcgac cctggctggg catgcgcctg tcggtgcgta aggtgctgct ggccgccggc    240
tgtgctctgg ccctggtgct cgctgtgcag cttgggcagc aagtactgga gtgccgggcg    300
gtgctcgggg gcacacggaa cccacggagg atgcggccgg agcaggagga actggtgatg    360
ctcggcgccg accacgtgga gtaccgctat ggcaaggcca tgccactcat ctttgtgggc    420
ggcgtgccac gcagtggcac cacgctcatg cgcgccatgt ggacgcacac cccggaggtg    480
cgctgtgggg aggagacgcg catcatccct cgtgtgctgg ccatgcggca ggcctggacc    540
aagtctggcc gtgagaagct gcggctggac gaggcaggtg tgacggatga ggtgctggac    600
gcggccatgc aggccttcat tctggaggtg atcgccaagc acggcgaacc agcccgcgtg    660
ctgtgtaaca aggaccccct tcacactcaag tcatccgtct acctggcacg cctgttcccc    720
aactccaaat tcctgctaat ggtgcgtgac ggccgggcgt ccgtgcactc catgatcacg    780
cgcaaggtca ccatcgcggg cttgacctc agcagctacc gagactgcct caccaagtgg    840
aacaaggcca tcgaggtgat gtacgcacag tgcatggagg tgggcaggga caagtgcctg    900
cccgtgtact atgagcagtt ggtgctgcac ccccggcgct cactcaaacg catcctggat    960
ttcctgggca tcgcctggag tgacacagtc ctgcaccatg aggacctcat tggcaagcct   1020
gggggcgtct ccttgtccaa gatcgagcgg tccacggacc aggtcatcaa accggtgaac   1080
ttggaagctc tctccaagtg gacgggccac atccctagag acgtggtgag ggatatggcc   1140
cagattgccc ccatgctggc ccggcttggc tatgacccgt atgcgaatcc gcccaactat   1200
gggaaccccg accccattgt catcaacaac acacaccggg tcttgaaagg agactataaa   1260
acgccagcca atctgaaagg atattttcag gtgaaccaga acagcacctc cccacaccta   1320
```

-continued

```
ggaagttcgt gatttccagt ccctgcaggg ctcagacgcc tcagtcctcg acctgcacac    1380
ggaagctgga ctaacccaag cacatggctt gctctcagtc acgccgggcg gggcctgccg    1440
ggttggagca ttcatacatc ttggccaaag caggcttgga acctccgctc caggacaaca    1500
ctaaggaggg agagactact tccgcttcag aaacttggag attttctaat ttttctctcc    1560
ttggaacttt ttttaaaga attgaattg ctatcttccc taatggacag accccttggt    1620
gacctcatct cctgggacaa gaccggagac ccgtgcctct ccttgactgg acgttgaact    1680
caaaggatct atttaagagt ttaatatatg ggttctcctt gctctagtcc tactcagttt    1740
cacagagaaa agaaattaat tatttgaata aagtagacag gctgctgtct gtgccttact    1800
tcaaaaaaaa aaaaaaaaa aaaaaaaa                                        1829
```

<210> SEQ ID NO 24
<211> LENGTH: 376
<212> TYPE: PRT
<213> ORGANISM: Mus musculus

<400> SEQUENCE: 24

```
Met Arg Leu Ser Val Arg Lys Val Leu Leu Ala Gly Cys Ala Leu
1               5                   10                  15

Ala Leu Val Leu Ala Val Gln Leu Gly Gln Gln Val Leu Glu Cys Arg
            20                  25                  30

Ala Val Leu Gly Gly Thr Arg Asn Pro Arg Arg Met Arg Pro Glu Gln
            35                  40                  45

Glu Glu Leu Val Met Leu Gly Ala Asp His Val Glu Tyr Arg Tyr Gly
50                  55                  60

Lys Ala Met Pro Leu Ile Phe Val Gly Val Pro Arg Ser Gly Thr
65              70                  75                  80

Thr Leu Met Arg Ala Met Leu Asp Ala His Pro Glu Val Arg Cys Gly
                85                  90                  95

Glu Glu Thr Arg Ile Ile Pro Arg Val Leu Ala Met Arg Gln Ala Trp
            100                 105                 110

Thr Lys Ser Gly Arg Glu Lys Leu Arg Leu Asp Glu Ala Gly Val Thr
            115                 120                 125

Asp Glu Val Leu Asp Ala Ala Met Gln Ala Phe Ile Leu Glu Val Ile
130                 135                 140

Ala Lys His Gly Glu Pro Ala Arg Val Leu Cys Asn Lys Asp Pro Phe
145                 150                 155                 160

Thr Leu Lys Ser Ser Val Tyr Leu Ala Arg Leu Phe Pro Asn Ser Lys
                165                 170                 175

Phe Leu Leu Met Val Arg Asp Gly Arg Ala Ser Val His Ser Met Ile
            180                 185                 190

Thr Arg Lys Val Thr Ile Ala Gly Phe Asp Leu Ser Ser Tyr Arg Asp
            195                 200                 205

Cys Leu Thr Lys Trp Asn Lys Ala Ile Glu Val Met Tyr Ala Gln Cys
210                 215                 220

Met Glu Val Gly Arg Asp Lys Cys Leu Pro Val Tyr Tyr Glu Gln Leu
225                 230                 235                 240

Val Leu His Pro Arg Arg Ser Leu Lys Arg Ile Leu Asp Phe Leu Gly
                245                 250                 255

Ile Ala Trp Ser Asp Thr Val Leu His His Glu Asp Leu Ile Gly Lys
            260                 265                 270

Pro Gly Gly Val Ser Leu Ser Lys Ile Glu Arg Ser Thr Asp Gln Val
            275                 280                 285
```

```
Ile Lys Pro Val Asn Leu Glu Ala Leu Ser Lys Trp Thr Gly His Ile
    290                 295                 300

Pro Arg Asp Val Val Arg Asp Met Ala Gln Ile Ala Pro Met Leu Ala
305                 310                 315                 320

Arg Leu Gly Tyr Asp Pro Tyr Ala Asn Pro Pro Asn Tyr Gly Asn Pro
                325                 330                 335

Asp Pro Ile Val Ile Asn Asn Thr His Arg Val Leu Lys Gly Asp Tyr
            340                 345                 350

Lys Thr Pro Ala Asn Leu Lys Gly Tyr Phe Gln Val Asn Gln Asn Ser
        355                 360                 365

Thr Ser Pro His Leu Gly Ser Ser
    370                 375

<210> SEQ ID NO 25
<211> LENGTH: 1670
<212> TYPE: DNA
<213> ORGANISM: Homo sapiens

<400> SEQUENCE: 25
ccaaccacaa gcaccaaagc agaggggcag gcagcacacc acccagcagc cagagcacca      60
gcccagccat ggtccttgag gtgagtgacc accaagtgct aaatgacgcc gaggttgccg     120
ccctcctgga gaacttcagc tcttcctatg actatggaga aaacgagagt gactcgtgct     180
gtacctcccc gccctgccca caggacttca gcctgaactt cgaccgggcc ttcctgccag     240
ccctctacag cctcctcttt ctgctggggc tgctgggcaa cggcgcggtg gcagccgtgc     300
tgctgagccg gcggacagcc ctgagcagca ccgacacctt cctgctccac ctagctgtag     360
cagacacgct gctggtgctg acactgccgc tctgggcagt ggacgctgcc gtccagtggg     420
tctttggctc tggcctctgc aaagtggcag gtgccctctt caacatcaac ttctacgcag     480
gagccctcct gctggcctgc atcagctttg accgctacct gaacatagtt catgccaccc     540
agctctaccg ccgggggccc cggcccgcg tgaccctcac ctgcctggct gtctggggc      600 tctgcctgct tttcgccctc cagacttca tcttcctgtc ggcccaccac gacgagcgcc     660
tcaacgccac ccactgccaa tacaacttcc acaggtgggg ccgcacggct ctgcgggtgc     720
tgcagctggt ggctggcttt ctgctgcccc tgctggtcat ggcctactgc tatgcccaca     780
tcctggccgt gctgctggtt ccaggggcc agcggcgcct gcgggccatg cggctggtgg     840
tggtggtcgt ggtggccttt gccctctgct ggacccccta tcacctggtg gtgctggtgg     900
acatcctcat ggaccctggg gctttggccc gcaactgtgg ccgagaaagc agggtagacg     960
tggccaagtc ggtcacctca ggcctgggct acatgcactg ctgcctcaac ccgctgctct    1020
atgcctttgt aggggtcaag ttccgggagc ggatgtggat gctgctcttg cgcctgggct    1080
gccccaacca gagagggctc cagaggcagc atcgtcttc ccgccgggat tcatcctggt    1140
ctgagacctc agaggcctcc tactcgggct tgtgaggccg gaatccgggc tccccttcg     1200 cccacagtct gacttccccg cattccaggc tcctccctcc ctctgccggc tctggctctc    1260
cccaatatcc tcgctcccgg gactcactgg cagccccagc accaccaggt ctcccgggaa    1320
gccaccctcc cagctctgag gactgcacca ttgctgctcc ttagctgcca agccccatcc    1380
tgccgcccga ggtggctgcc tggagcccca ctgcccttct catttggaaa ctaaaacttc    1440
atcttcccca gtgcggggga gtacaaggca tggcgtagag ggtgctgccc catgaagcca    1500
cagcccaggc ctccagctca gcagtgactg tggccatggt ccccaagacc tctatatttg    1560 ctctttttatt tttatgtcta aaatcctgct taaaactttt caataaacaa gatcgtcagg    1620
```
accaaaaaaa aaaaaaaaaa aaaaaaaaaa aaaaaaaaaa aaaaaaaaaa    1670

<210> SEQ ID NO 26
<211> LENGTH: 368
<212> TYPE: PRT
<213> ORGANISM: Homo sapiens

<400> SEQUENCE: 26

Met Val Leu Glu Val Ser Asp His Gln Val Leu Asn Asp Ala Glu Val
1               5                   10                  15

Ala Ala Leu Leu Glu Asn Phe Ser Ser Tyr Asp Tyr Gly Glu Asn
            20                  25                  30

Glu Ser Asp Ser Cys Cys Thr Ser Pro Pro Cys Pro Gln Asp Phe Ser
            35                  40                  45

Leu Asn Phe Asp Arg Ala Phe Leu Pro Ala Leu Tyr Ser Leu Leu Phe
        50                  55                  60

Leu Leu Gly Leu Leu Gly Asn Gly Ala Val Ala Ala Val Leu Leu Ser
65                  70                  75                  80

Arg Arg Thr Ala Leu Ser Ser Thr Asp Thr Phe Leu Leu His Leu Ala
                85                  90                  95

Val Ala Asp Thr Leu Leu Val Leu Thr Leu Pro Leu Trp Ala Val Asp
            100                 105                 110

Ala Ala Val Gln Trp Val Phe Gly Ser Gly Leu Cys Lys Val Ala Gly
            115                 120                 125

Ala Leu Phe Asn Ile Asn Phe Tyr Ala Gly Ala Leu Leu Leu Ala Cys
        130                 135                 140

Ile Ser Phe Asp Arg Tyr Leu Asn Ile Val His Ala Thr Gln Leu Tyr
145                 150                 155                 160

Arg Arg Gly Pro Pro Ala Arg Val Thr Leu Thr Cys Leu Ala Val Trp
                165                 170                 175

Gly Leu Cys Leu Leu Phe Ala Leu Pro Asp Phe Ile Phe Leu Ser Ala
            180                 185                 190

His His Asp Glu Arg Leu Asn Ala Thr His Cys Gln Tyr Asn Phe Pro
            195                 200                 205

Gln Val Gly Arg Thr Ala Leu Arg Val Leu Gln Leu Val Ala Gly Phe
        210                 215                 220

Leu Leu Pro Leu Leu Val Met Ala Tyr Cys Tyr Ala His Ile Leu Ala
225                 230                 235                 240

Val Leu Leu Val Ser Arg Gly Gln Arg Arg Leu Arg Ala Met Arg Leu
                245                 250                 255

Val Val Val Val Val Val Ala Phe Ala Leu Cys Trp Thr Pro Tyr His
            260                 265                 270

Leu Val Val Leu Val Asp Ile Leu Met Asp Leu Gly Ala Leu Ala Arg
            275                 280                 285

Asn Cys Gly Arg Glu Ser Arg Val Asp Val Ala Lys Ser Val Thr Ser
        290                 295                 300

Gly Leu Gly Tyr Met His Cys Cys Leu Asn Pro Leu Leu Tyr Ala Phe
305                 310                 315                 320

Val Gly Val Lys Phe Arg Glu Arg Met Trp Met Leu Leu Leu Arg Leu
                325                 330                 335

Gly Cys Pro Asn Gln Arg Gly Leu Gln Arg Gln Pro Ser Ser Ser Arg
            340                 345                 350

Arg Asp Ser Ser Trp Ser Glu Thr Ser Glu Ala Ser Tyr Ser Gly Leu
        355                 360                 365

<210> SEQ ID NO 27
<211> LENGTH: 1608
<212> TYPE: DNA
<213> ORGANISM: Mus musculus

<400> SEQUENCE: 27

```
gcaagttccc aaccacaagt gccaaaggca gagaagcagg cagcacgaga cctgacccca      60
gcagccacag ccggagcacc agccaagcca tgtaccttga ggttagtgaa cgtcaagtgc     120
tagatgcctc ggactttgcc tttcttctgg aaaacagcac ctctccctac gattatgggg     180
aaaacgagag cgacttctct gactccccgc cctgcccaca ggatttcagc ctgaactttg     240
acagaacctt cctgccagcc ctctacagcc tcctcttctt gctggggctg ctaggcaatg     300
gggcggtggc tgctgtgcta ctgagtcagc gcactgccct gagcagcacg acaccttcc      360
tgctccacct ggctgtagcc gatgttctgc tggtgttaac tcttccattg tgggcagtgg     420
atgctgctgt ccagtgggtt ttcggccctg gcctctgcaa gtggcaggc gccttgttca      480
acatcaactt ctatgcaggg gccttcctgc tggcttgtat aagcttcgac agatatctga     540
gcatagtgca cgccacccag atctaccgca gggaccccg ggtacgtgta gccctcacct      600
gcatagttgt atggggtctc tgtctgctct ttgccctccc agatttcatc tacctatcag     660
ccaactacga tcagcgcctc aatgccaccc attgccagta caacttccca caggtgggtc     720
gcactgctct gcgtgtactg cagctagtgg ctggtttcct gctgcccctt ctggtcatgg     780
cctactgcta tgcccatatc ctagctgttc tgctggtctc cagaggccag aggcgttttc     840
gagctatgag gctagtggta gtggtggtgg cagccttgc tgtctgctgg acccctatc       900
acctggtggt gctagtggat atcctcatgg atgtgggagt tttggcccgc aactgtggtc     960
gagaaagcca cgtggatgtg gccaagtcag tcacctcggg catggggtac atgcactgct    1020
gcctcaatcc gctgctctat gccttttgtg gagtgaagtt cagagagcaa atgtggatgt    1080
tgttcacgcg cctgggccgc tctgaccaga gagggccca gcggcagccg tcatcttcac    1140
ggagagaatc atcctggtct gagacaactg aggcctccta cctgggcttg taattctgga    1200
ctggaactgt agcctgcgca gcccaagtcc taacacactc caagtgcttg tcctcctggt    1260
agttgggcta gctcgaactt acccgtaact ttgctgccag gatgcactga cagctcagca    1320
tatatccagc tctcctgaga atcaatctca gcaacaagga caacaccatt actgtgcctt    1380
agctgccatg ccctatcttg ctgttttaga actagctgcc tggagcccca ccgccctact    1440
aaattagcaa gtagaactca gccatccctg tgtgagaaga gggagaggca aatagcacag    1500
agggccaggc gttgtcagca ctgaatgtgc ccatctcagt atctcaatat ttgcccaatt    1560
ttatttctag aaacctcact taaactttca ataaacaagg taatgagg                 1608
```

<210> SEQ ID NO 28
<211> LENGTH: 367
<212> TYPE: PRT
<213> ORGANISM: Mus musculus

<400> SEQUENCE: 28

```
Met Tyr Leu Glu Val Ser Glu Arg Gln Val Leu Asp Ala Ser Asp Phe
1               5                   10                  15

Ala Phe Leu Leu Glu Asn Ser Thr Ser Pro Tyr Asp Tyr Gly Glu Asn
            20                  25                  30

Glu Ser Asp Phe Ser Asp Ser Pro Pro Cys Pro Gln Asp Phe Ser Leu
        35                  40                  45

Asn Phe Asp Arg Thr Phe Leu Pro Ala Leu Tyr Ser Leu Leu Phe Leu
```

|     |     |     |     | 50  |     |     |     |     | 55  |     |     |     |     | 60  |     |
| --- | --- | --- | --- | --- | --- | --- | --- | --- | --- | --- | --- | --- | --- | --- | --- |
Leu Gly Leu Leu Gly Asn Gly Ala Val Ala Ala Val Leu Leu Ser Gln
65                      70                      75                      80

Arg Thr Ala Leu Ser Ser Thr Asp Thr Phe Leu Leu His Leu Ala Val
                85                      90                      95

Ala Asp Val Leu Leu Val Leu Thr Leu Pro Leu Trp Ala Val Asp Ala
            100                     105                     110

Ala Val Gln Trp Val Phe Gly Pro Gly Leu Cys Lys Val Ala Gly Ala
        115                     120                     125

Leu Phe Asn Ile Asn Phe Tyr Ala Gly Ala Phe Leu Leu Ala Cys Ile
    130                     135                     140

Ser Phe Asp Arg Tyr Leu Ser Ile Val His Ala Thr Gln Ile Tyr Arg
145                     150                     155                     160

Arg Asp Pro Arg Val Arg Val Ala Leu Thr Cys Ile Val Val Trp Gly
                165                     170                     175

Leu Cys Leu Leu Phe Ala Leu Pro Asp Phe Ile Tyr Leu Ser Ala Asn
            180                     185                     190

Tyr Asp Gln Arg Leu Asn Ala Thr His Cys Gln Tyr Asn Phe Pro Gln
        195                     200                     205

Val Gly Arg Thr Ala Leu Arg Val Leu Gln Leu Val Ala Gly Phe Leu
    210                     215                     220

Leu Pro Leu Leu Val Met Ala Tyr Cys Tyr Ala His Ile Leu Ala Val
225                     230                     235                     240

Leu Leu Val Ser Arg Gly Gln Arg Arg Phe Arg Ala Met Arg Leu Val
                245                     250                     255

Val Val Val Val Ala Ala Phe Ala Val Cys Trp Thr Pro Tyr His Leu
            260                     265                     270

Val Val Leu Val Asp Ile Leu Met Asp Val Gly Val Leu Ala Arg Asn
        275                     280                     285

Cys Gly Arg Glu Ser His Val Asp Val Ala Lys Ser Val Thr Ser Gly
    290                     295                     300

Met Gly Tyr Met His Cys Cys Leu Asn Pro Leu Leu Tyr Ala Phe Val
305                     310                     315                     320

Gly Val Lys Phe Arg Glu Gln Met Trp Met Leu Phe Thr Arg Leu Gly
                325                     330                     335

Arg Ser Asp Gln Arg Gly Pro Gln Arg Gln Pro Ser Ser Ser Arg Arg
            340                     345                     350

Glu Ser Ser Trp Ser Glu Thr Thr Glu Ala Ser Tyr Leu Gly Leu
        355                     360                     365

<210> SEQ ID NO 29
<211> LENGTH: 1172
<212> TYPE: DNA
<213> ORGANISM: Homo sapiens

<400> SEQUENCE: 29
gagacattcc tcaattgctt agacatattc tgagcctaca gcagaggaac ctccagtctc    60
agcaccatga atcaaactgc gattctgatt tgctgcctta tctttctgac tctaagtggc   120
attcaaggag tacctctctc tagaaccgta cgctgtacct gcatcagcat tagtaatcaa   180
cctgttaatc caaggtcttt agaaaaactt gaaattattc tgcaagcca tttttgtcca    240 cgtgttgaga tcattgctac aatgaaaaag aagggtgaga agatgtctct gaatccagaa   300
tcgaaggcca tcaagaattt actgaaagca gttagcaagg aaatgtctaa aagatctcct   360
taaaaccaga ggggagcaaa atcgatgcag tgcttccaag gatggaccac acagaggctg   420

```
cctctcccat cacttcccta catggagtat atgtcaagcc ataattgttc ttagtttgca      480
gttacactaa aaggtgacca atgatggtca ccaaatcagc tgctactact cctgtaggaa      540
ggttaatgtt catcatccta agctattcag taataactct accctggcac tataatgtaa      600
gctctactga ggtgctatgt tcttagtgga tgttctgacc ctgcttcaaa tatttccctc      660
acctttccca tcttccaagg gtactaagga atctttctgc tttggggttt atcagaattc      720
tcagaatctc aaataactaa aaggtatgca atcaaatctg cttttaaag aatgctcttt       780 acttcatgga cttccactgc catcctccca aggggcccaa attctttcag tggctaccta      840
catacaattc caaacacata caggaaggta gaaatatctg aaaatgtatg tgtaagtatt      900
cttatttaat gaaagactgt acaaagtata agtcttagat gtatatattt cctatattgt      960
tttcagtgta catggaataa catgtaatta agtactatgt atcaatgagt aacaggaaaa     1020 tttaaaaat acagatagat atatgctctg catgttacat aagataaatg tgctgaatgg      1080
ttttcaaata aaaatgaggt actctcctgg aaatattaag aaagactatc taaatgttga     1140
aagatcaaaa ggttaataaa gtaattataa ct                                    1172

<210> SEQ ID NO 30
<211> LENGTH: 98
<212> TYPE: PRT
<213> ORGANISM: Homo sapiens

<400> SEQUENCE: 30

Met Asn Gln Thr Ala Ile Leu Ile Cys Cys Leu Ile Phe Leu Thr Leu
1               5                   10                  15

Ser Gly Ile Gln Gly Val Pro Leu Ser Arg Thr Val Arg Cys Thr Cys
            20                  25                  30

Ile Ser Ile Ser Asn Gln Pro Val Asn Pro Arg Ser Leu Glu Lys Leu
        35                  40                  45

Glu Ile Ile Pro Ala Ser Gln Phe Cys Pro Arg Val Glu Ile Ile Ala
    50                  55                  60

Thr Met Lys Lys Lys Gly Glu Lys Arg Cys Leu Asn Pro Glu Ser Lys
65                  70                  75                  80

Ala Ile Lys Asn Leu Leu Lys Ala Val Ser Lys Glu Met Ser Lys Arg
                85                  90                  95

Ser Pro

<210> SEQ ID NO 31
<211> LENGTH: 1063
<212> TYPE: DNA
<213> ORGANISM: Mus musculus

<400> SEQUENCE: 31
catcccgagc caaccttccg gaagcctccc catcagcacc atgaacccaa gtgctgccgt       60
cattttctgc ctcatcctgc tgggtctgag tgggactcaa gggatccctc tcgcaaggac      120
ggtccgctgc aactgcatcc atatcgatga cgggccagtg agaatgaggg ccatagggaa      180
gcttgaaatc atccctgcga gcctatcctg cccacgtgtt gagatcattg ccacgatgaa      240
aaagaatgat gagcagagat gtctgaatcc ggaatctaag accatcaaga atttaatgaa      300
agcgtttagc caaaaaaggt ctaaaagggc tccttaactg gagtgaagcc acgcacacac      360
cccggtgctg cgatggatgg acagcagaga gcctctctcc atcactcccc tttacccagt      420
ggatggctag tcctaattgc ccttggtctt ctgaaaggtg accagccgtg gtcacatcag      480
ctgctactcc tcctgcagga tgatggtcaa gccatggtcc tgagacaaaa gtaactgccg      540
```

-continued

```
aagcaagaat tctttaaggg ctggtctgag tcctcgctca agtggctggg atggctgtcc    600
tagctctgta ctgtaagcta tgtggaggtg cgacgcccct caccatgtgc catgcccagg    660
ctgctcccca caccctcctt gtcctcccta gctcaggctc gtcagttcta agtttacctg    720
agctctttta tttcagatgt aagactacaa atttaagttt gtaagcacga acttaaccac    780
catcttccca aggggttatc aagatactca gaggaacctg aaaatgtatg tgtaaatact    840
atttaatgaa cgactgtaca agtagaatt cctaatgtat tttttgtatg ctttgcattg    900
tatatggaag aacttgtgtc atcaagtatg tatcaatggg tagttaaagt ttatttttaa    960
aaccgtccaa tacctttgt attatgtaac attcaaaaga caatgtactg tattgaaagt    1020
agtaagagac ccaaaatgta ataaagtaat aataactgac atg                     1063
```

<210> SEQ ID NO 32
<211> LENGTH: 98
<212> TYPE: PRT
<213> ORGANISM: Mus musculus

<400> SEQUENCE: 32

Met Asn Pro Ser Ala Ala Val Ile Phe Cys Leu Ile Leu Leu Gly Leu
1               5                   10                  15

Ser Gly Thr Gln Gly Ile Pro Leu Ala Arg Thr Val Arg Cys Asn Cys
            20                  25                  30

Ile His Ile Asp Asp Gly Pro Val Arg Met Arg Ala Ile Gly Lys Leu
        35                  40                  45

Glu Ile Ile Pro Ala Ser Leu Ser Cys Pro Arg Val Glu Ile Ile Ala
    50                  55                  60

Thr Met Lys Lys Asn Asp Glu Gln Arg Cys Leu Asn Pro Glu Ser Lys
65                  70                  75                  80

Thr Ile Lys Asn Leu Met Lys Ala Phe Ser Gln Lys Arg Ser Lys Arg
                85                  90                  95

Ala Pro

<210> SEQ ID NO 33
<211> LENGTH: 1493
<212> TYPE: DNA
<213> ORGANISM: Homo sapiens

<400> SEQUENCE: 33

```
ttcctttcat gttcagcatt tctactcctt ccaagaagag cagcaaagct gaagtagcag     60
caacagcacc agcagcaaca gcaaaaaaca aacatgagtg tgaagggcat ggctatagcc    120
ttggctgtga tattgtgtgc tacagttgtt caaggcttcc ccatgttcaa agaggacgc    180 tgtctttgca taggccctgg ggtaaaagca gtgaaagtgg cagatattga aaagcctcc    240 ataatgtacc caagtaacaa ctgtgacaaa atagaagtga ttattaccct gaaagaaaat    300
aaaggacaac gatgcctaaa tcccaaatcg aagcaagcaa ggcttataat caaaaaagtt    360
gaaagaaaga attttaaaa atatcaaaac atatgaagtc ctggaaaagg gcatctgaaa    420
aacctagaac aagtttaact gtgactactg aaatgacaag aattctacag taggaaactg    480 agactttttct atggttttgt gactttcaac ttttgtacag ttatgtgaag gatgaaaggt    540
gggtgaaagg accaaaaaca gaaatacagt cttcctgaat gaatgacaat cagaattcca    600
ctgcccaaag gagtccagca attaaatgga tttctaggaa aagctacctt aagaaaggct    660
ggttaccatc ggagtttaca aagtgctttc acgttcttac ttgttgtatt atacattcat    720
gcatttctag gctagagaac cttctagatt tgatgcttac aactattctg ttgtgactat    780
```

```
gagaacattt ctgtctctag aagttatctg tctgtattga tctttatgct atattactat      840
ctgtggttac agtggagaca ttgacattat tactggagtc aagcccttat aagtcaaaag      900
catctatgtg tcgtaaagca ttcctcaaac atttttcat gcaaatacac acttcttcc       960 ccaaatatca tgtagcacat caatatgtag ggaaacattc ttatgcatca tttggtttgt     1020
tttataacca attcattaaa tgtaattcat aaaatgtact atgaaaaaaa ttatacgcta     1080
tgggatactg gcaacagtgc acatatttca taaccaaatt agcagcaccg gtcttaattt     1140 gatgttttc aacttttatt cattgagatg ttttgaagca attaggatat gtgtgtttac     1200
tgtacttttt gttttgatcc gtttgtataa atgatagcaa tatcttggac acatttgaaa     1260
tacaaaatgt ttttgtctac caaagaaaaa tgttgaaaaa taagcaaatg tatacctagc     1320
aatcactttt acttttgta attctgtctc ttagaaaaat acataatcta atcaatttct      1380
ttgttcatgc ctatatactg taaaatttag gtatactcaa gactagttta aagaatcaaa     1440 gtcattttt tctctaataa actaccacaa cctttctttt taaaaaaaa aaa              1493

<210> SEQ ID NO 34
<211> LENGTH: 94
<212> TYPE: PRT
<213> ORGANISM: Homo sapiens

<400> SEQUENCE: 34

Met Ser Val Lys Gly Met Ala Ile Ala Leu Ala Val Ile Leu Cys Ala
1               5                   10                  15

Thr Val Val Gln Gly Phe Pro Met Phe Lys Arg Gly Arg Cys Leu Cys
                20                  25                  30

Ile Gly Pro Gly Val Lys Ala Val Lys Val Ala Asp Ile Glu Lys Ala
            35                  40                  45

Ser Ile Met Tyr Pro Ser Asn Asn Cys Asp Lys Ile Glu Val Ile Ile
        50                  55                  60

Thr Leu Lys Glu Asn Lys Gly Gln Arg Cys Leu Asn Pro Lys Ser Lys
65                  70                  75                  80

Gln Ala Arg Leu Ile Ile Lys Lys Val Glu Arg Lys Asn Phe
                85                  90

<210> SEQ ID NO 35
<211> LENGTH: 1597
<212> TYPE: DNA
<213> ORGANISM: Mus musculus

<400> SEQUENCE: 35
gccgttgctc tctgcaaaga gagatctcca aagcccaggc agagagctgc agcggctgct       60
gagatgaaca ggaaggtcac agccatagcc ctggctgcga tcatctgggc cacagctgct      120
caaggcttcc ttatgttcaa cagggggcgc tgtctttgca tcggccccgg gatgaaagcc      180
gtcaaaatgg cagagatcga gaaagcttct gtaatttacc cgagtaacgg ctgcgacaaa      240
gttgaagtga ttgttactat gaaggctcat aaacgacaaa ggtgcctgga ccccagatcc      300
aagcaagctc gcctcataat gcaggcaata gaaaaaaaga attttttaag gcgtcaaaac      360
atgtgacatc ctgggaacgt ctgactgtga gccctccaat aagaactctg tgccaggaac      420
ctgaccctct gctgtcttgg aacatgcagc cacgtattac caggctgcag aactttctag      480
aaggtccgat acatctaaac tgttctactt ggctatgaaa atatttgtc tctaaaagtc      540 acgtgcacac tccacgctac cttctgtggt tacagtggat gcattgttac tgcaatccgg      600
accagtgctg gattcaaaag catctctgtg tgtagtaaaa cattcctcaa agaattgttc      660
```

```
atgcaaataa acattccttt ccccaaatat cacgaggcac acgaacatct aggaagacat    720
ttccacattt tgtcttgttt gttcatttaa aaagactacg attcatttct gcgttgtaga    780
aactagtaag aacactactg tttgtttcct agctagtcac actggcttcc ccctgaggcc    840
ttctaagggg ttaagatgtg tatttcctgt acgtctggtt ttatcagtga caataacaag    900
gatagatttt taaaataaat tggttctgtt caccaaagaa aaatgttgaa aaaaaaatct    960
gtgcacctct ttcagtctgt ttcctgtgag tctgcctttg agaaaaatat ataaatatgt   1020
actttgttct tttccttggt catactgtga atgaatggta gggatggctg gctctgtctc   1080
tccttgaaaa gaataagaat tgtgtttctc tagtaagcta ttataacact tattaaatca   1140
tcaacaacta catgctctct ggacattgag atgcctttag attttgtttt gttttgtttt   1200
gttttttaga gctacacaag ttttttgtcag aattctttag aaacatacac gcctttaatc   1260
ccagcacttg ggaggcagag gcaggcggat ctctgtgagg tccaggccag actggtcttt   1320
cagaacagtc agggctacac aaaattttaa aatagaaagg aatatacttt agtgaggagg   1380
agctgaagat gagaaaaaaa tatgataaaa aggtactgtt aaaaatttca ataaaaaaaa   1440
ttacctaggt gtggtggtat acaccttaat ttcagcactt gaaaggcaga ggcaggagga   1500
tctcttgagt tcaaggccaa cctggtctac agaccaggag tttcaggaca gccagggcta   1560
cacagagaaa ccctatctta aagtaaaaaa aaaaaaa                            1597
```

<210> SEQ ID NO 36
<211> LENGTH: 100
<212> TYPE: PRT
<213> ORGANISM: Mus musculus

<400> SEQUENCE: 36

```
Met Asn Arg Lys Val Thr Ala Ile Ala Leu Ala Ala Ile Ile Trp Ala
1               5                   10                  15

Thr Ala Ala Gln Gly Phe Leu Met Phe Lys Gln Gly Arg Cys Leu Cys
            20                  25                  30

Ile Gly Pro Gly Met Lys Ala Val Lys Met Ala Glu Ile Glu Lys Ala
        35                  40                  45

Ser Val Ile Tyr Pro Ser Asn Gly Cys Asp Lys Val Glu Val Ile Val
    50                  55                  60

Thr Met Lys Ala His Lys Arg Gln Arg Cys Leu Asp Pro Arg Ser Lys
65                  70                  75                  80

Gln Ala Arg Leu Ile Met Gln Ala Ile Glu Lys Lys Asn Phe Leu Arg
                85                  90                  95

Arg Gln Asn Met
        100
```

<210> SEQ ID NO 37
<211> LENGTH: 2033
<212> TYPE: DNA
<213> ORGANISM: Homo sapiens

<400> SEQUENCE: 37

```
gactagttct agatcgcgat ctagaactag ccgcgggaga cgctgctgag gcggcttcgg     60
ttgcgggtcg gaacgcgcgct gctctgcggg gccggtccag gctggcagct gccggcgctt    120
ggcggtgagg gcgggctccc gagtggcccc ccaccgaagg cggtgggacc agcggctgag    180
gccaggatgc cgtccaggcg gcgcggcggc tcctcactca tcccagatgt tggttatctt    240
tctgaagtag actgtccatg gcctgaacat tttccgaaaa tcattttgag caaaatatct    300
```

```
gtttaataac aagataacca catcaagatg gttggaaagc tgaagcagaa cttactattg      360
gcatgtctgg tgattagttc tgtgactgtg ttttacctgg gccagcatgc catggaatgc      420
catcaccgga tagaggaacg tagccagcca gtcaaattgg agagcacaag gaccactgtg      480
agaactggcc tggaccctca agccaacaaa acctttgcct atcacaaaga tatgccttta      540
atatttattg gaggtgtgcc tcggagtgga accacactca tgagggccat gctggacgca      600
catcctgaca ttcgctgtgg agaggaaacc agggtcattc cccgaatcct ggccctgaag      660
cagatgtggt cacggtcaag taaagagaag atccgcctgg atgaggctgg tgttactgat      720
gaagtgctgg attctgccat gcaagccttc ttactagaaa ttatcgttaa gcatggggag      780
ccagcccctt atttatgtaa taaagatcct tttgccctga atctttaac ttacctttct      840
aggttattcc ccaatgccaa atttctcctg atggtccgag atggccgggc atcagtacat      900
tcaatgattt ctcgaaaagt tactatagct ggatttgatc tgaacagcta tagggactgt      960
ttgacaaagt ggaatcgtgc tatagagacc atgtataacc agtgtatgga ggttggttat     1020
aaaaagtgca tgttggttca ctatgaacaa cttgtcttac atcctgaacg gtggatgaga     1080
acactcttaa agttcctcca gattccatgg aaccactcag tattgcacca tgaagagatg     1140
attgggaaag ctgggggagt gtctctgtca aaagtggaga gatctacaga ccaagtaatc     1200
aagccagtca atgtaggagc tctatcaaaa tgggttggga agataccgcc agatgtttta     1260
caagacatgg cagtgattgc tcctatgctt gccaagcttg atatgaccc atatgccaac     1320
ccacctaact acggaaaacc tgatcccaaa attattgaaa acactcgaag ggtctataag     1380
ggagaattcc aactacctga ctttcttaaa gaaaaaccac agactgagca agtggagtag     1440
cagaaccagg agcctcttcc atacatgagg aaagattgct gccttttcag cagaagggaa     1500
attcctagga ttggctgtcc cctgccaagc ttggtggagc gtctgcacct ggctgcgcc     1560
gcctgtgcat ttgccagttt cctcccactg agaggatgga ggtgtccgca cagctttggg     1620
cctcgtgagg atctgcctc ctgagcaaag agctcttgat cccgatttca tgcacagccc     1680
tgcagtaagg agcccagaag gaacatgtgt ttcctgttaa aactcctctt gttctctttt     1740
cttacattat gacgtttgtt ttcaaggaga gggtttaaaa atgggatcct gtaagcagac     1800
ttgggcagtc tccttttgaa ataggttgtc tgtacatgtt ctaatgtttt gtagaacacg     1860
tgtgcctgtt taagtgtatt gatgtgaata atattaaata tcctaattat ttaattcatt     1920
gtattgtttc tgagaagttg ggaaattacc attatacatt tacaacctaa tgacttttgt     1980
atttttatttt tcaaaataaa agctttcaat gtgaagcaaa aaaaaaaaaa aaa           2033
```

<210> SEQ ID NO 38
<211> LENGTH: 370
<212> TYPE: PRT
<213> ORGANISM: Homo sapiens

<400> SEQUENCE: 38

```
Met Val Gly Lys Leu Lys Gln Asn Leu Leu Ala Cys Leu Val Ile
1               5                   10                  15

Ser Ser Val Thr Val Phe Tyr Leu Gly Gln His Ala Met Glu Cys His
                20                  25                  30

His Arg Ile Glu Glu Arg Ser Gln Pro Val Lys Leu Glu Ser Thr Arg
            35                  40                  45

Thr Thr Val Arg Thr Gly Leu Asp Leu Lys Ala Asn Lys Thr Phe Ala
        50                  55                  60

Tyr His Lys Asp Met Pro Leu Ile Phe Ile Gly Gly Val Pro Arg Ser
65                  70                  75                  80
```

Gly Thr Thr Leu Met Arg Ala Met Leu Asp Ala His Pro Asp Ile Arg
            85                  90                  95

Cys Gly Glu Glu Thr Arg Val Ile Pro Arg Ile Leu Ala Leu Lys Gln
            100                 105                 110

Met Trp Ser Arg Ser Lys Glu Lys Ile Arg Leu Asp Glu Ala Gly
            115                 120                 125

Val Thr Asp Glu Val Leu Asp Ser Ala Met Gln Ala Phe Leu Leu Glu
130                 135                 140

Ile Ile Val Lys His Gly Glu Pro Ala Pro Tyr Leu Cys Asn Lys Asp
145                 150                 155                 160

Pro Phe Ala Leu Lys Ser Leu Thr Tyr Leu Ser Arg Leu Phe Pro Asn
                165                 170                 175

Ala Lys Phe Leu Leu Met Val Arg Asp Gly Arg Ala Ser Val His Ser
            180                 185                 190

Met Ile Ser Arg Lys Val Thr Ile Ala Gly Phe Asp Leu Asn Ser Tyr
            195                 200                 205

Arg Asp Cys Leu Thr Lys Trp Asn Arg Ala Ile Glu Thr Met Tyr Asn
210                 215                 220

Gln Cys Met Glu Val Gly Tyr Lys Lys Cys Met Leu Val His Tyr Glu
225                 230                 235                 240

Gln Leu Val Leu His Pro Glu Arg Trp Met Arg Thr Leu Leu Lys Phe
                245                 250                 255

Leu Gln Ile Pro Trp Asn His Ser Val Leu His His Glu Glu Met Ile
            260                 265                 270

Gly Lys Ala Gly Gly Val Ser Leu Ser Lys Val Glu Arg Ser Thr Asp
            275                 280                 285

Gln Val Ile Lys Pro Val Asn Val Gly Ala Leu Ser Lys Trp Val Gly
290                 295                 300

Lys Ile Pro Pro Asp Val Leu Gln Asp Met Ala Val Ile Ala Pro Met
305                 310                 315                 320

Leu Ala Lys Leu Gly Tyr Asp Pro Tyr Ala Asn Pro Pro Asn Tyr Gly
                325                 330                 335

Lys Pro Asp Pro Lys Ile Ile Glu Asn Thr Arg Arg Val Tyr Lys Gly
            340                 345                 350

Glu Phe Gln Leu Pro Asp Phe Leu Lys Glu Lys Pro Gln Thr Glu Gln
            355                 360                 365

Val Glu
370

<210> SEQ ID NO 39
<211> LENGTH: 1867
<212> TYPE: DNA
<213> ORGANISM: Mus musculus

<400> SEQUENCE: 39
tgcctgcctc cggaataagc tgttgaattc ttgtttcttc cagcgcggtg tctgcctgca    60
cgctgccatg cgtcctgcca tgatgataat ggactgaccc tctgaaactg tgccgatccc   120
cttgccacag tcgagtctcc atggcctgac cgtgtcttga caataatttt gagcaaaatc   180
tatgtctaat aagaagataa ccacatcaag atggttggga agctgaagca gaacttactc   240
ttggcgtgtc tggtgattag ttctgtgacc gtgttttacc tgggccagca tgccatggag   300
tgccatcacc gaatagagga acgtagccag ccagcccgac tggagaaccc caaggcgact   360
gtgcgagctg gcctcgacat caaagccaac aaaacattca cctatcacaa agatatgcct   420

```
ttaatattca tcggggtgt gcctcggagc ggcaccacac tcatgagggc tatgctggac    480
gcacatcctg acatccgctg tggagaggaa accagggtca tccctcgaat cctggccctg    540
aagcagatgt ggtcccggtc cagtaaagag aagatccgct tggatgaggc gggtgtcaca    600
gatgaagtgc tagattctgc catgcaagcc ttccttctgg aggtcattgt taaacatggg    660
gagccggcac cttatttatg taacaaagat ccgtttgccc tgaaatcctt gacttacctt    720
gctaggttat ttcccaatgc caaatttctc ctgatggtcc gagatggccg ggcgtcagta    780
cattcaatga tttctcggaa agttactata gctggctttg acctgaacag ctaccgggac    840
tgtctgacca agtggaaccg ggccatagaa accatgtaca accagtgtat ggaagttggt    900
tataagaaat gcatgttggt tcactatgaa cagctcgtct acaccctga acggtggatg    960
agaacgctct aaagttcct ccatattcca tggaaccatt ccgttttgca ccatgaagaa    1020
atgatcggga agctgggggg agtttctctg tcaaaggtgg aaagatcaac agaccaagtc    1080
atcaaacccg tcaacgtggg ggcgctatcg aagtgggttg ggaagatacc cccggacgtc    1140
ttacaagaca tggccgtgat tgcacccatg ctcgccaagc ttggatatga cccatacgcc    1200
aatcctccta actacggaaa acctgacccc aagatccttg aaaacaccag gagggtctat    1260
aaaggagaat tcagctccc tgactttctg aaagaaaaac cccagacgga gcaagtggag    1320
taactgagcc cgtaacttcc cacagggacg actgctgcct tgtctacaga agggaaatct    1380
cgggaacggc tgtctgctgc gacaaggagt gtctgtgccc atcgctcctg ttcacctgcc    1440
agcctcctgt ccccaggggg ggtgtcacac accccggcct ccccaagtga tggctcttga    1500
gcccaggaac atgcatggcc ctcaggatga ggagcccagc agggacacag ttctgtcaca    1560
gctcctcttg tccttgtctt tccttcccag gttccagtct ttaatttcaa ggaaaggaga    1620
gtttgaagtt ggcattctgt taacaaaatc aggcagtctc attccgaata ggttctatgt    1680
acacgttccg atgttttgta gaacactcgt gcctgttgaa acgtatcgat gtggataata    1740
gtaaataccct taattattta aataattcat tgtattgttt cagagacgtt tggaaattac    1800
tgtatacatt tacaacctaa tgactttgt atttttatttt tcaaaataaa gcttaaatg    1860
tgaagca                                                               1867
```

<210> SEQ ID NO 40
<211> LENGTH: 370
<212> TYPE: PRT
<213> ORGANISM: Mus musculus

<400> SEQUENCE: 40

```
Met Val Gly Lys Leu Lys Gln Asn Leu Leu Ala Cys Leu Val Ile
1               5                   10                  15

Ser Ser Val Thr Val Phe Tyr Leu Gly Gln His Ala Met Glu Cys His
                20                  25                  30

His Arg Ile Glu Glu Arg Ser Gln Pro Ala Arg Leu Glu Asn Pro Lys
            35                  40                  45

Ala Thr Val Arg Ala Gly Leu Asp Ile Lys Ala Asn Lys Thr Phe Thr
        50                  55                  60

Tyr His Lys Asp Met Pro Leu Ile Phe Ile Gly Gly Val Pro Arg Ser
65                  70                  75                  80

Gly Thr Thr Leu Met Arg Ala Met Leu Asp Ala His Pro Asp Ile Arg
                85                  90                  95

Cys Gly Glu Glu Thr Arg Val Ile Pro Arg Ile Leu Ala Leu Lys Gln
            100                 105                 110
```

```
Met Trp Ser Arg Ser Ser Lys Glu Lys Ile Arg Leu Asp Glu Ala Gly
            115                 120                 125

Val Thr Asp Glu Val Leu Asp Ser Ala Met Gln Ala Phe Leu Leu Glu
    130                 135                 140

Val Ile Val Lys His Gly Glu Pro Ala Pro Tyr Leu Cys Asn Lys Asp
145                 150                 155                 160

Pro Phe Ala Leu Lys Ser Leu Thr Tyr Leu Ala Arg Leu Phe Pro Asn
                165                 170                 175

Ala Lys Phe Leu Leu Met Val Arg Asp Gly Arg Ala Ser Val His Ser
            180                 185                 190

Met Ile Ser Arg Lys Val Thr Ile Ala Gly Phe Asp Leu Asn Ser Tyr
            195                 200                 205

Arg Asp Cys Leu Thr Lys Trp Asn Arg Ala Ile Glu Thr Met Tyr Asn
210                 215                 220

Gln Cys Met Glu Val Gly Tyr Lys Lys Cys Met Leu Val His Tyr Glu
225                 230                 235                 240

Gln Leu Val Leu His Pro Glu Arg Trp Met Arg Thr Leu Leu Lys Phe
                245                 250                 255

Leu His Ile Pro Trp Asn His Ser Val Leu His His Glu Glu Met Ile
                260                 265                 270

Gly Lys Ala Gly Gly Val Ser Leu Ser Lys Val Glu Arg Ser Thr Asp
            275                 280                 285

Gln Val Ile Lys Pro Val Asn Val Gly Ala Leu Ser Lys Trp Val Gly
    290                 295                 300

Lys Ile Pro Pro Asp Val Leu Gln Asp Met Ala Val Ile Ala Pro Met
305                 310                 315                 320

Leu Ala Lys Leu Gly Tyr Asp Pro Tyr Ala Asn Pro Pro Asn Tyr Gly
                325                 330                 335

Lys Pro Asp Pro Lys Ile Leu Glu Asn Thr Arg Arg Val Tyr Lys Gly
            340                 345                 350

Glu Phe Gln Leu Pro Asp Phe Leu Lys Glu Lys Pro Gln Thr Glu Gln
            355                 360                 365

Val Glu
    370

<210> SEQ ID NO 41
<211> LENGTH: 30
<212> TYPE: DNA
<213> ORGANISM: Artificial Sequence
<220> FEATURE:
<223> OTHER INFORMATION: synthetic

<400> SEQUENCE: 41
gggaatttca cacctaggtg tgaaattccc                                      30
```

MODULATION OF T CELL RECRUITMENT

RELATED APPLICATIONS

This application claims the benefit of U.S. Provisional Application, 60/686,222, filed May 31, 2005, titled "Modulation of T Cell Recruitment". This application is related to U.S. Provisional Application No. 60/645,698, filed Jan. 20, 2005 (pending). This application is also related to U.S. application Ser. No. 10/309,747, filed Dec. 3, 2002 (pending), which is a continuation-in-part application of U.S. application Ser. No. 10/008,264, filed on Dec. 3, 2001 (pending), which is a continuation-in-part application of PCT/US00/15345, filed on Jun. 1, 2000 (expired), published pursuant to PCT Article 21, in English, which claims priority to U.S. Provisional Application Ser. No. 60/137,085, filed Jun. 2, 1999. The entire contents of each of these applications is incorporated herein by this reference.

GOVERNMENT FUNDING

Work described herein was supported, at least in part, under grants AI48126, HL36028, HL53993, awarded by the National Institutes of Health. The U.S. government therefore may have certain rights in this invention.

BACKGROUND OF THE INVENTION

CD4+ T cell phenotypes can be defined according to the pattern of cytokines secreted (Abbas, A. K., et al. (1996) *Nature* 383, 787-793). Type 1 immunity relies on the generation of Th1 cells, whose hallmark cytokine is interferon-gamma (IFN-γ) (Szabo, S. J., et al. (2003) *Annu. Rev Immunol* 21: 713-758). Th2 cells produce a different spectrum of cytokines including interleukin-4 (IL-4) and interleukin-5 (IL-5) and are important in the generation of Type 2 immunity (Abbas, A. K., et al. (1996) *Nature* 383, 787-793). T-bet is a T-box transcription factor essential to Th1 cell generation and effector function (Szabo, S. J. et al. (2000) *Cell* 100, 655-669). Recently, its expression has also been described in NK cells, dendritic cells and CD8+ cells (Szabo, S. J. et al. (2002) *Science* 295, 338; Lugo-Villarino, G., et al. (2003) *Proc. Natl. Acad. Sci. U.S.A* 100, 7749-7754; Townsend, M. J. et al. (2004) *Immunity.* 20, 477-494). T-bet directly transactivates the IFN-γ gene in CD4+ T cells and increases the expression of IL-12 receptor β chain on activated cells. Indeed, a positive feedback loop is observed, since STAT1 downstream of the IFN-γ receptor activates T-bet expression, which further serves to increase IFN-γ secretion (Robinson, D. S. & O'Garra, A. (2002) *Immunity.* 16, 755-758). The strong transactivation of IFN-γ by T-bet makes it difficult to dissect which genes are targets of T-bet and which lie downstream of IFN-γ, as this cytokine is known to induce the expression of many hundreds of genes. When overexpressed in fully polarized Th2 cells, T-bet can reverse their lineage commitment and induce Th1 specific genes, particularly IFN-γ and its known targets (Szabo, S. J. et al. (2000) *Cell* 100, 655-669; Szabo, S. J. et al. (2002) *Science* 295, 338; Lametschwandtner, G. et al. (2004) *J Allergy Clin. Immunol* 113, 987-994). Animals deficient in T-bet demonstrate a marked reduction in severity to a number of inflammatory diseases, including SLE, colitis, diabetes, hepatitis and arthritis, with a number of different abnormalities in effector function described in CD4+ and CD8+ cells (Peng, S. L., et al. (2002) *Proc. Natl. Acad. Sci. U.S.A.* 99, 5545-5550; Neurath, M. F. et al. (2002) *J. Exp. Med.* 195, 1129; Juedes, A. E et al. (2004) *J Exp. Med* 199, 1153-1162; Hultgren, O. H., et al. (2004) *Microbes. Infect.* 6, 529-535; Siebler, J. et al. (2003) *Hepatology* 38, 1573-1580). However, it has been difficult to dissect the precise mechanisms of this protection, as many cell types in the immune system express T-bet Furthermore, given its function as a master regulator of T cell lineage commitment, it is likely to direct the transcription of many genes involved in both cytokine production and other effector pathways.

Effector Th1 and Th2 cells differ profoundly in their migratory properties (Austrup, F. et al. (1997) *Nature* 385, 81-83; Xie, H., et al. (1999) *J Exp. Med.* 189, 1765-1776; Iezzi, G., (2001) *J. Exp. Med.* 193, 987-993; Rot, A. & von Andrian, U. H. (2004) *Annu. Rev Immunol* 22:891-928). Th1 cells migrate to sites of inflammatory immune responses, whereas Th2 cells migrate predominantly to mucosal sites in the settings of allergy or helminth infection. E- and P-selectin ligands are expressed mainly on Th1 cells, being absent on naive T cells and greatly reduced on Th2 cells (Lim, Y. C. et al. (1999) *J. Immunol.* 162, 3193-3201). The initial step in Th1 cell recruitment is binding to P- and E-selectin expressed on activated vascular endothelium, interactions mediated mostly by the leukocyte ligand P-selectin glycoprotein ligand-1 (PSGL-1) (Hirata, T. et al. (2000) *J. Exp. Med.* 192, 1669-1676; Yang, J. et al. (1999) *J. Exp. Med.* 190, 1769-1782). Interestingly, PSGL-1 undergoes further enzymatic post-translational modification including core-2-glycosylation, facosylation and tyrosine sulfation, all of which are required to produce a functional selectin ligand (McEver, R. P. & Cummings, R. D. (1997) *J. Clin. Invest* 100, S97-103). Upregulation of these selectin ligands has thus far been ascribed to the actions of IL-12 on activated lymphocytes, largely in a STAT4 dependent manner (Lim, Y. C. et al. (1999) *J. Immunol* 162, 3193-3201; Lim, Y. C. et al. (2001) *J Immunol* 167, 4476-4484). Chemokines also play critical roles in T cell recruitment by mediating both the transition from selectin-dependent rolling to integrin-mediated firm adhesion (Campbell, J. J. et al. (1998) *Science* 279, 381-384), as well as the subsequent locomotion and transendothelial migration of T cells (Cinamon, G., et al. (2001) *Nat. Immunol.* 2, 515-522). Differential expression of chemokine receptors plays a key part in the process of T cell migration to inflammatory sites. The chemokine receptors CXCR3 and CCR5 are thought to be responsible for the specific recruitment of Th1 cells to inflammatory sites. Other chemokine receptors (e.g., CCR4, CCR10 and CCR9) have also been described to mediate tissue specific homing, although not necessarily in a Th1 specific manner (Syrbe, U., et al. (1999) *Springer Semin. Immunopathol.* 21, 263-285). In contrast, other lymphocyte adhesion molecules implicated in the adhesion cascade, in particular the β1 and β2 integrins, LFA-1 and VLA4, have not been implicated in the specific recruitment of Th1 cells, rather of activated lymphocytes in general. The regulation of cellular trafficking is therefore crucial to an effective immune response.

The resistance of T-bet-deficient (T-bet$^{-/-}$) mice to inflammatory diseases is characterized by a striking lack of T cell infiltration at pathologic sites (Neurath, M. F. et al. (2002) *J. Exp. Med.* 195, 1129; Juedes, A. E et al. (2004) *J Exp. Med* 199, 1153-1162). However, the disease models studied in this context have relied critically upon intact effector function for expression of disease and as such it has been impossible to study T cell tricking in isolation. Identification of a mechanism by which T-bet directly modulates T cell recruitment to sites of inflammation would allow for modulation of the T cell recruitment and inflammation and would be of great benefit.

SUMMARY OF THE INVENTION

The instant invention is based, at least in part, on the discovery that T-bet controls lymphocyte, e.g., T cell, e.g., Th1 cell, recruitment to sites of inflammation. One aspect of the invention features a method for identifying a compound which modulates P-selectin-mediated T cell rolling, comprising contacting in the presence of the compound, T-bet, a P-selectin molecule, and a P-selectin glycoprotein ligand-1 (PSGL-1) molecule under conditions which allow interaction of the PSGL-1 molecule with P-selectin; and detecting the interaction of P-selectin and the PSGL-1 molecule, wherein the ability of the compound to inhibit T cell rolling is indicated by a decrease in the interaction as compared to the amount of interaction in the absence of the compound and the ability of the compound to enhance T cell rolling is indicated by a increase in the interaction as compared to the amount of interaction in the absence of the compound.

In one embodiment, the interaction of P-selectin and the PSGL-1 molecule is determined by measuring the formation of a complex between P-selectin and the PSGL-1 molecule.

In one embodiment, the compound increases the formation or stability of the complex.

In one embodiment, the compound decreases the formation or stability of the complex.

In one embodiment, the interaction of P-selectin and the PSGL-1 molecule is determined by measuring the tyrosine sulfation of PSGL1.

In one embodiment, the method further comprises measuring tyrosyl protein sulfotransferase-2 (TPST-2) expression.

In another aspect, the invention pertains to a method for identifying a compound which modulates stable adherence of a T cell to a vascular endothelial cell, comprising:
 a) contacting a T cell with a test compound;
 b) assaying for modulation of a biological activity of T-bet in the presence of said test compound, wherein a decrease in a biological activity of T-bet by the compound identifies the test compound as a compound that inhibits stable adherence of a T cell to a vascular endothelial cell, and an increase in a biological activity of T-bet by the compound identifies the test compound as a compound that enhances stable adherence of a T cell to a vascular endothelial cell.

In one embodiment, T-bet biological activity is measured by measuring the ability of T-bet to modulate the expression of CXCR3.

In one embodiment, the expression of CXCR3 is determined by PCR. In another embodiment, the expression of CXCR3 is determined by a T cell chemotaxis assay.

In one embodiment, the chemotaxis assay further comprises CXCL11 or CXCL10.

In one embodiment, the biological activity of T-bet is the ability of T-bet to modulate β-integrin dependent binding of the T cell to VCAM-1 on an endothelial cell.

In one embodiment, the assay further comprises CXCL11 or CXCL10.

In one embodiment, the compound modulates the recruitment of a T cell to a site of inflammation.

In one embodiment, the T cell is a Th1 cell.

In another aspect, the invention pertains to a method for modulating P-selectin-mediated T cell rolling, comprising contacting a T cell with an agent that modulates the activity of T-bet and, thereby modulating P-selectin-mediated T cell rolling.

In one embodiment, the agent upmodulates the tyrosine sulfation of PSGL-1, thereby upmodulating P-selectin-mediated T cell rolling.

In another embodiment, the agent downmodulates the tyrosine sulfation of PSGL-1, thereby downmodulating P-selectin-mediated T cell rolling.

DETAILED DESCRIPTION OF THE INVENTION

The instant invention is based, at least in part, on the discovery that T-bet controls Th1 cell recruitment to sites of inflammation. This invention pertains to, inter alia, methods of identifying agents that modulate the effects of T-bet on the recruitment of T cells to sites of inflammation by modulating P-selectin-mediated T cell rolling and/or stable adherence of a T cell to a vascular endothelial cell, as well as methods of use therefore. As discussed in more detail below, T-bet is an important intracellular transducer or mediator of a variety of extracellular signals. More specifically, T-bet is a transcription factor that operates in different cell types to transduce extracellular signals into specific patterns of gene expression. In particular, it has now been demonstrated that T-bet has a central role in both Th1 and Th2 cytokine gene expression. Different cell types and different genes respond to T-bet which, in turn, modulates a variety of cellular responses. Expression of these genes and others similarly controlled by T-bet can be modulated (e.g., enhanced or reduced) by controlling the expression and/or activity of T-bet.

Brachyury or T is the founding member of a family of transcription factors that share a 200 amino acid DNA-binding domain called the T-box (reviewed in Smith, 1997; Papaioannou, 1997; Meisler, 1997). The Brachyury (Greek for 'short tail') mutation was first described in 1927 in heterozygous mutant animals that had a short, slightly kinked tail (Herrmann et al., 1990). The amino-terminal half (amino acids 1-229) of the Brachyury T-box protein contains a conserved domain known as the T box which has been shown to exhibit sequence-specific DNA-binding activity (Kispert, A. & Herrmann, B. G. 1993. *EMBO J.* 12:3211; Papapetrou, C., et al. 1997. *FEBS Lett.* 409:201; Kispert, A., et al. 1995. *EMBO J.* 14:4763). The C-terminal half contains two pairs of transactivation and repression domains. The similarity of sequence between the T box region in orthologous species can be as high as 99% and is around 40-70% between non-orthologous genes. The T-box domain has recently been co-crystallized with DNA and demonstrates a novel sequence-specific DNA recognition architecture in which the protein contacts DNA in both the major and minor grooves (Müller, C. W. & Herrmann, B. G. 1997. *Nature* 389, 884).

A yeast one hybrid approach was used to identify Th-1 specific transcription factors. Yeast cells were made to express an IL-2 promoter-reporter gene construct and were transformed with a cDNA library made from an anti-CD3 activated Th1 cell clone. Inspection of the IL-2 promoter reveals an excellent T-box binding site at −240 to −220 just 5' of the NFkB site. As described in the appended examples, T-bet was isolated in a yeast one hybrid screening assay based on its ability to bind to the 12 promoter.

The T-bet proteins of the invention have homology to T-box proteins. There are now more than eight T-box genes in the mouse not including Brachyury. These include Tbx1-6, T-brain-1 (Thr-1), Eomes, T-pit, and T-bet, each with a distinct and usually complex expression pattern. T-brain-1 expression, for example, is largely restricted to distinct domains within the cerebral cortex (Bulfone, A., et al. 1995. *Neuron* 15, 63. T-bet is most similar in sequence to Tbr-1. Outside of the T-box, the T-bet proteins of the invention bear no similarity to other T-box proteins.

T-bet is a T-box protein expressed only in T cells and is most similar in sequence to Thr-1. Other species also express Brachyury-like genes. Such vertebrate species include *Xenopus*, zebrafish, chick and humans (Rao, 1994; Horb and Thomsen, 1997; Conlon et al., 1996; Ryan et al., 1996; Schulte-Merker et al., 1994; Edwards et al., 1996; Morrison et al., 1996; Law et al., 1995; Cambell et al., 1998) as well as more distant species such as amphioxus, ascidians, echinoderms, *Caenorhabditis elegans*, *Drosophila* and other insects (Holland et al., 1995). These genes are conserved both in sequence and in expression pattern.

T-bet is unique in that it is the only T-box protein to be tyrosine phosphorylated. There are three predicted tyrosine phosphorylation sites at Tyr 76, Tyr 119, and Tyr 531 of human T-bet and one at Tyr 525 of murine T-bet. A nuclear localization sequence is also present at amino acids 498-501 of human T-bet and 493-496 of murine T-bet. Mapping experiments locate two transactivation domains, one 5' and one 3' of the T-box domain. It has been shown that T-bet binds to a consensus T-box site (defined by target site selection (i.e., EMSA and DNA immunoprecipitation assays) in vitro as 5'-GGGAATTTCACACCTAGGTGTGAAATTCCC-3') (SEQ ID NO: 41) and to the human IL-2 promoter, the murine IL-2 promoter, the human IFN-γ intron III, and two binding sites in the murine IFN-γ proximal promoter. (Szabo et al. 2000. *Cell* 100:655-669). T-bet is expressed only in the thymus and in the peripheral lymphoid system. In the periphery, T-bet is expressed only in Th1 cells where it is induced both in response to TcR stimulation and by IL-12. In the thymus levels of T-bet are highest in DN and Rag2−/− thymocytes.

These data demonstrate that the selective expression of T-bet accounts for tissue-specific IFN-γ expression. T-bet is expressed only in Th1 and not in Th2 cells and is induced in the former upon transmission of signals through the T cell receptor.

Furthermore, T-bet is a potent transactivator of the IFN-γ gene. The expression of T-bet correlates with IFN-γ expression in cells of the adaptive and innate immune system including: Th1 cells, B cells, NK cells, and dendritic cells. T-bet is responsible for the genetic program that initiates Th1 lineage development from naïve Thp cells and acts both by initiating Th1 genetic programs and by repressing the opposing programs in Th2 cells. T-bet represses Th2 lineage commitment by an ITK regulated interaction with GATA-3. Upon T cell receptor signaling, T-bet is phosphorylated at residue Y525 by the TCR-activated Tec kinase, ITK, a posttranslational modification required for optimal T-bet mediated repression of Th2 cytokines. The mechanism of such repression is an ITK-mediated interaction between phosphorylated T-bet and GATA-3, resulting in interference with GATA-3 binding to DNA.

In addition to the control of cytokine secretion as described in the appended examples, T-bet controls the recruitment of lymphocytes, e.g., T cells, e.g., Th1 cells, to sites of inflammation. As described herein, T-bet regulates the binding of CD4+ T cells to P-selectin and is required for the expression of the chemokine receptor, CXCR3. Cells deficient in T-bet have a reduction in PSGL-1 tyrosine sulfation and tyrosyl protein sulfotransferase-1 (TPST-1) expression, as well a reduction of CXCR3 expression, reduced binding to P-selectin, and do not attach or migrate in response to appropriate stimuli.

So that the invention may be more readily understood, certain terms are first defined.

As used herein, the term "modulate" includes stimulation (e.g. increasing or upregulating a particular response or activity) and inhibition (e.g. decreasing or downregulating a particular response or activity).

As used herein, the term "T-bet molecules" includes T-bet nucleic acid molecules that share structural features with the nucleic acid molecules shown in SEQ ID NOs: 1 and 3 and T-bet proteins that share the distinguishing structural and functional features of the T-bet proteins shown in SEQ ID NOs 2 and 4. The T-bet proteins are members of the T-box family of proteins and share some amino acid sequence homology to Brachyury, Tbx1-6, and T-brain-1 (Tbr-1). T-box proteins comprise a T-box domain which binds to DNA at a T-box binding site. Further structural and functional features of T-bet proteins are provided below.

As used herein, the term "nucleic acid molecule" includes DNA molecules (e.g., cDNA or genomic DNA) and RNA molecules (e.g. mRNA). The nucleic acid molecule may be single-stranded or double-stranded. The term nucleic acid molecule also includes fragments or equivalents thereof (e.g., fragments or equivalents thereof T-bet, PSGL-1, TPST-1, TPST-2, CXCR3, CXCL11, CXCL10, VCAM-1, and/or β-integrin). The term "equivalent" includes nucleotide sequences encoding functionally equivalent proteins.

An used herein, an "isolated nucleic acid molecule" refers to a nucleic acid molecule that is free of gene sequences which naturally flank the nucleic acid in the genomic DNA of the organism from which the nucleic acid is derived (i.e., genetic sequences that are located adjacent to the gene for the isolated nucleic molecule in the genomic DNA of the organism from which the nucleic acid is derived). For example, in various embodiments, an isolated T-bet nucleic acid molecule typically contains less than about 10 kb of nucleotide sequences which naturally flank the nucleic acid molecule in genomic DNA of the cell from which the nucleic acid is derived, and more preferably contains less than about 5, kb, 4 kb, 3 kb, 2 kb, 1 kb, 0.5 kb or 0.1 kb of naturally flanking nucleotide sequences. An "isolated" T-bet nucleic acid molecule may, however, be linked to other nucleotide sequences that do not normally flank the T-bet sequences in genomic DNA (e.g., the T-bet nucleotide sequences may be linked to vector sequences). In certain preferred embodiments, an "isolated" nucleic acid molecule, such as a cDNA molecule, also may be free of other cellular material. However, it is not necessary for the T-bet nucleic acid molecule to be free of other cellular material to be considered "isolated" (e.g., a T-bet DNA molecule separated from other mammalian DNA and inserted into a bacterial cell would still be considered to be "isolated").

The nucleic acids of the invention can be prepared, e.g., by standard recombinant DNA techniques. A nucleic acid of the invention can also be chemically synthesized using standard techniques. Various methods of chemically synthesizing polydeoxynucleotides are known, including solid-phase synthesis which has been automated in commercially available DNA synthesizers (See e.g., Itakura et al. U.S. Pat. No. 4,598, 049; Caruthers et al. U.S. Pat. No. 4,458,066; and Itakura U.S. Pat. Nos. 4,401,796 and 4,373,071, incorporated by reference herein).

As used herein, the term "hybridizes under high stringency conditions" is intended to describe conditions for hybridization and washing under which nucleotide sequences having substantial homology (e.g., typically greater than 70% homology) to each other remain stably hybridized to each other. A preferred, non-limiting example of high stringency conditions are hybridization in a hybridization buffer that contains 6× sodium chloride/sodium citrate (SSC) at a temperature of about 45° C. for several hours to overnight, followed by one or more washes in a washing buffer containing 0.2×SSC, 0.1% SDS at a temperature of about 50-65° C.

The term "percent (%) identity" as used in the context of nucleotide and amino acid sequences (e.g., when one amino acid sequence is said to be X % identical to another amino acid sequence) refers to the percentage of identical residues shared between the two sequences, when optimally aligned. To determine the percent identity of two nucleotide or amino acid sequences, the sequences are aligned for optimal comparison purposes (e.g., gaps may be introduced in one sequence for optimal alignment with the other sequence). The residues at corresponding positions are then compared and when a position in one sequence is occupied by the same residue as the corresponding position in the other sequence, then the molecules are identical at that position. The percent identity between two sequences, therefore, is a function of the number of identical positions shared by two sequences (i.e., % identity=# of identical positions/total # of positions ×100).

Computer algorithms known in the art can be used to optimally align and compare two nucleotide or amino acid sequences to define the percent identity between the two sequences. A preferred, non-limiting example of a mathematical algorithm utilized for the comparison of two sequences is the algorithm of Karlin and Altschul (1990) Proc. Natl. Acad. Sci. USA 87:2264-68, modified as in Karlin and Altschul (1993) Proc. Natl. Acad. Sci. USA 90:5873-77. Such an algorithm is incorporated into the NBLAST and XBLAST programs of Altschul, et al. ((1990) J. Mol. Biol. 215:403-10). To obtain gapped alignments for comparison purposes, Gapped BLAST can be utilized as described in Altschul et al. ((1997) Nucleic Acids Research 25(17):3389-3402). When utilizing BLAST and Gapped BLAST programs, the default parameters of the respective programs (e.g., XBLAST and NBLAST) can be used. See http://www.ncbi.nlm.nih.gov. For example, the nucleotide sequences of the invention were blasted using the default Blastn matrix 1-3 with gap penalties set at: existence 5 and extension 2. The amino acid sequences of the invention were blasted using the default settings: the Blosum62 matrix with gap penalties set at existence 11 and extension 1.

Another preferred, non-limiting example of a mathematical algorithm utilized for the comparison of sequences is the algorithm of Myers and Miller, CABIOS (1989). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. If multiple programs are used to compare sequences, the program that provides optimal alignment (i.e., the highest percent identity between the two sequences) is used for comparison purposes.

As used herein, a "naturally-occurring" nucleic acid molecule refers to an RNA or DNA molecule having a nucleotide sequence that occurs in nature (e.g. encodes a natural protein).

As used herein, an "antisense" nucleic acid comprises a nucleotide sequence which is complementary to a "sense" nucleic acid encoding a protein, e.g., complementary to the coding strand of a double-stranded cDNA molecule, complementary to an mRNA sequence or complementary to the coding strand of a gene. Accordingly, an antisense nucleic acid can hydrogen bond to a sense nucleic acid.

In one embodiment, nucleic acid molecule of the invention is an siRNA molecule. In one embodiment, a nucleic acid molecule of the invention mediates RNAi. RNA interference (RNAi) is a post-transcriptional, targeted gene-silencing technique that uses double-stranded RNA (dsRNA) to degrade messenger RNA (mRNA) containing the same sequence as the dsRNA (Sharp, P. A. and Zamore, P. D. 287, 2431-2432 (2000); Zamore, P. D., et al. *Cell* 101, 25-33 (2000). Tuschl, T. et al. *Genes Dev.* 13, 3191-3197 (1999); Cottrell T R, and Doering T L. 2003. Trends Microbiol. 11:37-43; Bushman F. 2003. Mol Therapy. 7:9-10; McManus M T and Sharp P A. 2002. Nat Rev Genet. 3:737-47). The process occurs when an endogenous ribonuclease cleaves the longer dsRNA into shorter, e.g., 21- or 22-nucleotide-long RNAs, termed small interfering RNAs or siRNAs. The smaller RNA segments then mediate the degradation of the target mRNA. Kits for synthesis of molecules that mediate RNAi are commercially available from, e.g. New England Biolabs or Ambion. In one embodiment one or more of the chemistries described herein for use in antisense RNA can be employed in molecules that mediate RNAi.

As used herein, the term "coding region" refers to regions of a nucleotide sequence comprising codons which are translated into amino acid residues, whereas the term "noncoding region" refers to regions of a nucleotide sequence that are not translated into amino acids (e.g., 5' and 3' untranslated regions).

As used herein, the term "vector" refers to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" or simply "expression vectors". In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

As used herein, the term "host cell" refers to a cell into which a nucleic acid of the invention, such as a recombinant expression vector of the invention, has been introduced. The terms "host cell" and "recombinant host cell" are used interchangeably herein. It should be understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

As used herein, an "isolated protein" or "isolated polypeptide" refers to a protein or polypeptide that is substantially free of other proteins, polypeptides, cellular material and culture medium when isolated from cells or produced by recombinant DNA techniques, or chemical precursors or other chemicals when chemically synthesized. An "isolated" or "purified" protein or biologically active portion thereof is substantially free of cellular material or other contaminating proteins from the cell or tissue source from which the protein is derived, or substantially free from chemical precursors or other chemicals when chemically synthesized. The language "substantially free of cellular material" includes preparations of T-bet protein in which the protein is separated from cellular components of the cells from which it is isolated or recombinantly produced.

As used herein, the term "antibody" includes immunoglobulin molecules and immunologically active portions of immunoglobulin molecules, i.e., molecules that contain an antigen binding site which specifically binds (immunoreacts with) an antigen, such as Fab and F(ab')$_2$ fragments. The terms "monoclonal antibodies" and "monoclonal antibody composition", as used herein, refer to a population of antibody molecules that contain only one species of an antigen binding site capable of immunoreacting with a particular epitope of an antigen, whereas the term "polyclonal antibodies" and "polyclonal antibody composition" refer to a population of antibody molecules that contain multiple species of antigen binding sites capable of interacting with a particular antigen. A monoclonal antibody compositions thus typically display a single binding affinity for a particular antigen with which it immunoreacts.

As used here, the term "intrabodies" refers to intracellularly expressed antibody constructs, usually single-chain Fv (scFv) antibodies, directed against a target inside a cell, e.g. an intracellular protein such as T-bet.

As used herein, the term "dominant negative T-bet protein" includes T-bet molecules (e.g., portions or variants thereof) that compete with native (i.e., naturally occurring wild-type) T-bet molecules, but which do not have T-bet activity. Such molecules effectively decrease T-bet activity in a cell. As used herein, "dominant negative T-bet protein" refers to a modified form of T-bet which is a potent inhibitor of T-bet activity.

As used herein, the term "cell" includes prokaryotic and eukaryotic cells. In one embodiment, a cell of the invention is a bacterial cell. In another embodiment, a cell of the invention is a fungal cell, such as a yeast cell. In another embodiment, a cell of the invention is a vertebrate cell, e.g., an avian or mammalian cell. Ea a preferred embodiment, a cell of the invention is a murine or human cell.

As used herein, the term "immune cell" or "leukocyte" includes cells that are of hematopoietic origin and that play a role in the immune response. Immune cells include lymphocytes, such as B cells and T cells; natural killer cells; and myeloid cells, such as monocytes, macrophages, eosinophils, mast cells, basophils, and granulocytes.

As used herein, the term "T cell" (i.e., T lymphocyte) includes cells within the T cell lineage, including thymocytes, immature T cells, mature T cells and the like, from a mammal (e.g., human). T cells include mature T cells that express either CD4 or CD8, but not both, and a T cell receptor. The various T cell populations described herein can be defined based on their cytokine profiles and their function.

As used herein, the term "immune response" includes immune cell-mediated (e.g., T cell and/or B cell-mediated) immune responses that are influenced by modulation of immune cell activation. Exemplary immune responses include B cell responses (e.g., antibody production, e.g., IgA production), T cell responses (e.g., proliferation, cytokine production and cellular cytotoxicity), and activation of cytokine responsive cells, e.g., macrophages. In one embodiment of the invention, an immune response is T cell mediated. In another embodiment of the invention, an immune response is B cell mediated. As used herein, the term "downregulation" with reference to the immune response includes a diminution in any one or more immune responses, preferably T cell responses, while the term "upregulation" with reference to the immune response includes an increase in any one or more immune responses, preferably T cell responses. It will be understood that upregulation of one type of immune response may lead to a corresponding downregulation in another type of immune response. For example, upregulation of the production of certain cytokines (e.g., IL-10) can lead to downregulation of cellular immune responses.

As used herein, the term "T helper type 1 response" (Th1 response) refers to a response that is characterized by the production of one or more cytokines selected from IFN-γ, IL-2, TNF, and lymphtoxin (LT) and other cytokines produced preferentially or exclusively by Th1 cells rather than by Th2 cells.

As used herein, a "T helper type 2 response" (Th2 response) refers to a response by CD4$^+$ T cells that is characterized by the production of one or more cytokines selected from IL-4, IL-5, IL-6 and IL-10, and that is associated with efficient B cell "help" provided by the Th2 cells (e.g., enhanced IgG1 and/or IgE production).

As used herein, the term "Th1-associated cytokine" refers to a cytokine that is produced preferentially or exclusively by Th1 cells rather than by Th2 cells. Examples of Th1-associated cytokines include IFN-γ, IL-2, TNF, and lymphtoxin (LT).

As used herein, the term "Th2-associated cytokine" refers to a cytokine that is produced preferentially or exclusively by Th2 cells rather than by Th1 cells. Examples of Th1-associated cytokines include IL-4, IL-5, and IL-10.

As used herein, the term "disease, disorder, or condition that would benefit from treatment with an agent that downmodulates recruitment of a T cell to a site of inflammation" includes disorders in which T-bet activity is aberrant or which would benefit from modulation of a T-bet activity. The agent may directly (e.g., by directly binding to T bet and modulating its activity) or indirectly (e.g., by modulating the activity of a molecule in a signal transduction pathway involving T bet) downmodulate recruitment of a T cell to a site of inflammation. Similarly, the term "disease, disorder, or condition that would benefit from treatment with an agent that upmodulates recruitment of a T cell to a site of inflammation" includes disorders in which T-bet activity is aberrant or which would benefit from modulation of a T-bet activity. The agent may directly or indirectly upmodulate recruitment of a T cell to a site of inflammation.

As used herein, the term "contacting" (i.e., contacting a cell e.g. a cell, with a compound) includes incubating the compound and the cell together in vitro (e.g., adding the compound to cells in culture) as well as administering the compound to a subject such that the compound and cells of the subject are contacted in vivo. The term "contacting" does not include exposure of cells to a T-bet modulator that may occur naturally in a subject (i.e., exposure that may occur as a result of a natural physiological process.

As used herein, the phrase "lymphocyte recirculation" refers to the continuous movement of lymphocytes via the bloodstream and lymphatic system, from one peripheral (secondary) lymphoid tissue to another, and to peripheral inflammatory sites. Normal lymphocyte recirculation is independent of antigen. The process by which particular subsets of lymphocytes selectively enter some tissues but not others is referred to herein as "lymphocyte homing". This regulated movement of lymphocytes into one tissue or another, e.g., into sites of inflammation, is referred to herein as "recruitment" or "lymphocyte recruitment". The patterns of lymphocyte recirculation are governed by the expression of adhesion molecules on lymphocytes and vascular endothelial cells. The pattern of recirculation of naïve lymphocytes is different from those of effector and memory lymphocytes.

As described in the appended Examples, T-bet modulates lymphocyte, e.g., T cell, e.g., Th1 cell, recruitment to sites of inflammation, a tightly regulated and multistep process. Step 1 of this process is rolling of lymphocytes on endothelium. Recirculating lymphocytes are "initially tethered" or "loosely attached" to cytokine activated endothelium via low-affinity interactions between selecting, e.g. E-selectin and P-selectin, on the endothelial surface or by L-selectin on the lymphocyte, and their ligands on the reciprocal cells. These lymphocyte adhesion molecules are concentrated on the tips of the microvillus projections and therefore engage in limited membrane contact with the endothelium. In addition, their binding characteristics favor rapid dissociation. In the microvasculature, the force of flowing blood pushes the tethered lymphocytes and causes disruption of the weak selectin-ligand interactions, and these interactions are rapidly reformed downstream as the lymphocyte contacts the endothelium again. The net result of these events is "rolling of the lymphocyte" along the endothelial surface.

The second step is "activation of lymphocytes". As the lymphocyte is rolling on the surface of the endothelium, it becomes "activated" by chemokines displayed on the surface of the endothelial cells bound to glycosaminoglycan groups of proteoglycans. In response to chemokines, lymphocytes rearrange their cytoskeletons, spread from spherical to a flattened shape, and become more motile. The spreading allows integrins, which are concentrated on the cell surface away from the villous projections, to engage their ligands on the endothelial cells. Activation also results in an increase in the affinty of lymphocyte integrins for endothelial ligands. High-affinity interactions of the integrins with their ligands initiate the third step of the process, which is "stable adherence of lymphocytes to the endothelium". Activated lymphocytes bind firmly to the endothelial cell surface through high-affinity integrins (e.g., γ-integrin, VLA4, LFA-1, Mac-1). These integrins recognize ligands (e.g., ICAM-1, VCAM-1) whose expression on endothelial cells is increased by inflammatory cytokines (e.g., IL-1, TNF). Lymphocytes exhibiting firm adhesion do not roll and appear fixed in place. In fact, such lymphocytes are slowly migrating along the endothelial cell surface until they reach an interendothelial junction.

The fourth step in the process of lymphocyte recruitment to a site of inflammation is "transmigration of lymphocytes through the vessel wall". At interendothelial cell junctions, lymphocytes receive additional signals that trigger their transmigration through the junctions. Migration depends on multiple factors, including but not limited to, reorientation of the integrins to the areas of contact of lymphocytes with the endothelium. Another adhesion molecule Pecam-1 or CD31, may play a role in this process as well. Transmigration may also depend on changes in the structure of the tight junction between the endothelial cells. Once in the tissue, lymphocytes migrate by using their integrins to crawl along the fibrin or fibronectin scaffold that is formed from extravasated plasma proteins. This "extravascular migration" or "extravasation" occurs preferentially toward gradients of chemokines formed within the tissue, resulting in inflammation.

The successful generation of adaptive immune responses depends on leukocyte trafficking events. These events involve the movement of specialized populations of APCs and naive and effector lymphocytes to their sites of action in a coordinated fashion. DCs, transport antigens from peripheral sites of inflammation to secondary lymphoid organs for presentation to the adaptive immune system.

As used herein, "inflammation" is a local accumulation of fluid, plasma proteins and leukocytes (mostly neutrophils, macrophages and lymphocytes). Inflammation occurs after most kinds of tissue injuries or infections or immunologic stimulation as a defense against foreign or altered endogenous substances. Inflammation is normally a self-limiting episode. As described above, an inflammatory reaction is characterized by an initial increase in blood flow to the site of injury, enhanced vascular permeability, and the ordered and directional influx and selective accumulation of different effector cells from the peripheral blood at the site of injury.

Inflammation is also associated with the upmodulation of a number of cytokines, known collectively as pro-inflammatory cytokines. The major pro-inflammatory cytokines are IL1-alpha, IL1-beta, IL6, and TNF-alpha. Other pro-inflammatory mediators include LIF, IFN-gamma, OSM, CNTF, TGF-beta, GM-CSF, IL11, IL12, IL17, IL18, IL8 and a variety of other chemokines that chemoattract inflammatory cells, and various neuromodulatory factors.

The ultimate outcome of an acute inflammatory response to infection is the eradication of the pathogenic microorganism, with minimal environmental damage. In contrast, the chronic version of this activity, promoted by persistent infection or an autoimmune reaction, is consistently being increased with irreversibly destructive consequences.

The term "interact" as used herein is meant to include detectable interactions between molecules, such as can be detected using, for example, a yeast two hybrid assay or coimmunoprecipitation. The term interact is also meant to include "binding" interactions between molecules. Interactions may be, e.g., protein-protein or protein-nucleic acid in nature.

The term "agent" or "compound" or "test compound" includes reagents or test agents which are employed in the methods or assays or present in the compositions of the invention. The term "agent" or "compound" or "test compound" includes compounds that have not previously been identified as, or recognized to be, a modulator of T-bet expression or activity. In one embodiment, more than one compound, e.g. a plurality of compounds, can be tested at the same time in a screening assay for their ability to modulate expression and/or activity of T-bet or a molecule acting upstream or downstream of T-bet in a signal transduction pathway. The term "library of test compounds" refers to a panel comprising a multiplicity of test compounds.

In one embodiment, the term "agent" or "compound" or "test compound" excludes naturally occurring compounds such as cytokines. In another embodiment, the term agent excludes antibodies which bind to naturally occurring cytokines. In another embodiment, the term "agent" excludes antibodies that bind to cytokine receptors. In yet another embodiment, the term "agent" excludes those agents that transduce signals via the T cell receptor, e.g., antigen in the context of an MHC molecule or antibody to a component of the T cell receptor complex. In one embodiment, the agent or test compound is a compound that directly interacts with T-bet or directly interacts with a molecule with which T-bet interacts (e.g., a compound that inhibits or stimulates the interaction between T-bet and a T-bet target molecule, e.g., DNA or another protein). In another embodiment, the compound is one that indirectly modulates T-bet expression and/or activity, e.g., by modulating the activity of a molecule that is upstream or downstream of T-bet in a signal transduction pathway involving T-bet. Such compounds can be identified using screening assays that select for such compounds, as described in detail below.

The term "small molecule" is a term of the art and includes molecules that are less than about 1000 molecular weight or less than about 500 molecular weight. In one embodiment, small molecules do not exclusively comprise peptide bonds. In another embodiment, small molecules are not oligomeric. Exemplary small molecule compounds which can be screened for activity include, but are not limited to, peptides, peptidomimetics, nucleic acids, carbohydrates, small organic molecules (e.g., polyketides) (Cane et al. 1998. Science 282: 63), and natural product extract libraries. In another embodiment, the compounds are small, organic non-peptidic compounds. In a fitter embodiment, a small molecule is not biosynthetic.

As used herein, the term "test compound" includes a compound that has not previously been identified as, or recognized to be, a modulator of T-bet activity and/or expression and/or a modulator of cell growth, survival, differentiation and/or migration.

The term "library of test compounds" is intended to refer to a panel comprising a multiplicity of test compounds.

As used herein, the term "engineered" (as in an engineered cell) refers to a cell into which a nucleic acid molecule encoding the T-bet protein has been introduced.

As used herein, the term "reporter gene" refers to any gene that expresses a detectable gene product, e.g., RNA or protein. Preferred reporter genes are those that are readily detectable. The reporter gene may also be included in a construct in the form of a fusion gene with a gene that includes desired transcriptional regulatory sequences or exhibits other desirable properties. Examples of reporter genes include, but are not limited to CAT (chloramphenicol acetyl transferase) (Alton and Vapnek (1979), Nature 282: 864-869) luciferase, and other enzyme detection systems, such as beta-galactosidase; firefly luciferase (deWet et al. (1987), Mol. Cell. Biol. 7:725-737); bacterial luciferase (Engebrecht and Silverman (1984), PNAS 1: 4154-4158; Baldwin et al. (1984), Biochemistry 23: 3663-3667); alkaline phosphatase (Toh et al. (1989) Eur. J. Biochem. 182: 231-238, Hall et al. (1983) J. Mol. Appl. Gen. 2: 101), human placental secreted alkaline phosphatase (Cullen and Malim (1992) Methods in Enzymol. 216:362-368) and green fluorescent protein (U.S. Pat. No. 5,491,084; WO 96/23898).

As used herein, the term "T-bet-responsive element" refers to a DNA sequence that is directly or indirectly regulated by the activity of T-bet (whereby activity of T-bet can be monitored, for example, via transcription of the reporter genes).

As used herein, the term "cells deficient in T-bet" is intended to include cells of a subject that are naturally deficient in T-bet, as wells as cells of a non-human T-bet deficient animal, e.g., a mouse, that have been altered such that they are deficient in T-bet. The term "cells deficient in T-bet" is also intended to include cells isolated from a non-human T-bet deficient animal or a subject that are cultured in vitro.

As used herein, the term "cell free composition" refers to an isolated composition which does not contain intact cells. Examples of cell free compositions include cell extracts and compositions containing isolated proteins.

As used herein, the term "indicator composition" refers to a composition that includes a protein of interest (e.g., T-bet), for example, a cell that naturally expresses the protein, a cell that has been engineered to express the protein by introducing an expression vector encoding the protein into the cell, or a cell free composition that contains the protein (e.g., purified naturally-occurring protein or recombinantly-engineered protein).

As used herein, the term "a modulator of T-bet" includes a modulator of T-bet expression, processing, post-translational modification, or activity. The term includes agents, for example a compound or compounds which modulates transcription of a T-bet gene, processing of a T-bet mRNA, translation of T-bet mRNA, post-translational modification of a T-bet protein (e.g., glycosylation, ubiquitinization or phosphorylation) or activity of a T-bet protein. A "modulator of T-bet activity" includes compounds that directly or indirectly modulate T-bet activity. For example, an indirect modulator of T-bet activity may modulate a signal transduction pathway that includes T-bet. Examples of modulators that directly modulate T-bet activity include antisense nucleic acid molecules that bind to T-bet mRNA or genomic DNA, intracellular antibodies that bind to T-bet intracellularly and modulate (i.e., inhibit) T-bet activity, T-bet peptides that inhibit the interaction of T-bet with a target molecule and expression vectors encoding T-bet that allow for increased expression of T-bet activity in a cell, dominant negative forms of T-bet, and chemical compounds that act to specifically modulate the activity of T-bet.

As used herein an "agonist" of the T-bet proteins can retain substantially the same, or a subset, of the biological activities of the naturally occurring form of a T-bet protein. An "antagonist" of a T-bet protein can inhibit one or more of the activities of the naturally occurring form of the T-bet protein by, for example, competitively modulating a cellular activity of a T-bet protein.

As used interchangeably herein, "T-bet activity," "biological activity of T-bet" or "functional activity T-bet," include an activity exerted by T-bet protein on a T-bet responsive cell or tissue, e.g., a T cell, e.g., a Th1 cell, dendritic cells, NK cells, or on a T-bet target molecule, e.g., a nucleic acid molecule or protein target molecule, as determined in vivo, or in vitro, according to standard techniques. In one embodiment, T-bet activity is a direct activity, such as an association with a T-bet-target molecule. Alternatively, a T-bet activity is an indirect activity, such as a downstream biological event mediated by interaction of the T-bet protein with a T-bet target molecule. Exemplary biological activities of T-bet are described herein and include, but are not limited to: modulation of P-selectin-mediated T cell rolling, modulation of the stable adherence of a T cell to a vascular endothelial cell, modulation of transmigration of a T cell through a vessel wall, modulation of the recruitment of a T cell to a site of inflammation, modulation of CXCR3 expression, modulation of tyrosyl protein sulfotransferase-1 (TPST-1) expression, modulation of β-integrin dependent binding of a T cell to VCAM-1 on a endothelial cell, modulation, e.g., decrease of Th2 cell lineage commitment, modulation of IFN-γ production in cells of the innate and adaptive immune system, modulation of the production of cytokines, modulation of TGF-β mediated signaling, modulation of the Jak1/STAT-1 pathway, modulation of IgG class switching, modulation of B lymphocyte function, and modulation of disorders that would benefit from modulation of T-bet or modulation of disorders that would benefit from modulation of the recruitment of a T cell to a site of inflammation, e.g., autoimmune diseases, multiple sclerosis or rheumatoid arthritis, infection, e.g., with a virus or a bacterium, asthma, and other disorders or unwanted conditions in which Th1 or Th2 cytokines are implicated, e.g., inflammation. These findings provide for the use of T-bet (and other molecules in the pathways in which T-bet is involved) as drug targets and as targets for therapeutic intervention in various diseases, disorders or conditions. The invention yet further provides immunomodulatory compositions, such as vaccines, comprising agents which modulate T-bet activity.

As used herein, the term "gene whose transcription is regulated by T-bet", includes genes having a regulatory region regulated by T-bet. Such genes can be positively or negatively regulated by T-bet. The term also includes genes which are indirectly modulated by T-bet, i.e., are modulated as the result of the activation of a signaling pathway in which T-bet is involved. Exemplary genes regulated by T-bet include, for example, CXCR3, TPST-2, GATA3, and the cytokine genes, e.g., IL-2, IFN-γ, IL-4, IL-5, TNFα, TGF-β, LT (lymphotoxin), and IL-10.

As used herein, the term "target molecule" or "binding parter" is a molecule with which T-bet binds or interacts in nature, and which interaction results in a biological response. The target molecule can be a protein or a nucleic acid molecule. Exemplary target molecules of the invention include proteins in the same signaling pathway as the T-bet protein, e.g., proteins which may function upstream (including both stimulators and inhibitors of activity) or downstream of the T-bet protein in a pathway involving for example, modulation of P-selectin-mediated T cell rolling, modulation of the stable adherence of a T cell to a vascular endothelial cell, modulation of transmigration of a T cell through a vessel wall, modulation of the recruitment of a T cell to a site of inflammation, modulation of T cell lineage commitment, modulating the production of cytokines, modulating TGF-β mediated signaling, modulating the Jak1/STAT-1 pathway, modulating IgG class switching, modulating B lymphocyte function, and modulating an autoimmune disease. Exemplary T-bet target molecules include, for example, chemokines, e.g., CXCR3, TPST-2, tyrosine kinases, e.g. a Tec kinase such as ITK or rlk or DNA sequences with which T-bet interacts to modulate gene transcription.

As used herein, the term "signal transduction pathway" includes the means by which a cell converts an extracellular influence or signal (e.g., a signal transduced by a receptor on the surface of a cell, such as a cytokine receptor or an antigen receptor) into a cellular response (e.g., modulation of gene transcription). Exemplary signal transduction pathways include the JAK1/STAT-1 pathway (Leonard, W. 2001. *Int. J. Hematol.* 73:271) and the TGF-β pathway (Attisano and Wrana. 2002. *Science.* 296:1646) A "signal transduction pathway involving T-bet" is one in which T-bet is a signaling molecule which relays signals.

As used herein, the term "selectin" refers to a family of cell adhesion molecules that bind to carbohydrates via a lectin-like domain. Selectins are integral membrane glycoproteins with an N-terminal, C type lectin domain, followed by an EGF-like domain, a variable number of repeats of the short consensus sequence of complement regulatory proteins and a single transmembrane domain. Three selectins have been identified and are distinguished by capital letters based on the source of their original identification, i.e. E-selectin (expressed on activated endothelium), L-selectin (expressed on most types of leukocytes), and P-selectin (found in storage granules of platelets). It has been established that a common oligosaccharide determinant on the ligand for L-, P-, and E-selectins is Sialyl Lewis X (sLe$^x$) or some variant of it. However, the specific role of sLe$^x$ in selectin recognition has not been clearly established.

Nonetheless, a high-affinity biological ligand for P-selectin expressed on the surface of lymphocytes has been identified, and is referred to herein as "P-selectin glycoprotein ligand-1" or "PSGL-1". Characteristic features of PSGL-1 include: an oligosaccharide determinant, high density of O-linked glycans, a protein core important for specificity, and an N-terminal region which contains a cluster of negative charge and three potential sites for tyrosine sulfation. In addition, post-translational modification, e.g., tyrosine sulfation, is necessary for the biological activity of PSGL-1. Tyrosine sulfation is mediated by one of two Golgi isoenzymes, called "tyrosylprotein sulfotransferases" ("TPST-1" and "TPST-2").

As used herein, a "chemokine" is a low molecular weight cytokine, identified on the basis of its ability to induce chemotaxis or chemokinesis in leukocytes. Chemokines are divided into subgroups on the basis of genetic, structural, and functional criteria, i.e., the CXC and CC subfamilies. Specifically, chemokines are divided on the basis of the arrangement of the first two of the 4 cysteine residues. The 2 cysteines are separated by a single amino acid in CXC chemokines, while the 2 cysteines are adjacent in CC chemokines. Most CXC chemokines are chemoattractants for neutrophils whereas CC chemokines generally attract monocytes, lymphocytes, basophils, and eosinophils. The biological activities of chemokines are mediated by specific receptors and also by receptors with overlapping ligand specificities that bind several of these proteins which always belong either to the CC-Chemokines or the group of CXC-Chemokines. Lymphocytes require stimulation to become responsive to most known chemokines, and this process is linked closely to chemokine receptor expression. Chemokine receptors belong to the large group of G-protein-coupled seven transmembrane domain receptors which contain seven hydrophobic alpha-helical segments that transverse the membrane. These receptors form a structurally related group within the G-protein-coupled receptor superfamily, which mediate signaling via heterotrimeric G-proteins. Chemokine receptors that bind CXC-Chemokines are designated CXCR followed by a number. Similarly, chemokine receptors that bind CC-Chemokines are designated CCR followed by a number.

As used herein, members of the "Ig superfamily cell adhesion molecules" are calcium-independent transmembrane glycoproteins, including the intercellular adhesion molecules (ICAMs), vascular-cell adhesion molecule (VCAM-1), platelet-endothelial-cell adhesion molecule (PECAM-1), and neural-cell adhesion molecule (NCAM). Each Ig superfamily CAM has an extracellular domain, which contains several Ig-like intrachain disulfide-bonded loops with conserved cysteine residues, a transmembrane domain, and an intracellular domain that interacts with the cytoskeleton. Typically, they bind integrins or other Ig superfamily CAMs.

As used herein, an "integrin" is any of a family of heterodimeric cell-adhesion receptors, consisting of two noncovalently linked polypeptide chains, designated α and β (e.g., β1, β2, and, β3) that mediate cell-to-cell and cell-to-extracellular matrix interactions. As used herein, β-integrin refers to both β1 and β2 integrins. A "β1 integrin" is any integrin containing a β1 chain; members of this group are variously expressed on leukocytes, platelets, and some non-blood cells and mediate cell-matrix adhesion. Heterodimers of this class were first identified on T cells 2 to 4 weeks after activation in vitro and were called very late activation (VLA) antigens; the designation VLA has been continued for other proteins of this group, with numbers designating individual members. A β2 integrin is any integrin containing a β2 chain; members of this group (LFA-1, Mac-1, and p150,95) are expressed on leukocytes and mediate leukocyte adhesion and act as complement receptors; called also leukocyte adhesion protein.

The nucleotide sequence and amino acid sequence of human P-selectin, is described in, for example, GenBank Accession Nos. gi:6031196 and gi:4506877 (SEQ ID Nos.:5 and 6). The nucleotide sequence and amino acid sequence of murine P-selectin, is described in, for example, GenBank Accession No. gi:6755455 and gi:6755456 (SEQ ID NOs.:7 and 8). The nucleotide sequence and amino acid sequence of human E-selectin, is described in, for example, GenBank Accession Nos. gi:4506870 and gi:4506871 (SEQ ID Nos.:9 and 10). The nucleotide sequence and amino acid sequence of murine E-selectin, is described in, for example, GenBank Accession No. gi:6755451 and gi:6755452 (SEQ ID NOs.:11 and 12). The nucleotide sequence and amino acid sequence of human L-selectin, is described in, for example, GenBank Accession Nos. gi:5713320 and gi:4506875 (SEQ ID Nos.: 13 and 14). The nucleotide sequence and amino acid sequence of murine 1-selectin, is described in, for example, GenBank Accession No. gi:6755453 and gi:6755454 (SEQ ID NOs.: 15 and 16). The nucleotide sequence and amino acid sequence of human PSGL-1, is described in, for example, GenBank Accession Nos. gi:6031197 and gi:4506879 (SEQ ID Nos.:17 and 18). The nucleotide sequence and amino acid sequence of murine PSGL1, is described in, for example, GenBank Accession No. gi:31982018 and gi:31982019 (SEQ ED NOs.:19 and 20).

The nucleotide sequence and amino acid sequence of human TPST-1, is described in, for example, GenBank Accession Nos. gi:21361092 and gi:4507665 (SEQ ID Nos.: 37 and 38). The nucleotide sequence and amino acid sequence of murine TPST-1, is described in, for example, GenBank Accession No. gi:7305590 and gi:7305591 (SEQ ID NOs.:39 and 40). The nucleotide sequence and amino acid sequence of human TPST-2, is described in, for example, GenBank Accession Nos. gi:56699462 and gi:56699463 (SEQ ID Nos.:21 and 22). The nucleotide sequence and amino acid sequence of murine TPST-2, is described in, for example, GenBank Accession No. gi:31981951 and gi:6678421 (SEQ ID NOs.:23 and 24).

The nucleotide sequence and amino acid sequence of human CXCR3, is described in, for example, GenBank Accession Nos. gi:4504098 and gi:4504099 (SEQ ID Nos.:25 and 26). The nucleotide sequence and amino acid sequence of murine CXCR3, is described in, for example, GenBank Accession No. gi:6753457 and gi:6753458 (SEQ ID NOs.:27 and 28).

The nucleotide sequence and amino acid sequence of human CXCL10, is described in, for example, GenBank Accession Nos. gi:4504700 and gi:4504701 (SEQ ID Nos.:29 and 30). The nucleotide sequence and amino acid sequence of murine CXCL10, is described in, for example, GenBank Accession No. gi: 10946575 and gi:10946576 (SEQ ID NOs.: 31 and 32).

The nucleotide sequence and amino acid sequence of human CXCL11, is described in, for example, GenBank Accession Nos. gi:14790145 and gi:4885589 (SEQ ID Nos.: 33 and 34). The nucleotide sequence and amino acid sequence of murine CXCL11, is described in, for example, GenBank Accession No. gi:9507070 and gi:9507071 (SEQ ID NOs.:35 and 36).

Various aspects of the invention are described in further detail in the following subsections:

I. Isolated Nucleic Acid Molecules

One aspect of the invention pertains to isolated nucleic acid molecules that encode T-bet. In a preferred embodiment, the nucleic acid molecule of the invention comprises the nucleotide sequence shown in SEQ ID NO:1 or SEQ ID NO:3. In another embodiment, a nucleic acid molecule of the invention comprises at least about 700 contiguous nucleotides of SEQ ID NO: 1 or at least about 500 contiguous nucleotides of SEQ ID NO:3. In a preferred embodiment, a nucleic acid molecule of the invention comprises at least about 800, at least about 1000, at east about 1200, at least about 1400 or at least about 1600 contiguous nucleotides of SEQ ID NO:1. In another preferred embodiment, a nucleic acid molecule of the invention comprises at least about 600, at least about 800, at least about 1000, at least about 1200, or at least about 1400 contiguous nucleotides of SEQ ID NO:3.

In other embodiments, the nucleic acid molecule has at least 70% identity, more preferably 80% identity, and even more preferably 90% identity with a nucleic acid molecule comprising: at least about 700, at least about 800, at least about 1000, at east about 1200, at least about 1400 or at least about 1600 contiguous nucleotides of SEQ ID NO:1. In other embodiments, the nucleic acid molecule has at least 70% identity, more preferably 80% identity, and even more pref- erably 90% nucleotide identity with a nucleic acid molecule comprising: at least about 600, at least about 800, at least about 1000, at least about 1200, or at least about 1400 contiguous nucleotides of SEQ ID NO:3.

Nucleic acid molecules that differ from SEQ ID NO: 1 or 3 due to degeneracy of the genetic code, and thus encode the same T-bet protein as that encoded by SEQ ID NO: 1 and 3, are encompassed by the invention. Accordingly, in another embodiment, an isolated nucleic acid molecule of the invention has a nucleotide sequence encoding a protein having an amino acid sequence shown in SEQ ID NO: 2 or SEQ ID NO:4.

In addition, nucleic acid molecules encoding T-bet proteins can be isolated from other sources using standard molecular biology techniques and the sequence information provided herein. For example, a T-bet DNA can be isolated from a human genomic DNA library using all or portion of SEQ ID NO:1 or 3 as a hybridization probe and standard hybridization techniques (e.g. as described in Sambrook, J., et al. *Molecular Cloning: A Laboratory Manual*. 2nd, ed., Cold Spring Harbor Laboratory, Cold Spring Harbor, N.Y., 1989). Moreover, a nucleic acid molecule encompassing all or a portion of a T-bet gene can be isolated by the polymerase chain reaction using oligonucleotide primers designed based upon the sequence of SEQ ID NO: 1 or 3. For example, mRNA can be isolated from cells (e.g., by the guanidinium-thiocyanate extraction procedure of Chirgwin et al. (1979) *Biochemistry* 18: 5294-5299) and cDNA can be prepared using reverse transcriptase (e.g. Moloney MLV reverse transcriptase, available from Gibco/BRL, Bethesda, Md.; or AMV reverse transcriptase, available from Seikagaku America, Inc., St. Petersburg, Fla.). Synthetic oligonucleotide primers for PCR amplification can be designed based upon the nucleotide sequence shown in SEQ ID NO: 1 or 3. A nucleic acid of the invention can be amplified using cDNA or, alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to a T-bet nucleotide sequence can be prepared by standard synthetic techniques, e.g., using an automated DNA synthesizer.

In addition to the T-bet nucleotide sequence shown in SEQ ID NO: 1 and 3, it will be appreciated by those skilled in the art that DNA sequence polymorphisms that lead to minor changes in the nucleotide or amino acid sequences of T-bet may exist within a population. Such genetic polymorphism in the T-bet gene may exist among individuals within a population due to natural allelic variation. Such natural allelic variations can typically result in 1-2% variance in the nucleotide sequence of the a gene. Such nucleotide variations and resulting amino acid polymorphisms in T-bet that are the result of natural allelic variation and that do not alter the functional activity of T-bet are within the scope of the invention.

Nucleic acid molecules corresponding to natural allelic variants of the T-bet DNAs of the invention can be isolated based on their homology to the T-bet nucleic acid molecules disclosed herein using the human DNA, or a portion thereof, as a hybridization probe according to standard hybridization techniques under high stringency hybridization conditions. Exemplary high stringency conditions include hybridization in a hybridization buffer that contains 6× sodium chloride/sodium citrate (SSC) at a temperature of about 45° C. for several hours to overnight, followed by one or more washes in a washing buffer containing 0.2×SSC, 0.1% SDS at a temperature of about 50-65° C. Accordingly, in another embodiment, an isolated nucleic acid molecule of the invention hybridizes under high stringency conditions to a second nucleic acid molecule comprising the nucleotide sequence of SEQ ID NO: 1 or 3. Preferably, an isolated nucleic acid molecule of the invention that hybridizes under high stringency conditions to the sequence of SEQ ID NO: of SEQ ID NO:1 or 3. In one embodiment, such a nucleic acid molecule is at least about 700, 800, 900, 1000, 1200, 1300, 1400, 1500, or 1600 nucleotides in length. In another embodiment, such a nucleic acid molecule and comprises at least about 700, 800, 900, 1000, 1200, 1300, 1400, 1500, or 1600 contiguous nucleotides of SEQ ID NO: 1 or at least about 500, 600, 700, 800, 900, 1000, 1100, 1200, 1300, 1400, or 1500 contiguous nucleotides of SEQ ID NO: 3. Preferably, an isolated nucleic acid molecule corresponds to a naturally-occurring allelic variant of a T-bet nucleic acid molecule.

In addition to naturally-occurring allelic variants of the T-bet sequence that may exist in the population, the skilled artisan will further appreciate that minor changes may be introduced by mutation into the nucleotide sequence of SEQ ID NO: 1 or 3, thereby leading to changes in the amino acid sequence of the encoded protein, without altering the functional activity of the T-bet protein. For example, nucleotide substitutions leading to amino acid substitutions at "nonessential" amino acid residues may be made in the sequence of SEQ ID NO: 1 or 3. A "non-essential" amino acid residue is a residue that can be altered from the wild-type sequence of T-bet (e.g., the sequence of SEQ ID NO: 1 or 3) without altering the functional activity of T-bet, such as its ability to interact with DNA or its ability to enhance transcription from an IFN-γ promoter, whereas an "essential" amino acid residue is required for functional activity.

Accordingly, another aspect of the invention pertains to nucleic acid molecules encoding T-bet proteins that contain changes in amino acid residues that are not essential for T-bet activity. Such T-bet proteins differ in amino acid sequence from SEQ ID NO: 2 or 4 yet retain T-bet activity. An isolated nucleic acid molecule encoding a non-natural variant of a T-bet protein can be created by introducing one or more nucleotide substitutions, additions or deletions into the nucleotide sequence of SEQ ID NO: 1 or 3 such that one or more amino acid substitutions, additions or deletions are introduced into the encoded protein. Mutations can be introduced into SEQ ID NO: 1 or 3 by standard techniques, such as site-directed mutagenesis and PCR-mediated mutagenesis.

In another embodiment, conservative amino acid substitutions at one or more non-essential amino acid residues are made. A "conservative amino acid substitution" is one in which the amino acid residue is replaced with an amino acid residue having a similar side chain. Families of amino acid residues having similar side chains have been defined in the art, including basic side chains (e.g. lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a nonessential amino acid residue in T-bet is preferably replaced with another amino acid residue from the same side chain family.

Alternatively, in another embodiment, mutations can be introduced randomly along all or part of the T-bet coding sequence, such as by saturation mutagenesis, and the resultant mutants can be screened for their ability to bind to DNA and/or activate transcription, to identify mutants that retain functional activity. Following mutagenesis, the encoded T-bet mutant protein can be expressed recombinantly in a host cell and the functional activity of the mutant protein can be determined using assays available in the art for assessing T-bet activity (e.g. by measuring the ability of the protein to bind to a T-box binding element present in DNA or by measuring the ability of the protein to modulate a Th1 or Th2 phenotype in a T cell.

Another aspect of the invention pertains to isolated nucleic acid molecules that are antisense to the coding strand of a T-bet mRNA or gene. An antisense nucleic acid of the invention can be complementary to an entire T-bet coding strand, or to only a portion thereof. In one embodiment, an antisense nucleic acid molecule is antisense to a coding region of the coding strand of a nucleotide sequence encoding T-bet that is unique to the T-bet family of proteins or which is unique to a T-bet sequence from a particular species. In another embodiment, the antisense nucleic acid molecule is antisense to a noncoding region of the coding strand of a nucleotide sequence encoding T-bet that is unique to T-bet family of proteins or which is unique to a T-bet sequence from a particular species. In preferred embodiments, an antisense molecule of the invention comprises at least about 700 contiguous nucleotides of the noncoding strand of SEQ ID NO: 1, more preferably at least 800, 1000, 1200, 1400, or 1600 contiguous nucleotides of the noncoding strand of SEQ ID NO: 1 or at least about 500 contiguous nucleotides of the noncoding strand of SEQ ID NO: 3, more preferably at least 600, 800, 1000, 1200, or 1400 contiguous nucleotides of the noncoding strand of SEQ ID NO: 3.

Given the coding strand sequences encoding T-bet disclosed herein (e.g., SEQ ID NOs: 1 and 3, antisense nucleic acids of the invention can be designed according to the rules of Watson and Crick base pairing. The antisense nucleic acid molecule may be complementary to the entire coding region of T-bet mRNA, or alternatively can be an oligonucleotide which is antisense to only a portion of the coding or noncoding region of T-bet mRNA. For example, the an" antisense oligonucleotide may be complementary to the region surrounding the translation start site of T-bet mRNA. An antisense oligonucleotide can be, for example, about 15, 20, 21, 22, 23, 24, 25, 30, 35, 40, 45 or 50 nucleotides in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

In another embodiment, an antisense nucleic acid of the invention is a ribozyme. Ribozymes are catalytic RNA molecules with ribonuclease activity which are capable of cleaving a single-stranded nucleic acid, such as an mRNA, to which they have a complementary region. A ribozyme having specificity for a T-bet-encoding nucleic acid can be designed based upon the nucleotide sequence of a T-bet gene disclosed herein. For example, a derivative of a *Tetrahymena* L-19 IVS RNA can be constructed in which the base sequence of the active site is complementary to the base sequence to be cleaved in a T-bet-encoding mRNA. See for example Cech et al. U.S. Pat. No. 4,987,071; and Cech et al. U.S. Pat. No. 5,116,742. Alternatively, T-bet mRNA can be used to select a catalytic RNA having a specific ribonuclease activity from a pool of RNA molecules. See for example Bartel, D. and Szostak, J. W. (1993) *Science* 261: 1411-1418.

In another embodiment, RNAi can be used to inhibit T-bet expression. RNA interference (RNAi) is a post-transcriptional, targeted gene-silencing technique that uses double-stranded RNA (dsRNA) to degrade messenger RNA (mRNA) containing the same sequence as the dsRNA (Sharp, P. A. and Zamore, P. D. 287, 2431-2432 (2000); Zamore, P. D., et al. *Cell* 101, 25-33 (2000). Tuschl, T. et al. *Genes Dev.* 13, 3191-3197 (1999)). The process occurs when an endogenous ribonuclease cleaves the longer dsRNA into shorter, 21- or 22-nucleotide-long RNAs, termed small interfering RNAs or siRNAs. The smaller RNA segments then mediate the degradation of the target mRNA. The antisense RNA strand of dsRNA can be antisense to at least a portion of the coding region of T-bet or to at least a portion of the 5' or 3' untranslated region of the T-bet gene. In one embodiment, siRNA duplexes are composed of 21-nt sense and 21-nt antisense strands, paired in a manner to have a 2-nt 3' overhang. In one embodiment, siRNA sequences with TT in the overhang. The target region can be, e.g., 50 to 100 nt downstream of the start codon, 3'-UTRs may also be targeted. In one embodiment, a 23-nt sequence motif AA(N19)TT (N, any nucleotide) can be searched for and hits with between about 30-70% G/C-content can be selected. If no suitable sequences are found, the search is extended using the motif NA(N21). SiRNAs are preferably chemically synthesized using appropriately protected ribonucleoside phosphoramidites and a conventional DNA/RNA synthesizer. SiRNAs are also available commercially from, e.g., Dharmacon, Xeragon Inc, Proligo, and Ambion. In one embodiment one or more of the chemistries described above for use in antisense RNA can be employed.

Yet another aspect of the invention pertains to isolated nucleic acid molecules encoding T-bet fusion proteins. Such nucleic acid molecules, comprising at least a first nucleotide sequence encoding a T-bet protein, polypeptide or peptide operatively linked to a second nucleotide sequence encoding a non-T-bet protein, polypeptide or peptide, can be prepared by standard recombinant DNA techniques. T-bet fusion proteins are described in further detail below in subsection III.

II. Recombinant Expression Vectors and Host Cells

Another aspect of the invention pertains to vectors, preferably recombinant expression vectors, containing a nucleic acid encoding T-bet (or a portion thereof). The expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" includes promoters, enhancers and other expression control elements (e.g., polyadenylation signals). Such regulatory sequences are described, for example, in Goeddel; *Gene Expression Technology: Methods in Enzymology* 185, Academic Press, San Diego, Calif. (1990). Regulatory sequences include those which direct constitutive expression of a nucleotide sequence in many types of host cell and those which direct expression of the nucleotide sequence only in certain host cells (e.g. tissue-specific regulatory sequences). It will be appreciated by those skilled in the art that the design of the expression vector may depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein (e.g., T-bet proteins, mutant forms of T-bet proteins, T-bet fusion proteins and the like).

The recombinant expression vectors of the invention can be designed for expression of T-bet protein in prokaryotic or eukaryotic cells. For example, T-bet can be expressed in bacterial cells such as *E. coli*, insect cells (using baculovirus expression vectors) yeast cells or mammalian cells. Suitable host cells are discussed further in Goeddel, *Gene Expression Technology: Methods in Enzymology* 185, Academic Press, San Diego, Calif. (1990). Alternatively, the recombinant expression vector may be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors can serve one or more purposes: 1) to increase expression of recombinant protein; 2) to increase the solubility of the recombinant protein; 3) to aid in the purification of the recombinant protein by acting as a ligand in affinity purification; 4) to provide an epitope tag to aid in detection and/or purification of the protein; and/or 5) to provide a marker to aid in detection of the protein (e.g. a color marker using β-galactosidase fusions). Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc.; Smith, D. B. and Johnson, K. S. (1988) *Gene* 67:31-40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. Recombinant proteins also can be expressed in eukaryotic cells as fusion proteins for the same purposes discussed above.

Examples of suitable inducible non-fusion *E. coli* expression vectors include pTrc (Amann et al. (1988) *Gene* 69:301-315) and pET 11d (Studier et al. *Gene Expression Technology: Methods in Enzymology* 185, Academic Press, San Diego, Calif. (1990) 60-89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gn1). This viral polymerase is supplied by host strains BL21(DE3) or HMS174(DE3) from a resident λ prophage harboring a T7 gn1 gene under the transcriptional control of the lacUV 5 promoter.

One strategy to maximize recombinant protein expression in *E. coli* is to express the protein in a host bacteria with an impaired capacity to proteolytically cleave the recombinant protein (Gottesman, S., *Gene Expression Technology: Meth-* ods in *Enzymology* 185, Academic Press, San Diego, Calif. (1990) 119-128). Another strategy is to alter the nucleic acid sequence of the nucleic acid to be inserted into an expression vector so that the individual codons for each amino acid are those preferentially utilized in *E. coli* (Wada et al., (1992) *Nuc. Acids Res.* 20:2111-2118). Such alteration of nucleic acid sequences of the invention can be carried out by standard DNA synthesis techniques.

In another embodiment, the T-bet expression vector is a yeast expression vector. Examples of vectors for expression in yeast *S. cerivisae* include pYepSec1 (Baldari. et al., (1987) *EMBO J.* 6:229-234), pMFa (Kurjan and Herskowitz, (1982) *Cell* 30:933-943), pJRY88 (Schultz et al., (1987) *Gene* 54:113-123), and pYES2 Invitrogen Corporation, San Diego, Calif.).

Alternatively, T-bet can be expressed in insect cells using baculovirus expression vectors. Baculovirus vectors available for expression of proteins in cultured insect cells (e.g., Sf 9 cells) include the pAc series (Smith et al., (1983) *Mol. Cell. Biol.* 3:2156-2165) and the pVL series (Lucklow, V. A., and Summers, M. D., (1989) *Virology* 170:31-39).

In yet another embodiment, a nucleic acid of the invention is expressed in mammalian cells using a mammalian expression vector. Examples of mammalian expression vectors include pMex-NeoI, pCDM8 (Seed, B., (1987) *Nature* 329: 840) and pMT2PC (Kaufman et al. (1987), *EMBO J.* 6:187-195). When used in mammalian cells, the expression vector's control functions are often provided by viral regulatory elements. For example, commonly used promoters are derived from polyoma, Adenovirus 2, cytomegalovirus and Simian Virus 40.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include lymphoid-specific promoters (Calame and Eaton (1988) *Adv. Immunol.* 43:235-275), in particular promoters of T cell receptors (Winoto and Baltimore (1989) *EMBO J.* 8:729-733) and immunoglobulins (Banerji et al. (1983) *Cell* 33:729-740; Queen and Baltimore (1983) *Cell* 33:741-748), the albumin promoter (liver-specific; Pinkert et al. (1987) *Genes Dev.* 1:268-277), neuron-specific promoters (e.g., the neurofilament promoter; Byrne and Ruddle (1989) *Proc. Natl. Acad. Sci. USA* 86:5473-5477), pancreas-specific promoters (Edlund et al. (1985) *Science* 230:912-916), and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss (1990) *Science* 249:374-379) and the α-fetoprotein promoter (Campes and Tilghman (1989) *Genes Dev.* 3:537-546).

Moreover, inducible regulatory systems for use in mammalian cells are known in the art, for example systems in which gene expression is regulated by heavy metal ions (see e.g., Mayo et al. (1982) *Cell* 29:99-108; Brinster et al. (1982) *Nature* 296:39-42; Searle et al. (1985) *Mol. Cell. Biol.* 5:1480-1489), heat shock (see e.g., Nouer et al. (1991) in *Heat Shock Response*, e.d. Nouer, L., CRC, Boca Raton, Fla., pp 167-220), hormones (see e.g., Lee et al. (1981) *Nature* 294:228-232; Hynes et al. (1981) *Proc. Natl. Acad. Sci. USA* 78:2038-2042; Klock et al. (1987) *Nature* 329:734-736; Israel & Kaufman (1989) *Nucl. Acids Res.* 17:2589-2604; and PCT Publication No. WO 93/23431), FK506-related molecules (see e.g., PCT Publication No. WO 94/18317) or tetracyclines (Gossen, M. and Bujard, H. (1992) *Proc. Natl. Acad. Sci. USA* 89:5547-5551; Gossen, M. et al. (1995) *Science* 268:1766-1769; PCT Publication No. WO 94/29442; and PCT Publication No. WO 96/01313). Accordingly, in another embodiment, the invention provides a recombinant expression vector in which T-bet DNA is operatively linked to an inducible eukaryotic promoter, thereby allowing for inducible expression of T-bet protein in eukaryotic cells.

The invention further provides a recombinant expression vector comprising a DNA molecule of the invention cloned into the expression vector in an antisense orientation. That is, the DNA molecule is operatively linked to a regulatory sequence in a manner which allows for expression (by transcription of the DNA molecule) of an RNA molecule which is antisense to T-bet mRNA. Regulatory sequences operatively linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub, H. et al., Antisense RNA as a molecular tool for genetic analysis, *Reviews—Trends in Genetics*, Vol. 1(1) 1986.

Another aspect of the invention pertains to recombinant host cells into which a vector, preferably a recombinant expression vector, of the invention has been introduced. A host cell may be any prokaryotic or eukaryotic cell. For example, T-bet protein may be expressed in bacterial cells such as *E. coli*, insect cells, yeast or mammalian cells (such as Chinese hamster ovary cells (CHO) or COS cells). Other suitable host cells are known to those skilled in the art. Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook et al (*Molecular Cloning: A Laboratory Manual*, 2nd Edition, Cold Spring Harbor Laboratory press (1989)), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to compounds, such as G418, hygromycin and methotrexate. Nucleic acid encoding a selectable marker may be introduced into a host cell on the same vector as that encoding T-bet or may be introduced on a separate vector. Cells stably transfected with the introduced nucleic acid can be identified by compound selection (e.g., cells that have incorporated the selectable marker gene will survive, while the other cells die).

A host cell of the invention, such as a prokaryotic or eukaryotic host cell in culture, can be used to produce (i.e., express) T-bet protein. Accordingly, the invention further provides methods for producing T-bet protein using the host cells of the invention. In one embodiment, the method comprises culturing the host cell of invention (into which a recombinant expression vector encoding T-bet has been introduced) in a suitable medium until T-bet is produced. In another embodiment, the method further comprises isolating T-bet from the medium or the host cell. In its native form the T-bet protein is an intracellular protein and, accordingly, recombinant T-bet protein can be expressed intracellularly in a recombinant host cell and then isolated from the host cell, e.g., by lysing the host cell and recovering the recombinant T-bet protein from the lysate. Alternatively, recombinant T-bet protein can be prepared as a extracellular protein by operatively linking a heterologous signal sequence to the amino-terminus of the protein such that the protein is secreted from the host cells. In this case, recombinant T-bet protein can be recovered from the culture medium in which the cells are cultured.

Certain host cells of the invention can also be used to produce nonhuman transgenic animals using methods known in the art.

III. Isolated T-bet Proteins and Anti-T-bet Antibodies

Another aspect of the invention pertains to isolated T-bet proteins. Preferably, the T-bet protein comprises the amino acid sequence encoded by SEQ ID NO: 1 or 3. In another preferred embodiment, the protein comprises the amino acid sequence of SEQ ID NO: 2 or 4. In other embodiments, the protein has at least 60% amino acid identity, more preferably 70% amino acid identity, more preferably 80%, and even more preferably, 90% or 95% amino acid identity with the amino acid sequence shown in SEQ ID NO: 2 or 4.

In other embodiments, the invention provides isolated portions of the T-bet protein. For example, the invention further encompasses an amino-terminal portion of T-bet that includes a T-box domain. In various embodiments, this amino terminal portion encompasses at least amino acids 138-327 of human T-bet or at least amino acids 137-326 of mouse T-bet. Another isolated portion of T-bet provided by the invention is a portion encompassing a tyrosine phosphorylation site. This portion comprises at least about 20, at least about 50, at least about 100, or at least about 200 amino acids of T-bet and includes at least amino acids Tyr 76, Tyr 119, and/or Tyr 531 of human T-bet or amino acids Tyr 525 of murine T-bet. Yet another isolated portion of T-bet provided herein is a portion encompassing a nuclear localization sequence shown in amino acids 498-501 of human T-bet or 493-496 of murine T-bet.

T-bet proteins of the invention are preferably produced by recombinant DNA techniques. For example, a nucleic acid molecule encoding the protein is cloned into an expression vector (as described above), the expression vector is introduced into a host cell (as described above) and the T-bet protein is expressed in the host cell. The T-bet protein can then be isolated from the cells by an appropriate purification scheme using standard protein purification techniques. Alternative to recombinant expression, a T-bet polypeptide can be synthesized chemically using standard peptide synthesis techniques. Moreover, native T-bet protein can be isolated from cells (e.g. from T cells), for example by immunoprecipitation using an anti-T-bet antibody.

The present invention also pertains to variants of the T-bet proteins which function as either T-bet agonists (mimetics) or as T-bet antagonists. Variants of the T-bet proteins can be generated by mutagenesis, e.g., discrete point mutation or truncation of a T-bet protein. Thus, specific biological effects can be elicited by treatment with a variant of limited function. In one embodiment, treatment of a subject with a variant having a subset of the biological activities of the naturally occurring form of the protein has fewer side effects in a subject relative to treatment with the naturally occurring form of the T-bet protein. In one embodiment, the invention pertains to derivatives of T-bet which may be formed by modifying at least one amino acid residue of T-bet by oxidation, reduction, or other derivatization processes known in the art.

In one embodiment, variants of a T-bet protein which function as either T-bet agonists (mimetics) or as T-bet antagonists can be identified by screening combinatorial libraries of mutants, e.g., truncation mutants, of a T-bet protein for T-bet protein agonist or antagonist activity. In one embodiment, a variegated library of T-bet variants is generated by combinatorial mutagenesis at the nucleic acid level and is encoded by a variegated gene library. A variegated library of T-bet variants can be produced by, for example, enzymatically ligating a mixture of synthetic oligonucleotides into gene sequences such that a degenerate set of potential T-bet sequences is expressible as individual polypeptides, or alternatively, as a set of larger fusion proteins (e.g., for phage display) containing the set of T-bet sequences therein. There are a variety of methods which can be used to produce libraries of potential T-bet variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential T-bet sequences. Methods for synthesizing degenerate oligonucleotides are known in the art (see, e.g., Narang, S. A., 1983, *Tetrahedron* 39:3; Itakura et al., 1984, *Annu. Rev. Biochem.* 53:323; Itakura et al., 1984, *Science* 198:1056; Ike et al., 1983, *Nucleic Acid Res.* 11:477).

In addition, libraries of fragments of a T-bet protein coding sequence can be used to generate a variegated population of T-bet fragments for screening and subsequent selection of variants of a T-bet protein. In one embodiment, a library of coding sequence fragments can be generated by treating a double stranded PCR fragment of a T-bet coding sequence with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal, C-terminal and internal fragments of various sizes of the T-bet protein.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of T-bet proteins. The most widely used techniques, which are amenable to high throughput analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a technique which enhances the frequency of functional mutants in the libraries, can be used in combination with the screening assays to identify T-bet variants (Arkin and Yourvan, 1992, *Proc. Natl. Acad. Sci. USA* 89:7811-7815; Delgrave et al., 1993, *Protein Engineering* 6(3):327-331).

The invention also provides T-bet fusion proteins. As used herein, a T-bet "fusion protein" comprises a T-bet polypeptide operatively linked to a polypeptide other than T-bet. A "T-bet polypeptide" refers to a polypeptide having an amino acid sequence corresponding to T-bet protein, or a peptide fragment thereof which is unique to T-bet protein whereas a "polypeptide other than T-bet" refers to a polypeptide having an amino acid sequence corresponding to another protein. Within the fusion protein, the term "operatively linked" is intended to indicate that the T-bet polypeptide and the other polypeptide are fused in-frame to each other. The other polypeptide may be fused to the N-terminus or C-terminus of the T-bet polypeptide. For example, in one embodiment, the fusion protein is a GST-T-bet fusion protein in which the T-bet sequences are fused to the C-terminus of the GST sequences. In another embodiment, the fusion protein is a T-bet-IA fusion protein in which the T-bet nucleotide sequence is inserted in a vector such as pCEP4-HA vector (Herrscher, R. F. et al. (1995) *Genes Dev.* 9:3067-3082) such that the T-bet sequences are fused in frame to an influenza hemagglutinin epitope tag. Such fusion proteins can facilitate the purification of recombinant T-bet.

Preferably, a T-bet fusion protein of the invention is produced by standard recombinant DNA techniques. For example, DNA fragments coding for the different polypeptide sequences are ligated together in-frame in accordance with conventional techniques, for example employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, *Current Protocols in Molecular Biology*, eds. Ausubel et al. John Wiley & Sons: 1992). Moreover, many expression vectors are commercially available that already encode a fusion moiety (e.g., a GST polypeptide or an HA epitope tag). A T-bet-encoding nucleic acid can be cloned into such an expression vector such that the fusion moiety is linked in-frame to the T-bet protein.

An isolated T-bet protein, or fragment thereof, can be used as an immunogen to generate antibodies that bind specifically to T-bet using standard techniques for polyclonal and monoclonal antibody preparation. The T-bet protein can be used to generate antibodies. For example, polyclonal antisera, can be produced in rabbits using full-length recombinant bacterially produced T-bet as the immunogen. This same immunogen can be used to produce mAb by immunizing mice and removing spleen cells from the immunized mice. Spleen cells from mice mounting an immune response to T-bet can be fused to myeloma cells, e.g., SP2/O—Ag14 myeloma. As described in the appended examples, this methods were used to make polyclonal and monoclonal antibodies which bind to T-bet. In one embodiment, the antibodies can be produced in an animal that does not express T-bet, such as a T-bet knock-out animal. In another embodiment, the antibodies can be generated in a non-human animal having a specific genetic background, e.g., as achieved by backcrossing.

Alternatively, an antigenic peptide fragment of T-bet can be used as the immunogen. An antigenic peptide fragment of T-bet typically comprises at least 8 amino acid residues of the amino acid sequence shown in SEQ ID NO: 2 or 4 and encompasses an epitope of T-bet such that an antibody raised against the peptide forms a specific immune complex with T-bet. Preferably, the antigenic peptide comprises at least 10 amino acid residues, more preferably at least 15 amino acid residues, even more preferably at least 20 amino acid residues, and most preferably at least 30 amino acid residues. Preferred epitopes encompassed by the antigenic peptide are regions of T-bet that are located on the surface of the protein, e.g., hydrophilic regions, and that are unique to T-bet. In one embodiment such epitopes can be specific for T-bet proteins from one species, such as mouse or human (i.e., an antigenic peptide that spans a region of T-bet that is not conserved across species is used as immunogen; such non conserved residues can be determined using an alignment such as that provided herein). A standard hydrophobicity analysis of the T-bet protein can be performed to identify hydrophilic regions.

A T-bet immunogen typically is used to prepare antibodies by immunizing a suitable subject, (e.g., rabbit, goat, mouse or other mammal) with the immunogen. An appropriate immunogenic preparation can contain, for examples, recombinantly expressed T-bet protein or a chemically synthesized T-bet peptide. The preparation can further include an adjuvant, such as Freund's complete or incomplete adjuvant, or similar immunostimulatory agent. Immunization of a suitable subject with an immunogenic T-bet preparation induces a polyclonal anti-T-bet antibody response.

Accordingly, another aspect of the invention pertains to anti-T-bet antibodies. Polyclonal anti-T-bet antibodies can be prepared as described above by immunizing a suitable subject with a T-bet immunogen. The anti-T-bet antibody titer in the immunized subject can be monitored over time by standard techniques, such as with an enzyme linked immunosorbent assay ELISA) using immobilized T-bet. If desired, the antibody molecules directed against T-bet can be isolated from the mammal (e.g., from the blood) and further purified by well known techniques, such as protein A chromatography to obtain the IgG fraction. At an appropriate time after immunization, e.g., when the anti-T-bet antibody titers are highest, antibody-producing cells can be obtained from the subject and used to prepare monoclonal antibodies by standard techniques, such as the hybridoma technique originally described by Kohler and Milstein (1975, *Nature* 256:495-497) (see also, Brown et al. (1981) *J Immunol* 127:539-46; Brown et al. (1980) *J Biol Chem* 255:4980-83; Yeh et al. (1976) *PNAS* 76:2927-31; and Yeh et al. (1982) *Int. J. Cancer* 29:269-75), the more recent human B cell hybridoma technique (Kozbor et al. (1983) *Immunol Today* 4:72), the EBV-hybridoma technique (Cole et al. (1985), *Monoclonal Antibodies and Cancer Therapy*, Alan R. Liss, Inc., pp. 77-96) or trioma techniques. The technology for producing monoclonal antibody hybridomas is well known (see generally R. H. Kenneth, in *Monoclonal Antibodies: A New Dimension In Biological Analyses*, Plenum Publishing Corp., New York, N.Y. (1980); E. A. Lerner (1981) *Yale J. Biol. Med.*, 54:387-402; M. L. Gefter et al. (1977) *Somatic Cell Genet.*, 3:231-36). Briefly, an immortal cell line (typically a myeloma) is fused to lymphocytes (typically splenocytes) from a mammal immunized with a T-bet immunogen as described above, and the culture supernatants of the resulting hybridoma cells are screened to identify a hybridoma producing a monoclonal antibody that binds specifically to T-bet.

Any of the many well known protocols used for fusing lymphocytes and immortalized cell lines can be applied for the purpose of generating an anti-T-bet monoclonal antibody (see, e.g., G. Galfre et al. (1977) *Nature* 266:55052; Gefter et al. *Somatic Cell Genet.*, cited supra; Lerner, *Yale J. Biol.*

Med., cited supra; Kenneth, *Monoclonal Antibodies*, cited supra). Moreover, the ordinary skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines may be used as a fusion partner according to standard techniques, e.g., the P3-NS1/1-Ag4-1, P3-x63-Ag8.653 or Sp2/O—Ag14 myeloma lines. These myeloma lines are available from the American Type Culture Collection (ATCC), Rockville, Md. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind T-bet, e.g., using a standard ELISA assay.

Using such methods several antibodies to T-bet have been generated. Both monoclonal and polyclonal antibodies were generated against full-length recombinant bacterially produced T-bet protein. The 3D10 antibody is of the IgG subtype and the 4B10 antibody was produced by fusion of mouse spleen cells to the SP2/0-Ag14 myeloma and is of the IgG subtype. The 39D antibody recognizes both human and murine T-bet.

Alternative to preparing monoclonal antibody-secreting hybridomas, a monoclonal anti-T-bet antibody can be identified and isolated by screening a recombinant combinatorial immunoglobulin library (e.g., an antibody phage display library) with T-bet to thereby isolate immunoglobulin library members that bind T-bet. Kits for generating and screening phage display libraries are commercially available (e.g., the Pharmacia *Recombinant Phage Antibody System*, Catalog No. 27-9400S01; and the Stratagene *SurfZAP™ Phage Display Kit*, Catalog No. 240612). Additionally, examples of methods and reagents particularly amenable for use in generating and screening antibody display library can be found in, for example, Ladner et al. U.S. Pat. No. 5,223,409; Kang et al. International Publication No. WO 92/18619; Dower et al. International Publication No. WO 91/17271; Winter et al. International Publication WO 92/20791; Markland et al. International Publication No. WO 92/15679; Breitling et al. International Publication WO 93/01288; McCafferty et al. International Publication No. WO 92/01047; Garrard et al. International Publication No. WO 92/09690; Ladner et al. International Publication No. WO 90/02809; Fuchs et al. (1991) *Bio/Technology* 9:1370-1372; Hay et al. (1992) *Hum Antibod Hybridomas* 3:81-85; Huse et al. (1989) *Science* 246:1275-1281; Griffiths et al. (1993) *EMBO J.* 12:725-734; Hawkins et al. (1992) *J Mol Biol* 226:889-896; Clarkson et al. (1991) *Nature* 352:624-628; Gram et al. (1992) *PNAS* 89:3576-3580; Garrad et al. (1991) *Bio/Technology* 9:1373-1377; Hoogenboom et al. (1991) *Nuc Acid Res* 19:4133-4137; Barbas et al. (1991) *PNAS* 88:7978-7982; and McCafferty et al. *Nature* (1990) 348:552-554.

Additionally, recombinant anti-T-bet antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in Robinson et al. international Patent Publication PCT/US86/02269; Akira, et al. European Patent Application 184,187; Taniguchi, M., European Patent Application 171,496; Morrison et al. European Patent Application 173,494; Neuberger et al. PCT Application WO 86/01533; Cabilly et al. U.S. Pat. No. 4,816,567; Cabilly et al. European Patent Application 125,023; Better et al. (1988) *Science* 240:1041-1043; Liu et al. (1987) *PNAS* 84:3439-3443; Liu et al. (1987) *J. Immunol.* 139:3521-3526; Sun et al. (1987) *PNAS* 84:214-218; Nishimura et al. (1987) *Canc. Res.* 47:999-1005; Wood et al. (1985) *Nature* 314:446-449; and Shaw et al. (1988) *J. Natl Cancer Inst.* 80:1553-1559); Morrison, S. L. (1985) *Science* 229:1202-1207; Oi et al. (1986) *BioTechniques* 4:214; Winter U.S. Pat. No. 5,225,539; Jones et al. (1986) *Nature* 321:552-525; Verhoeyan et al. (1988) *Science* 239:1534; and Beidler et al. (1988) *J. Immunol.* 141:4053-4060.

In another embodiment, fully human antibodies can be made using techniques that are known in the art. For example, fully human antibodies against a specific antigen can be prepared by administering the antigen to a transgenic animal which has been modified to produce such antibodies in response to antigenic challenge, but whose endogenous loci have been disabled. Exemplary techniques that can be used to make antibodies are described in U.S. Pat. Nos. 6,150,584; 6,458,592; 6,420,140. Other techniques are known in the art.

An anti-T-bet antibody (e.g., monoclonal antibody) can be used to isolate T-bet by standard techniques, such as affinity chromatography or immunoprecipitation. An anti-T-bet antibody can facilitate the purification of natural T-bet from cells and of recombinantly produced T-bet expressed in host cells. Moreover, an anti-T-bet antibody can be used to detect T-bet protein (e.g., in a cellular lysate or cell supernatant). Detection may be facilitated by coupling (i.e., physically linking) the antibody to a detectable substance. Accordingly, in one embodiment, an anti-T-bet antibody of the invention is labeled with a detectable substance. Examples of detectable substances include various enzymes, prosthetic groups, fluorescent materials, luminescent materials and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; and examples of suitable radioactive material include $^{125}$I, $^{131}$I, $^{35}$S or $^{3}$H.

Yet another aspect of the invention pertains to anti-T-bet antibodies that are obtainable by a process comprising:

(a) immunizing an animal with an immunogenic T-bet protein, or an immunogenic portion thereof unique to T-bet protein; and (b) isolating from the animal antibodies that specifically bind to a T-bet protein.

Methods for immunization and recovery of the specific anti-T-bet antibodies are described further above.

In yet another aspect, the invention pertains to T-bet intrabodies. Intrabodies are intracellularly expressed antibody constructs, usually single-chain Fv (scFv) antibodies directed against a target inside a cell, e.g. an intracellular protein such as T-bet (Graus-Porta, D. et al. (1995) Mol. Cell Biol. 15(1): 182-91). For example, an intrabody (e.g., and scFv) can contain the variable region of the heavy and the light chain, linked by a flexible linker and expressed from a single gene. The variable domains of the heavy and the light chain contain the complementarity determining regions (CDRs) of the parent antibody, i.e., the main antigen binding domains, which determine the specificity of the scFvs. The scFv gene can be transferred into cells, where scFv protein expression can modulate the properties of its target, e.g., T-bet. Accordingly, in one embodiment, the invention provides a method for using such T-bet intrabodies to prevent T-bet activity in cells, for example, in an in vivo or ex vivo approach, for which the cells are modified to express such intrabodies. In a particular embodiment, the T-bet intrabodies of the invention can be used to directly inhibit T-bet activity. In another embodiment, the T-bet intrabodies can be used to inhibit the interaction of T-bet and a protein with which T-bet interacts. Thus, the T-bet intrabodies of the invention are useful in modulating signaling pathways in which T-bet is involved.

The T-bet intrabodies can be prepared using techniques known in the art. For example, phage display technology can be used to isolate scFvs from libraries (Lowman, H B et al. (1991) *Biochemistry* 30(10): 832-8). To select scFvs binding to a particular antigen, the scFvs are fused to a coat protein, typically pIII (g3p) of filamentous M13 phage. An scFv on the phage that binds an immobilized antigen is enriched during consecutive cycles of binding, elution and amplification. In another example, ribosome display can used to prepare T-bet intrabodies (Hanes, J. et al. (1997) *Proc. Natl. Acad. Sci.* 94(1): 937-44). Ribosome display is an in vitro method that links the peptide directly to the genetic information (mRNA). An scFv cDNA library is expressed in vitro using a transcription translation system. The translated ScFvs are stalled to the ribosome linked to the encoding mRNA. The scFv is then bound to the immobilized antigen and unspecific ribosome complexes are removed by extensive washes. The remaining complexes are eluted and the RNA is isolated, reverse transcribed to cDNA and subsequently re-amplified by PCR. In yet another example, a Protein Fragment Complementation Assay (PCA) can be used to prepare T-bet intrabodies of the invention (Pelletier, J N et al. (1998) *Proc. Natl. Acad. Sci.* 95(12): 141-6.) This is a cellular selection procedure based on the complementation of a mutant dihydrofolate reductase (DHFR) in *E. coli* by the mouse protein (mDHFR). The murine DHFR is dissected into two parts, which are expressed as fusion proteins with potentially interacting peptides. The interaction of the fusion proteins restores the enzymatic activity of mDHFR, and thus bacterial proliferation. Only a specific interaction of antibody and antigen allows the functional complementation of DHFR which makes the system amenable for the selection of scFvs (Mossner, E. et al. (2001) *Mol Biol* 308:115-22).

IV. Methods of the Invention

A. Detection of T-bet Compositions

Another aspect of the invention pertains to methods of using the various T-bet compositions of the invention. For example, the invention provides a method for detecting the presence of T-bet activity in a biological sample. The method involves contacting the biological sample with an agent capable of detecting T-bet activity, such as T-bet protein or T-bet mRNA, such that the presence of T-bet activity is detected in the biological sample.

A preferred agent for detecting T-bet mRNA is a labeled nucleic acid probe capable of specifically hybridizing to T-bet mRNA. The nucleic acid probe can be, for example, the T-bet DNA of SEQ ID NO: 1 or 3, such as an oligonucleotide of at least about 500, 600, 800, 900, 1000, 1200, 1400, or 1600 nucleotides in length and which specifically hybridizes under stringent conditions to T-bet mRNA.

A preferred agent for detecting T-bet protein is a labeled antibody capable of binding to T-bet protein. Antibodies can be polyclonal, or more preferably, monoclonal. An intact antibody, or a fragment thereof (e.g., Fab or F(ab')2) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "biological sample" is intended to include tissues, cells and biological fluids. For example, techniques for detection of T-bet mRNA include Northern hybridizations and in situ hybridizations. Techniques for detection of T-bet protein include enzyme linked immunosorbent assays (ELISAs), Western blots, immunoprecipitations and immunofluorescence.

B. Screening Methods

The invention further provides methods for identifying compounds, i.e., candidate or test compounds or agents (e.g., peptidomimetics, small molecules or other drugs) that modulate, e.g., increase or decrease, P-selectin-mediated T cell rolling and/or stable adherence of a T cell to a vascular endothelial cell in the presence of T-bet. Modulators of P-selectin-mediated T cell rolling and/or stable adherence of a T cell to a vascular endothelial cell can be known (e.g., dominant negative inhibitors of T-bet activity, antisense T-bet, intracellular antibodies that interfere with T-bet activity, peptide inhibitors derived from T-bet), or can be identified using the methods described herein, e.g., have a stimulatory or inhibitory effect on a T-bet biological activity (as described herein), T-bet processing, T-bet post-translational modification (e.g., glycosylation, ubiquitinization, or phosphorylation); or have a stimulatory or inhibitory effect on the expression, processing or activity of a T-bet target molecule.

For example, in one embodiment, molecules which modulate the interaction, e.g., binding, of P-selectin and PSGL-1 in the presence of T-bet, can be identified. For example, TPST-2 tyrosine sulfonates PSGL-1, a post-translational modification necessary for the interaction of P-selectin and PSGL-1, and therefore, any of these molecules can be used in the subject screening assays. Although the specific embodiments described below in this section and in other sections may list one of these molecules as an example, other molecules that interact with and/or are involved in a signal transduction pathway involving T-bet can also be used in the subject screening assays.

In one embodiment, molecules which modulate the interaction, e.g., P-selectin and P-selectin glycoprotein ligand-1 (PSGL-1), in the presence of T-bet can be identified. In another embodiment, the ability of a compound to modulate the stable adherence of a T cell to a vascular endothelial cell in the presence of T-bet are identified. In yet embodiment, the ability of a compound to directly modulate, e.g., increase or stabilize, or decrease or destabilize, the formation of a complex between P-selectin and PSGL-1 in the presence of T-bet is measured. In other embodiments, the post-translational modification (e.g., tyrosine sulfation) of PSGL-1, or the expression and/or activity of T-bet is measured using a screening assay of the invention. In yet another embodiment, the biological activity of T-bet is measured by measuring the binding of T-bet to a regulatory region of a gene responsive to T-bet. In one embodiment, the responsive of a gene to T-bet, e.g., CXCR3, TPST-2, is measured by measuring the expression of the gene. In another embodiment, the biological activity of T-bet is measured by measuring T cell chemotaxis and/or β-integrin dependent binding of a T cell to VCAM-1 on an endothelial cell.

The screening assays of the invention can be performed using a cell that expresses the T-bet protein or a molecule that interacts with T-bet or a molecule in a signal transduction pathway involving T-bet, for example, a cell that naturally expresses or, more preferably, a cell that has been engineered to express the protein by introducing into the cell an expression vector encoding the protein. Preferably, the cell is a mammalian cell, e.g., a human cell. In one embodiment, the cell is a T cell. In one preferred embodiment, the cell a Th1 cell. Alternatively, screening assays can be performed in a cell-free composition that includes the protein (e.g., a cell extract or a composition that includes, e.g., either purified natural or recombinant protein).

The ability of a compound to modulate P-selectin-mediated rolling of T cells can be determined by, for example, measuring the tyrosine sulfation of PSGL-1. For example, post-translation modification of PSGL-1, e.g., tyrosine sulfonation, can be measured by immunoprecipitating proteins of interest from cells grown in the presence of $^{35}$S-sulfate and visualizing by autoradiography. The ability of a compound to modulate P-selectin-mediated rolling of T cells can also be determined by, for example, measuring the expression and/or activity of tyrosyl protein sulfotransferase-2 (TPST-2), by for example, Real-time PCR For example, TPST-2 is a sulfotransferase that sulfonates, e.g., tyrosine sulfonates, target molecules, such as PSGL-1, a post-translation modification which is necessary for PSGL-1 function, e.g., binding to P-selectin in the presence of T-bet, and is thus necessary for P-selectin-mediated rolling of T cells. The ability of a compound to modulate the stable adherence of a T cell to a vascular endothelial cell can be determined by assaying for the modulation of a biological activity of T-bet. For example, as described herein T-bet is required for the expression of the chemokine receptor, CXCR3, and the expression of CXCR3 can be measured by Real-time PCR, or alternatively the expression of CXCR3 can be determined by using a transwell chemotaxis assay. The ability of a compound to modulate the stable adherence of a T cell to a vascular endothelial cell can also be measured by measuring the binding of a T cell to an endothelial cell in an appropriate in vitro cell model, such as unstimulated cardiac endothelial cells in a transwell assay, to measure β-integrin dependent binding of a T cell to VCAM-1 on an endothelial cell. In one embodiment, the ability of the compounds to modulate recruitment of a T cell to a site of inflammation can be measured, by, for example, use of an appropriate in vitro or in vivo model, such as, for example, a T-bet transgenic animal, an IFN-γ transgenic animal or cells therefrom, using for example an adoptive transfer assay and assaying by FACs analysis to determine the number and types of cells at various locations in the animals.

Additionally, the ability of a compound to modulate a biological activity of T-bet can also be determined by, for example, measuring the expression and/or activity of T-bet. For example, T-bet is a transcription factor and, therefore, has the ability to bind to DNA and to regulate expression of genes, e.g., cytokine genes. Accordingly, specific embodiments of the screening methods of the invention exploit the ability of T-bet polypeptides to bind to DNA or other target molecule; (e.g., GATA3, Tec kinase, or IL-2 or IFN-γ promoter); to regulate gene expression (e.g., regulate expression of a Th1-associated cytokine genes, e.g., by repressing the IL-2 gene, transactivating the IFN-γ gene, or to regulate the expression of a Th2-associated cytokine gene, e.g., the IL-4 gene or the IL-10 gene (e.g., by reducing the ability of GATA3 to bind to DNA), or to regulate the expression of other genes, (e.g., by repressing TGF-β or Toll-like receptor genes, such as TLR6)).

In one embodiment, the invention provides methods for identifying modulators, i.e., candidate or test compounds or agents (e.g., enzymes, peptides, peptidomimetics, small molecules, ribozymes, or T-bet antisense molecules) which bind to T-bet polypeptides; have a stimulatory or inhibitory effect on T-bet expression; T-bet processing; T-bet post-translational modification (e.g., glycosylation, ubiquitinization, or phosphorylation); or T-bet activity, or have a stimulatory or inhibitory effect on the expression, processing or activity of a T-bet binding partner or target molecule.

In one preferred embodiment, the invention features a method for identifying a compound which modulates P-selectin-mediated T cell rolling, comprising contacting in the presence of the compound, T-bet, a P-selectin molecule, and a P-selectin glycoprotein ligand-1 (PSGL-1) molecule under conditions which allow interaction of the PSGL-1 molecule with P-selectin; and detecting the interaction of P-selectin and the PSGL-1 molecule, wherein the ability of the compound to inhibit T cell rolling is indicated by a decrease in the interaction as compared to the amount of interaction in the absence of the compound and the ability of the compound to enhance T cell rolling is indicated by an increase in the interaction as compared to the amount of interaction in the absence of the compound.

In another preferred embodiment, the invention features a method of identifying a compound which modulates stable adherence of a T cell to a vascular endothelial cell, comprising:

a) contacting a T cell with a test compound;

b) assaying for modulation of a biological activity of T-bet in the presence of said test compound, wherein a decrease in a biological activity of T-bet by the compound identifies the test compound as a compound that inhibits stable adherence of a T cell to a vascular endothelial cell, and an increase in a biological activity of T-bet by the compound identifies the test compound as a compound that enhances stable adherence of a T cell to a vascular endothelial cell.

Compounds identified using the assays described herein may be useful for treating disorders associated with aberrant T-bet expression, processing, post-translational modification, or activity, aberrant P-selectin-mediated T cell rolling, stable adherence of a T cell to a vascular endothelial cell, recruitment of a T cell to a site of inflammation, T cell lineage commitment, production of cytokines, TGF-β mediated signaling, Jak1/STAT-1 pathway, IgG class switching and aberrant B lymphocyte function.

In one embodiment, the subject screening assays can be performed in the presence or absence of other agents. For example, the subject assays can be performed in the presence various chemokine ligands such as CXCL10 and CXCL11. Agents that modulate the activation state of the cell being screened can also be included. For example, in one embodiment, agents that transduce signals via the T cell receptor are included. In another embodiment, a cytokine or an antibody to a cytokine receptor is included. In another embodiment, an agent that inhibits sulfation, e.g., tyrosine sulfation, can also be included.

In another aspect, the invention pertains to a combination of two or more of the assays described herein. For example, a modulating agent can be identified using a cell-based or a cell-free assay, and the ability of the agent to modulate P-selectin-mediated T cell rolling, stable adherence of a T cell to a vascular endothelial cell, and/or recruitment of a T cell to a site of inflammation can be confirmed in vivo, e.g., in an animal such as an animal model for multiple sclerosis (RAE), rheumatoid arthritis, or infection.

Moreover, a modulator of P-selectin-mediated T cell rolling, stable adherence of a T cell to a vascular endothelial cell, and/or recruitment of a T cell to a site of inflammation identified as described herein (e.g., a dominant negative T-bet molecule, a T-bet nucleic acid or polypeptide molecule, an antisense T-bet nucleic acid molecule, a T-bet-specific antibody, or a small molecule) can be used in an animal model to determine the efficacy, toxicity, or side effects of treatment with such a modulator. Alternatively, a modulator identified as described herein can be used in an animal model to determine the mechanism of action of such a modulator.

In another embodiment, it will be understood that similar screening assays can be used to identify compounds that indirectly modulate T-bet expression and/or activity, e.g., by performing screening assays such as those described above, but employing molecules with which T-bet interacts, i.e., molecules that act either upstream or downstream of T-bet in a signal transduction pathway, such as a Tec kinase.

The cell based and cell free assays of the invention are described in more detail below.

i. Cell Based Assays

The screening assays of the invention can be performed in a cell that expresses a T-bet polypeptide (and/or one or more non-T-bet polypeptides such as a P-selectin, PSGL-1, CXCR3, CXCL10, CXCL11, β-integrin, VCAM-1), for example, a cell that naturally expresses endogenous T-bet or, more preferably, a cell that has been engineered to express an exogenous T-bet polypeptide by introducing into the cell an expression vector encoding the polypeptide. Alternatively, the indicator composition can be a cell-free composition that includes T-bet and/or one or more non-T-bet polypeptides such as a P-selectin, PSGL-1, CXCR3, CXCL10, CXCL11, β-integrin, VCAM-1 (e.g., a cell extract from a T-bet-expressing cell or a composition that includes purified T-bet, either natural or recombinant polypeptide).

Compounds that modulate P-selectin-mediated T cell rolling, stable adherence of a T cell to a vascular endothelial cell, and/or recruitment of a T cell to a site of inflammation can be identified using various "read-outs."

For example, an indicator cell can be transfected with a T-bet expression vector, incubated in the presence and in the absence of a test compound, and the effect of the compound on the expression of the molecule or on a biological response regulated by T-bet can be determined. The biological activities of T-bet include activities determined in vivo, or in vitro, according to standard techniques. A T-bet activity can be a direct activity, such as an association of T-bet with a T-bet-target molecule (e.g. a nucleic acid molecule to which T-bet binds such as the transcriptional regulatory region of a cytokine gene. A T-bet activity can also be the requirement of T-bet for the expression of a gene such as a chemokine gene, e.g., CXCR3, or TPST-2 or the post-translational modification of a target gene, such a tyrosine sulfation of, for example, PSGL-1. Alternatively, a T-bet activity is a downstream activity, such as a cellular signaling activity occurring downstream of the interaction of the T-bet polypeptide with a T-bet target molecule or a biological effect occurring as a result of the signaling cascade triggered by that interaction. For example, biological activities of T-bet described herein include: modulation of P-selectin-mediated T cell rolling, modulation of stable adherence of a T cell to a vascular endothelial cell, modulation of recruitment of a T cell to a site of inflammation, modulation of T cell lineage commitment, e.g., directly modulate, modulating the production of cytokines, modulating TGF-β mediated signaling, modulating the Jak1/STAT-1 pathway, modulating IgG class switching and modulating B lymphocyte function. The various biological activities of T-bet can be measured using techniques that are known in the art. Exemplary techniques are described in more detail in the Examples.

To determine whether a test compound modulates T-bet expression, in vitro transcriptional assays can be performed. To perform such an assay, the full length promoter and enhancer of T-bet can be operably linked to a reporter gene such as chloramphenicol acetyltransferase (CAT) or luciferase and introduced into host cells.

As used interchangeably herein, the terms "operably linked" and "operatively linked" are intended to mean that the nucleotide sequence is linked to a regulatory sequence in a manner which allows expression of the nucleotide sequence in a host cell (or by a cell extract). Regulatory sequences are art-recognized and can be selected to direct expression of the desired polypeptide in an appropriate host cell. The term regulatory sequence is intended to include promoters, enhancers, polyadenylation signals and other expression control elements. Such regulatory sequences are known to those skilled in the art and are described in Goeddel, *Gene Expression Technology: Methods in Enzymology* 185, Academic Press, San Diego, Calif. (1990). It should be understood that the design of the expression vector may depend on such factors as the choice of the host cell to be transfected and/or the type and/or amount of polypeptide desired to be expressed.

A variety of reporter genes are known in the art and are suitable for use in the screening assays of the invention. Examples of suitable reporter genes include those which encode chloramphenicol acetyltransferase, beta-galactosidase, alkaline phosphatase or luciferase. Standard methods for measuring the activity of these gene products are known in the art.

A variety of cell types are suitable for use as indicator cells in the screening assay. Preferably a cell line is used which does not normally express T-bet, such as a Th1 cell clone or a cell from a knock out animal, e.g., a T-bet knock-out animal. Nonlymphoid cell lines can also be used as indicator cells, such as the HepG2 hepatoma cell line. Yeast cells also can be used as indicator cells.

The cells used in the instant assays can be eukaryotic or prokaryotic in origin. For example, in one embodiment, the cell is a bacterial cell. In another embodiment, the cell is a fungal cell, e.g., a yeast cell. In another embodiment, the cell is a vertebrate cell, e.g., an avian or a mammalian cell. In a preferred embodiment, the cell is a human cell.

In one embodiment, the level of expression of the reporter gene in the indicator cell in the presence of the test compound is higher than the level of expression of the reporter gene in the indicator cell in the absence of the test compound and the test compound is identified as a compound that stimulates the expression of T-bet. In another embodiment, the level of expression of the reporter gene in the indicator cell in the presence of the test compound is lower than the level of expression of the reporter gene in the indicator cell in the absence of the test compound and the test compound is identified as a compound that inhibits the expression of T-bet.

In one embodiment, the invention provides methods for identifying compounds that modulate cellular responses in which T-bet is involved.

The ability of a test compound to modulate T-bet binding to a target molecule or to bind to T-bet can also be determined.

Determining the ability of the test compound to modulate T-bet binding to a target molecule (e.g. a binding partner) can be accomplished, for example, by coupling the T-bet target molecule with a radioisotope, enzymatic or fluorescent label such that binding of the T-bet target molecule to T-bet can be determined by detecting the labeled T-bet target molecule in a complex. Alternatively, T-bet can be coupled with a radioisotope, enzymatic or fluorescent label to monitor the ability of a test compound to modulate T-bet binding to a T-bet target molecule in a complex. Determining the ability of the test compound to bind T-bet can be accomplished, for example, by coupling the compound with a radioisotope, enzymatic or fluorescent label such that binding of the compound to T-bet can be determined by detecting the labeled T-bet compound in a complex. For example, T-bet targets can be labeled with $^{125}I$, $^{35}S$, $^{14}C$, or 3H, either directly or indirectly, and the radioisotope detected by direct counting of radioemmission or by scintillation counting. Alternatively, compounds can be enzymatically labeled with, for example, horseradish peroxidase, alkaline phosphatase, or luciferase, and the enzymatic label detected by determination of conversion of an appropriate substrate to product.

It is also within the scope of this invention to determine the ability of a compound to interact with T-bet without the labeling of any of the interactants. For example, a microphysiometer can be used to detect the interaction of a compound with T-bet without the labeling of either the compound or the T-bet (McConnell, H. M. et al. (1992) *Science* 257:1906-1912). As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between a compound and T-bet.

In another embodiment, a different (i.e., non-T-bet) molecule acting in a pathway involving T-bet that acts upstream or downstream of T-bet can be included in an indicator composition for use in a screening assay. Compounds identified in a screening assay employing such a molecule would also be useful in modulating T-bet activity, albeit indirectly. An exemplary molecule with which T-bet interacts includes a CXCL10, CXCL11.

The cells of the invention can express endogenous T-bet (or another polypeptide in a signaling pathway involving T-bet) or may be engineered to do so. A cell that has been engineered to express the T-bet polypeptide or a non T-bet polypeptide which acts upstream or downstream of T-bet can be produced by introducing into the cell an expression vector encoding the T-bet polypeptide or a non T-bet polypeptide which acts upstream or downstream of T-bet.

Recombinant expression vectors that can be used for expression of T-bet polypeptide or a non T-bet polypeptide which acts upstream or downstream of T-bet in the indicator cell are known in the art. In one embodiment, within the expression vector the T-bet-coding sequences are operatively linked to regulatory sequences that allow for inducible or constitutive expression of T-bet in the indicator cell (e.g., viral regulatory sequences, such as a cytomegalovirus promoter/enhancer, can be used). Use of a recombinant expression vector that allows for inducible or constitutive expression of T-bet in the indicator cell is preferred for identification of compounds that enhance or inhibit the activity of T-bet. In an alternative embodiment within the expression vector the T-bet-coding sequences are operatively linked to regulatory sequences of the endogenous T-bet gene (i.e., the promoter regulatory region derived from the endogenous T-bet gene). Use of a recombinant expression vector in which T-bet expression is controlled by the endogenous regulatory sequences is preferred for identification of compounds that enhance or inhibit the transcriptional expression of T-bet.

In methods in which a Th1-associated cytokine gene is utilized (e.g., as a reporter gene or as a readout to assess T-bet activity), preferably, the Th1-associated cytokine is interferon-γ or IL-2. As described in the appended examples, T-bet was isolated in a yeast one hybrid screening assay based on its ability to bind to the IL2 promoter. Accordingly, in one embodiment, a method of the invention utilizes a reporter gene construct containing this region of the proximal IL-2 promoter, most preferably nucleotides -240 to -220 of the IL2 promoter. Other sequences that can be employed include: the consensus T-box site, the human IL-2 promoter, the murine 12 promoter, the human IFN-γ intron III, two binding sites in the murine IFN-γ proximal promoter. (Szabo et al. 2000. *Cell* 100:655-669).

In one embodiment, an inducible system can be constructed and used in high throughput cell-based screens to identify and characterize target compounds that affect the expression and/or activity of T-bet. The inducible system can be constructed using a cell line that does not normally produce IFN-γ, for example, by using a subclone of the adherent 293T human embryonic kidney cell line that expresses the ecdysone receptor, co-transfected with an ecdysone-driven T-bet expression plasmid, and an IFN-γ promoter luciferase reporter. (Wakita et al. 2001. Biotechniques 31:414; No et al. Proceedings of the National Academy of Sciences USA 93:3346; Graham. 2002 Expert Opin. Biol. Ther. 2:525). Upon treatment with the insect hormone ecdysone, T-bet is expressed, the IFN-γ reporter is activated and luciferase activity is generated. In this system, T-bet confers on the cell line the ability to produce endogenous IFN-γ.

ii. Cell-Free Assays

In another embodiment, the screening assays are performed in a cell free composition. T-bet or a non-T-bet polypeptide which acts upstream or downstream of T-bet in a pathway involving T-bet expressed by recombinant methods in a host cells or culture medium can be isolated from the host cells, or cell culture medium using standard methods for purifying polypeptides, for example, by ion-exchange chromatography, gel filtration chromatography, ultrafiltration, electrophoresis, and immunoaffinity purification with antibodies specific for T-bet to produce protein that can be used in a cell free composition. Alternatively, an extract of T-bet or non-T-bet expressing cells can be prepared for use as cell-free composition.

In one embodiment, compounds that specifically modulate T-bet activity are identified based on their ability to modulate the interaction of T-bet with a target molecule to which T-bet binds. The target molecule can be a DNA molecule, e.g., a T-bet-responsive element, such as the regulatory region of a cytokine gene) or a polypeptide molecule. Suitable assays are known in the art that allow for the detection of protein-protein interactions (e.g., immunoprecipitations, fluorescent polarization or energy transfer, two-hybrid assays and the like) or that allow for the detection of interactions between a DNA binding protein with a target DNA sequence (e.g., electrophoretic mobility shift assays, DNAse I footprinting assays and the like). By performing such assays in the presence and absence of test compounds, these assays can be used to identify compounds that modulate (e.g., inhibit or enhance) the interaction of T-bet with a target molecule.

In one embodiment, the amount of binding of T-bet to the target molecule in the presence of the test compound is greater than the amount of binding of T-bet to the target molecule in the absence of the test compound, in which case the test compound is identified as a compound that enhances or stabilizes binding of T-bet. In another embodiment, the amount of binding of the T-bet to the target molecule in the presence of the test compound is less than the amount of binding of the T-bet to the target molecule in the absence of the test compound, in which case the test compound is identified as a compound that inhibits or destabilizes binding of T-bet.

Binding of the test compound to the T-bet polypeptide can be determined either directly or indirectly as described above. Determining the ability of the T-bet polypeptide to bind to a test compound can also be accomplished using a technology such as real-time Biomolecular Interaction Analysis (BIA) (Sjolander, S, and Urbaniczky, C. (1991) *Anal. Chem.* 63:2338-2345; Szabo et al. (1995) *Curr. Opin. Struct. Biol.* 5:699-705). As used herein, "BIA" is a technology for studying biospecific interactions in real time, without labeling any of the interactants (e.g., BIAcore). Changes in the optical phenomenon of surface plasmon resonance (SPR) can be used as an indication of real-time reactions between biological molecules.

In the methods of the invention for identifying test compounds that modulate an interaction between T-bet polypeptide and a target molecule, the full-length T-bet polypeptide may be used in the method, or, alternatively, a polypeptide comprising one or more portion of the T-bet may be used. The degree of interaction between T-bet polypeptides and the target molecule can be determined, for example, by labeling one of the polypeptides with a detectable substance (e.g., a radiolabel), isolating the non-labeled polypeptide and quantitating the amount of detectable substance that has become associated with the non-labeled polypeptide. The assay can be used to identify test compounds that either stimulate or inhibit the interaction between the T-bet protein and a target molecule. A test compound that stimulates the interaction between the T-bet polypeptide and a target molecule is identified based upon its ability to increase the degree of interaction between the T-bet polypeptide and a target molecule as compared to the degree of interaction in the absence of the test compound. A test compound that inhibits the interaction between the T-bet polypeptide and a target molecule is identified based upon its ability to decrease the degree of interaction between the T-bet polypeptide and a target molecule as compared to the degree of interaction in the absence of the compound.

In more than one embodiment of the above assay methods of the present invention, it may be desirable to immobilize either T-bet or a T-bet target molecule, a kinase, for example, to facilitate separation of complexed from uncomplexed forms of one or both of the polypeptides, or to accommodate automation of the assay. Binding of a test compound to a T-bet polypeptide, or interaction of a T-bet polypeptide with a T-bet target molecule in the presence and absence of a test compound, can be accomplished in any vessel suitable for containing the reactants. Examples of such vessels include microtitre plates, test tubes, and micro-centrifuge tubes. In one embodiment, a fusion protein can be provided which adds a domain that allows one or both of the polypeptides to be bound to a matrix. For example, glutathione-S-transferase/T-bet fusion proteins or glutathione-S-transferase/target fusion proteins can be adsorbed onto glutathione sepharose beads (Sigma Chemical, St. Louis, Mo.) or glutathione derivatized microtitre plates, which are then combined with the test compound and either the non-adsorbed target polypeptide or T-bet polypeptide, and the mixture incubated under conditions conducive to complex formation (e.g., at physiological conditions for salt and pH). Following incubation, the beads or microtitre plate wells are washed to remove any unbound components, the matrix is immobilized in the case of beads, and complex formation is determined either directly or indirectly, for example, as described above. Alternatively, the complexes can be dissociated from the matrix, and the level of T-bet binding or activity determined using standard techniques.

Other techniques for immobilizing polypeptides on matrices can also be used in the screening assays of the invention. For example, either a T-bet polypeptide or a T-bet target molecule can be immobilized utilizing conjugation of biotin and streptavidin. Biotinylated T-bet polypeptide or target molecules can be prepared from biotin-NHS (N-hydroxy-succinimide) using techniques known in the art (e.g., biotinylation kit, Pierce Chemicals, Rockford, Ill.), and immobilized in the wells of streptavidin-coated 96 well plates (Pierce Chemical). Alternatively, antibodies which are reactive with T-bet polypeptide or target molecules but which do not interfere with binding of the T-bet polypeptide to its target molecule can be derivatized to the wells of the plate, and unbound target or T-bet polypeptide is trapped in the wells by antibody conjugation. Methods for detecting such complexes, in addition to those described above for the GST-immobilized complexes, include immunodetection of complexes using antibodies reactive with the T-bet polypeptide or target molecule, as well as enzyme-linked assays which rely on detecting an enzymatic activity associated with the T-bet polypeptide or target molecule.

In yet another aspect of the invention, the T-bet polypeptide or fragments thereof can be used as "bait proteins" in a two-hybrid assay or three-hybrid assay (see, e.g., U.S. Pat. No. 5,283,317; Zervos et al. (1993) *Cell* 72:223-232; Madura et al. (1993) *J. Biol. Chem.* 268:12046-12054; Bartel et al. (1993) *Biotechniques* 14:920-924; Iwabuchi et al. (1993) *Oncogene* 8:1693-1696; and Brent WO94/10300), to identify other polypeptides, which bind to or interact with T-bet ("T-bet-binding proteins" or "T-bet") and are involved in T-bet activity. Such T-bet-binding proteins are also likely to be involved in the propagation of signals by the T-bet polypeptides or T-bet targets as, for example, downstream elements of a T-bet-mediated signaling pathway. Alternatively, such T-bet-binding polypeptides are likely to be T-bet inhibitors.

The two-hybrid system is based on the modular nature of most transcription factors, which consist of separable DNA-binding and activation domains. Briefly, the assay utilizes two different DNA constructs. In one construct, the gene that codes for a T-bet polypeptide is fused to a gene encoding the DNA binding domain of a known transcription factor (e.g., GAL 4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a T-bet-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the polypeptide which interacts with the T-bet polypeptide.

In another embodiment, representational difference analysis (RDA) and microchip DNA array analysis to isolate T-bet target genes. For example, differential display or subtraction methods coupled with PCR (RDA; see e.g., Hubank, M. & Schatz, D. G. 1994. *Nuc. Acid Res.* 22, 5640-5648; Chang, Y., et al. 1994. *Science* 266, 1865; von Stein, O. D., et al. 1997. *Nuc. Acid Res.* 25, 2598; Lisitsyn, N. & Wigler, M. 1993. *Science* 259, 946) employing subtracted or unsubtracted probes or, most recently, DNA microchip array hybridization (Welford et al. 1998. Nucl. Acids. Res. 15:3059) can be used. In performing such assays, a variety of cells can be used, e.g. normal cells, cells engineered to express T-bet, or cells from mice lacking T-bet or overexpressing T-bet (e.g., from a transgenic non-human animal) can be used.

In yet another embodiment, proteomic approaches to describe T-bet target proteins can be performed. For example, subtractive analysis, analysis of expression patterns, identification of genotypic variations at the protein level and protein identification and detection of post-translational modifications can be performed as described in, e.g., Wang et al. (2002) *J. Chromatogr. B. Technol. Biomed Life Sci.* 782(1-2): 291-306; Lubman et al. (2002) *J. Chromatogr. B. Technol. Biomed Life Sci.* 782(1-2): 183-96; and Rai et al. (2002) *Arch. Pathol. Lab. Med.* 126(12):1518-26.

C. Assays Using T-bet Deficient Cells

In another embodiment, the invention provides methods for identifying compounds that modulate a biological effect of T-bet using cells deficient in T-bet. As described herein, cells deficient in T-bet (e.g., by disruption of the T-bet gene) have a reduction in PSGL-1 tyrosine sulfation and tyrosyl protein sulfotransferase-1 (TPST-1) expression, as well a reduction of CXCR3 expression, reduced binding to P-selectin, and do not attach or migrate in response to appropriate stimuli. Thus, cells deficient in T-bet can be used identify agents that modulate a biological response regulated by T-bet by means other than modulating T-bet itself (i.e., compounds that "rescue" the T-bet deficient phenotype). Alternatively, a "conditional knock-out" system, in which the T-bet gene is rendered non-functional in a conditional manner, can be used to create T-bet deficient cells for use in screening assays. For example, a tetracycline-regulated system for conditional disruption of a gene as described in WO 94/29442 and U.S. Pat. No. 5,650,298 can be used to create cells, or T-bet deficient animals from which cells can be isolated, that can be rendered T-bet deficient in a controlled manner through modulation of the tetracycline concentration in contact with the cells. For assays relating to other biological effects of T-bet a similar conditional disruption approach can be used or, alternatively, the RAG-2 deficient blastocyst complementation system can be used to generate mice with lymphoid organs that arise from embryonic stem cells with homozygous mutations of the T-bet gene. T-bet deficient lymphoid cells (e.g. thymic, splenic and/or lymph node cells) or purified T-bet deficient B cells from such animals can be used in screening assays.

In the screening method, cells deficient in T-bet are contacted with a test compound and a biological response regulated by T-bet is monitored. Modulation of the response in T-bet deficient cells (as compared to an appropriate control such as, for example, untreated cells or cells treated with a control agent) identifies a test compound as a modulator of the T-bet regulated response.

In one embodiment, the test compound is administered directly to a non-human T-bet deficient animal, preferably a mouse (e.g., a mouse in which the T-bet gene is conditionally disrupted by means described above, or a chimeric mouse in which the lymphoid organs are deficient in T-bet as described above), to identify a test compound that modulates the in vivo responses of cells deficient in T-bet. In another embodiment, cells deficient in T-bet are isolated from the non-human T-bet deficient animal, and contacted with the test compound ex vivo to identify a test compound that modulates a response regulated by T-bet in the cells deficient in T-bet.

Cells deficient in T-bet can be obtained from a non-human animals created to be deficient in T-bet. Preferred non-human animals include monkeys, dogs, cats, mice, rats, cows, horses, goats and sheep. In preferred embodiments, the T-bet deficient animal is a mouse. Mice deficient in T-bet can be made as described in the Examples. Non-human animals deficient in a particular gene product typically are created by homologous recombination. Briefly, a vector is prepared which contains at least a portion of the T-bet gene into which a deletion, addition or substitution has been introduced to thereby alter, e.g., functionally disrupt, the endogenous T-bet gene. The T-bet gene preferably is a mouse T-bet gene. For example, a mouse T-bet gene can be isolated from a mouse genomic DNA library using the mouse T-bet cDNA as a probe. The mouse T-bet gene then can be used to construct a homologous recombination vector suitable for altering an endogenous T-bet gene in the mouse genome. In a preferred embodiment, the vector is designed such that, upon homologous recombination, the endogenous T-bet gene is functionally disrupted (i.e., no longer encodes a functional polypeptide; also referred to as a "knock out" vector). Alternatively, the vector can be designed such that, upon homologous recombination, the endogenous T-bet gene is mutated or otherwise altered but still encodes functional polypeptide (e.g. the upstream regulatory region can be altered to thereby alter the expression of the endogenous T-bet polypeptide). In the homologous recombination vector, the altered portion of the T-bet gene is flanked at its 5' and 3' ends by additional nucleic acid of the T-bet gene to allow for homologous recombination to occur between the exogenous T-bet gene carried by the vector and an endogenous T-bet gene in an embryonic stem cell. The additional flaking T-bet nucleic acid is of sufficient length for successful homologous recombination with the endogenous gene. Typically, several kilobases of flanking DNA (both at the 5' and 3' ends) are included in the vector (see e.g., Thomas, K. R. and Capecchi, M. R. (1987) *Cell* 51:503 for a description of homologous recombination vectors). The vector is introduced into an embryonic stem cell line (e.g., by electroporation) and cells in which the introduced T-bet gene has homologously recombined with the endogenous T-bet gene are selected (see e.g., Li, E. et al. (1992) *Cell* 69:915). The selected cells are then injected into a blastocyst of an animal (e.g. a mouse) to form aggregation chimeras (see e.g., Bradley, A. in *Teratocarcinomas and Embryonic Stem Cells: A Practical Approach*, E. J. Robertson, ed. (IRL, Oxford, 1987) pp. 113-152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described ether in Bradley, A. (1991) *Current Opinion in Biotechnology* 2:823-829 and in PCT International Publication Nos.: WO 90/11354 by Le Mouellec et al.; WO 91/01140 by Smithies et al.; WO 92/0968 by Zijlstra et al.; and WO 93/04169 by Berns et al.

In another embodiment, retroviral transduction of donor bone marrow cells from both wild type and T-bet null mice can be performed with the DN or dominant negative constructs to reconstitute irradiated RAG recipients. This will result in the production of mice whose lymphoid cells express only a dominant negative version of T-bet. B cells from these mice can then be tested for compounds that modulate a biological response regulated by T-bet.

In one embodiment of the screening assay, compounds tested for their ability to modulate a biological response regulated by T-bet are contacted with T-bet deficient cells by administering the test compound to a non-human T-bet deficient animal in vivo and evaluating the effect of the test compound on the response in the animal. The test compound can be administered to a non-human T-bet deficient animal as a pharmaceutical composition. Such compositions typically comprise the test compound and a pharmaceutically acceptable carrier. As used herein the term "pharmaceutically acceptable carrier" is intended to include any and all solvents, dispersion media, coatings, antibacterial and antifungal compounds, isotonic and absorption delaying compounds, and the like, compatible with pharmaceutical administration. The use of such media and compounds for pharmaceutically active substances is well known in the art. Except insofar as any conventional media or compound is incompatible with the active compound, use thereof in the compositions is contemplated. Supplementary active compounds can also be incorporated into the compositions.

D. Test Compounds

A variety of test compounds can be evaluated using the screening assays described herein. In certain embodiments, the compounds to be tested can be derived from libraries (i.e., are members of a library of compounds). While the use of libraries of peptides is well established in the art, new techniques have been developed which have allowed the production of mixtures of other compounds, such as benzodiazepines (Bunin et al. (1992). *J. Am. Chem. Soc.* 114:10987; DeWitt et al. (1993). *Proc. Natl. Acad. Sci. USA* 90:6909) peptoids (Zuckermann. (1994). *J. Med. Chem.* 37:2678) oligocarbamates (Cho et al. (1993). *Science.* 261:1303-), and hydantoins (DeWitt et al. supra). An approach for the synthesis of molecular libraries of small organic molecules with a diversity of 104-105 as been described (Carell et al. (1994). *Angew. Chem. Int. Ed. Engl.* 33:2059-; Carell et al. (1994) *Angew. Chem. Int. Ed. Engl.* 33:2061-).

The compounds of the present invention can be obtained using any of the numerous approaches in combinatorial library methods known in the art, including: biological libraries; spatially addressable parallel solid phase or solution phase libraries, synthetic library methods requiring deconvolution, the 'one-bead one-compound' library method, and synthetic library methods using affinity chromatography selection. The biological library approach is limited to peptide libraries, while the other four approaches are applicable to peptide, non-peptide oligomer or small molecule libraries of compounds (Lam, K. S. (1997) *Anticancer Compound Des.* 12:145). Other exemplary methods for the synthesis of molecular libraries can be found in the art, for example in: Erb et al. (1994). *Proc. Natl. Acad. Sci. USA* 91:11422-; Horwell et al. (1996) *Immunopharmacology* 33:68-; and in Gallop et al. (1994); *J. Med. Chem.* 37:1233-.

Libraries of compounds may be presented in solution (e.g., Houghten (1992) *Biotechniques* 13:412-421), or on beads (Lam (1991) *Nature* 354:82-84), chips (Fodor (1993) *Nature* 364:555-556), bacteria (Ladner U.S. Pat. No. 5,223,409), spores (Ladner U.S. Pat. No. '409), plasmids (Cull et al. (1992) *Proc Natl Acad Sci USA* 89:1865-1869) or on phage (Scott and Smith (1990) *Science* 249:386-390); (Devlin (1990) *Science* 249:404-406); (Cwirla et al. (1990) *Proc. Natl. Acad. Sci.* 87:6378-6382); (Felici (1991) *J. Mol. Biol.* 222:301-310); In still another embodiment, the combinatorial polypeptides are produced from a cDNA library.

Exemplary compounds which can be screened for activity include, but are not limited to, peptides, nucleic acids, carbohydrates, small organic molecules, and natural product extract libraries.

Candidate/test compounds include, for example, 1) peptides such as soluble peptides, including Ig-tailed fusion peptides and members of random peptide libraries (see, e.g., Lam, K. S. et al. (1991) *Nature* 354:82-84; Houghten, R. et al. (1991) *Nature* 354:84-86) and combinatorial chemistry-derived molecular libraries made of D- and/or L-configuration amino acids; 2) phosphopeptides (e.g., members of random and partially degenerate, directed phosphopeptide libraries, see, e.g., Songyang, Z. et al. (1993) *Cell* 72:767-778); 3) antibodies (e.g., polyclonal, monoclonal, humanized, anti-idiotypic, chimeric, and single chain antibodies as well as Fab, F(ab')$_2$, Fab expression library fragments, and epitope-binding fragments of antibodies); 4) small organic and inorganic molecules (e.g., molecules obtained from combinatorial and natural product libraries); 5) enzymes (e.g., endoribonucleases, hydrolases, nucleases, proteases, synthatases, isomerases, polymerases, kinases, phosphatases, oxido-reductases and ATPases), and 6) mutant forms or T-bet molecules, e.g., dominant negative mutant forms of the molecules.

The test compounds of the present invention can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to peptide libraries, while the other four approaches are applicable to peptide, non-peptide oligomer or small molecule libraries of compounds (Lam, K. S. (1997) *Anticancer Compound Des.* 12:145).

Examples of methods for the synthesis of molecular libraries can be found in the art, for example in: DeWitt et al. (1993) *Proc. Natl. Acad. Sci. U.S.A.* 90:6909; Erb et al. (1994) *Proc. Natl. Acad. Sci. USA* 91:11422; Zuckermann et al (1994) *J. Med. Chem.* 37:2678; Cho et al. (1993) *Science* 261:1303; Carell et al. (1994) *Angew. Chem. Int. Ed. Engl.* 33:2059; Carell et al. (1994) *Angew. Chem. Int. Ed. Engl.* 33:2061; and Gallop et al. (1994) *J. Med. Chem.* 37:1233.

Libraries of compounds may be presented in solution (e.g., Houghten (1992) *Biotechniques* 13:412-421), or on beads (Lam (1991) *Nature* 354:82-84), chips (Fodor (1993) *Nature* 364:555-556), bacteria (Ladner U.S. Pat. No. 5,223,409), spores (Ladner U.S. Pat. No. '409), plasmids (Cull et al. (1992) *Proc Natl Acad Sci USA* 89:1865-1869) or phage (Scott and Smith (1990) *Science* 249:386-390; Devlin (1990) *Science* 249:404-406; Cwirla et al. (1990) *Proc. Natl. Acad. Sci.* 87:6378-6382; Felici (1991) *J. Mol. Biol.* 222:301-310; Ladner supra.).

Compounds identified in the subject screening assays can be used in methods of modulating one or more of the biological responses regulated by T-bet. It will be understood that it may be desirable to formulate such compound(s) as pharmaceutical compositions (described supra) prior to contacting them with cells.

Once a test compound is identified that directly or indirectly modulates T-bet expression and/or activity, by one of the variety of methods described hereinbefore, the selected test compound (or "compound of interest") can then be further evaluated for its effect on cells, for example by contacting the compound of interest with cells either in vivo (e.g., by administering the compound of interest to a subject) or ex vivo (e.g. by isolating cells from the subject and contacting the isolated cells with the compound of interest or, alternatively, by contacting the compound of interest with a cell line) and determining the effect of the compound of interest on the cells, as compared to an appropriate control (such as untreated cells or cells treated with a control compound, or carrier, that does not modulate the biological response). Compounds of interest can also be identified using structure based drug design using techniques known in the art.

The instant invention also pertains to compounds identified in the above assays.

V. Kits of the Invention

Another aspect of the invention pertains to kits for carrying out the screening assays of the invention. For example, a kit for carrying out a screening assay of the invention can include a T-bet-containing indicator composition, means for measuring a readout (e.g., polypeptide secretion) and instructions for using the kit to identify modulators of biological effects of T-bet. In another embodiment, a kit for carrying out a screening assay of the invention comprises T-bet deficient cells, means for measuring the readout and instructions for using the kit to identify modulators of a biological effect of T-bet.

This invention is further illustrated by the following example, which should not be construed as limiting. The contents of all references, patents and published patent applications cited throughout this application are hereby incorporated by reference. Additionally, all nucleotide and amino acid sequences deposited in public databases referred to herein are also hereby incorporated by reference.

A nucleic acid molecule comprising a mouse T-bet cDNA cloned into the EcoRI site of the pJG4-5 vector was deposited with the American Type Culture Collection (Manassas, Va.) on Nov. 9, 1999 and assigned Deposit Number PTA-930. A nucleic acid molecule comprising a human T-bet cDNA (prepared from RNA from the human Th1 clone ROT-10) cloned into the PCR 2.1-TOPO vector was deposited with the American Type Culture Collection (Manassas, Va.) on Jan. 28, 2000 and assigned Deposit Number PTA-1339. Both deposits were made under the provisions of the Budapest Treaty.

EXAMPLES

Example 1

Cloning of a Novel Transcription Factor, T-bet

Since the Th1-specific region of the IL-2 promoter had been well localized (Brombacher, F., et al. 1994. Int. Immunol. 6:189-197.; Rooney, J., et al. 1995. Mol. Cell. Biol. 15, 6299-6310; Lederer, J. A., et al. 1994. J. Immunol. 152, 77-86; Durand, D., et al. 1988. Mol. Cell. Biol. 8, 1715-1724; Hoyos, B., et al. 1989. Science 244, 457-450), a yeast one hybrid approach using an IL-2 promoter-reporter and a cDNA library made from the OF6 Th1 clone was chosen to identify Th1 specific transcription factors. To validate this approach, the Th2-specific region of the IL-4 promoter was expressed in yeast and demonstrated to be transactivated by the introduction of c-Maf, but not by several other transcription factors (e.g. NFAT). C-Maf transactivation did not occur when the c-Maf response element (MARE) was mutated. Thus, the yeast one hybrid approach was utilized.

The EGY48 yeast strain was stably integrated with the IL-2 promoter/histidine construct and transformed with a cDNA library made from an anti-CD3 activated Th1 cell clone, OF6. Of $5.6 \times 10^6$ clones screened, 488 were positive in primary screening. Of the 210 clones tested during the secondary screen, 72 proved to be specific for the IL-2 promoter. To reduce the number of positive clones, we hybridized the yeast clone cDNA with cDNAs that were differentially expressed in Th1 and Th2 cell lines. These Th1-Th2 and Th2-Th1 cDNAs were made using the Clontech PCR select kit, radiolabeled and initially used in a pilot experiment to screen the 16 most strongly positive yeast clones. Of those 16 clones, 8 were positive with the Th1 (PL17) specific cDNA product probe and not with the Th2 (D10) specific cDNA product probe. Representational difference analysis (RDA; e.g., Lisitsyn. 1993. Science. 259:946; O'Neill and Sinclair. 1997. Nucleic Acids Res. 25:2681; Hubank and Schatz. 1994. Nucleic Acids Research. 22:5640; Welford et al. 1998. Nucleic Acids Research. 26:3059) with Th1-Th2 probe on 16 positive clones with control hybridization of the probe to IL-2, IFN-γ and IL-4 was performed. The specificity of the Th1 and Th2 subtracted cDNA probes is demonstrated by their detection of IL-2 and IFN-γ versus IL-4 respectively.

Restriction enzyme analyses and sequencing data revealed that all 8 of the clones were related. They fell into three groupings based on differences in the 5' and 3' untranslated regions, each of these categories representing an independent cDNA molecule. Comparing the sequence of these clones with the NCBI GenBank Sequence Database yielded homology with the T-box family of transcription factors.

Example 2

T-bet Shares a Region of Homology with the T-Box Family Memebers T-Brain and Eomesodermin Brachyury or T is the founding member of a family of transcription factors that share a 200 amino acid DNA-binding domain called the T-box (reviewed in (Smith, J. 1997. Current Opinion in Genetics & Development 7, 474-480; Papaioannou, and Silver. 1998. Bioessay. 20:9; Meisler, M. H. 1997. Mammalian Genome 8, 799-800.). The Brachyury (Greek for 'short tail') mutation was first described in 1927 in heterozygous mutant animals who had a short, slightly kinked tail (Herrmann, B. G., 1990. Nature 343, 617-622). There are now eight T-box genes in the mouse not including Brachyury. These include Tbx1-6, T-brain-1 (Tbr-1) and now, T-bet, each with a distinct and usually complex expression pattern. The T-box family of transcription factors is defined by homology of family members in the DNA binding domain. The T-bet DNA binding domain (residues 138-327 of murine T-bet) is most similar to the T-box domains of murine T-brain and *Xenopus* eomesodermin and thus places T-bet in the Tbr1 subfamily of the T-box gene family. The human homologue of the murine T-bet protein is approximately 88% identical to the mouse T-bet T-bet shares a region of homology with the T-box family members T-brain and eomesodermin. The murine T-bet DNA binding domain is most similar to the T-box domains of murine T-brain and *Xenopus* eomesodermin. There is approximately 69% amino acid identity between the three T-box regions. T-bet bears no sequence homology to other T-box family members outside of the T-box domain.

The following materials and methods were used in Example 3-6.

Mice

T-bet$^{-/-}$ mice (Peng, S. L., et al. (2002) *Proc. Natl. Acad. Sci. U.S.A* 99, 5545-5550) were backcrossed onto the BALB/c strain for >10 generations and crossed onto the DO 11.10 TGR-Tg strain. All DO 11.10 mice and DO11.10×T-bet$^{-/-}$ mice were heterozygous for the TCR transgene. T-bet CD2-Tg mice were generated as described and maintained on the BALB/c background (Juedes, A. E., et al. (2004) *J Exp.*

*Med* 199, 1153-1162). BALB/c IFN-$\gamma^{-/-}$ mice (Jackson Laboratories) were crossed with the T-bet$^{-/-}$ strain to generate the T-bet$^{-/-}$×IFN-$\gamma^{-/-}$ strain. Mice were housed in a specific pathogen free barrier unit at the Harvard School of Public Health. Handling of mice and experimental procedures were in accordance with institutional requirements for animal care and use. Mice were used at 4-6 weeks of age.

Cell Preparation.

Primary LN CD4+ T cells were prepared either by positive or negative selection with magnetic beads (MACS, USA) as previously described (Lametschwandtner, G. et al. (2004) *J Allergy Clin. Immunol* 113, 987-994). T cells (>95% pure as assessed by flow cytometry) were stimulated with plate bound anti-CD3 and anti-CD28 antibodies (Pharmingen) or with OVA peptide and syngeneic splenocytes in experiments using cells from DO11.10 animals. Th0, Th1 and Th2 polarising conditions were as previously described (Lametschwandtner, G. et al. (2004) *J Allergy Clin. Immunol* 113, 987-994). T cells were used at day 4-5 following primary stimulation.

Flow Cytometry

Antibodies used were from Pharmingen (BD Biosciences, San Diego, Calif.) except the anti-CXCR3 antibody, which was from R&D systems. Stained cells were acquired on a FACS Calibur (BD Biosciences, San Diego, Calif.) and analyzed with CellQues™ software.

Adoptive Transfer

Adoptive transfers were performed as described (Xie, H., et al. (1999) *J. Exp. Med.* 189, 1765-1776). Briefly, DO 11.10 and DO 11.10×T-bet$^{-/-}$ CD4+ T cells were activated with OVA peptide and BALB/c splenocytes under Th1 or Th2 polarising conditions. Five days after activation, 20×10$^6$ T cells were transferred intravenously into unirradiated BALB/c mice. Twenty-four hours following transfer, recipient mice were injected i.p. with OVA in IFA. Forty-eight hours later, spleen, mesenteric and inguinal LNs were harvested and peritoneal lavage performed. Analysis of in vivo trafficking was performed by staining cells with anti-KJ1-26 (anti-clonotypic) and anti-CD4 antibodies and determining the number and percentage of cells that were double positive for these markers at the various anatomical locations.

Flow Chamber Assays

The interactions of CD4+ T cells with soluble P- and E-selectin were examined under conditions of fluid shear in a parallel plate flow chamber as previously described (Lim, Y. C. et al. (1999) *J. Immunol* 162, 3193-3201). For assessment of chemokine-triggered adhesion to EC, isolated cardiac EC were isolated and used as previously described Lim, Y. C. et al. (2003) *Am J Pathol* 162, 1591-1601).

Sulfation Assays

Assays for tyrosine sulfation were performed as described (Farzan, M. et al. (1999) Cell 96, 667-676). Briefly, CD4+ T cells from WT and T-bet$^{-/-}$ mice were activated under Th1-polarising conditions and transferred to sulfate free medium at day 3 and grown in the presence of [$^{35}$S]-sulfate. 24 hours later, the cells were harvested, treated with peptide:N-glycosidaseF (to remove N-glycans) or neuroaminidase and O-glycosidase (to remove O-glycans) and PSGL-1 was immunoprecipitated (anti-PSGL-1 antibody P2 was from Dr. Bruce Furie, Beth Israel Deaconess Medical Center, Boston, USA) and resolved by SDS-PAGE. Tyrosine sulfation was visualized by autoradiography.

Real Time PCR

Total RNA was extracted from CD4+ T cells with TRIzol solution (Invitrogen, Carlsbarg Calif.) and reverse transcription carried out with the iScript cDNA synthesis kit (Biorad, Hercules Calif.). The amount of amplicon generated was monitored with an Applied Biosystems 7700 (Applied Biosystems, Foster city, CA) apparatus. A specific probe labeled with both a reporter and a quencher dye was added into the Taqman PCR mix (Applied Biosystems) at the beginning of the reaction. The sequences of the primers and Taqman probes used in this study are available on request. Cycle number was normalized to β-actin.

Retroviral Transduction

T-bet and control retroviruses were produced and titred as described (Szabo, S. J. et al. (2000) *Cell* 100, 655-669). CD4+ T cells from WT, T-bet$^{-/-}$ and T-bet$^{-/-}$×IFN-$\gamma^{-/-}$ mice were activated with anti-CD3 and anti-CD28 and spin infected with retrovirus after 36 hours. Fresh medium was added 24 hours later and the cells were either sorted by GFP expression and/or used for flow cytometric and transwell analysis at 5 days.

Transwell Assays

Transwell assays were performed in 24 well plates with 5 μm transwells that had been blocked with fibronectin (Corning, USA). 3×10$^5$ CD4+ T cells were placed in the upper chamber and a dilution of chemokine (Peprotech, USA) was placed in the lower chamber. The cells were placed at 37° C. for 4 hours and transmigration was enumerated by flow cytometry. For the transwell experiments with the retrovirally transduced cells, transmigrated cells were counted by gating on live cells that were also positive for GFP.

Example 3

Reduced In Vivo Migration of T Cells from T-bet$^{-/-}$ Mice

In order to establish whether T-cell migration was impaired in these mice, the recruitment of adoptively transferred CD4+ T cells to a peripheral inflammatory site in vivo was assessed. Firstly, antigen specific TCR transgenic T cells (DO 11.10 and DO 11.10×T-bet$^{-/-}$) were generated in vitro and assessed for the expression of certain well-described adhesion molecules. T-bet$^{-/-}$ Th1 and Th2 cells demonstrated similar levels of expression of PSGL-1, LFA-1 and VLA-4 when compared to wild type cells. Cells generated in this way were injected into unirradiated syngeneic wild-type (WI) mice followed by induction of peritoneal inflammation with their specific T cell antigen (ovalbumin) (Xie, H., et al. (1999) *J. Exp. Med.* 189, 1765-1776). This model allows assessment of trafficking of the transferred cells independent of any defect in effector function that may be present in the T-bet$^{-/-}$ T cells and has been shown to be dependent upon both selectin (Xie, H., et al. (1999) *J. Exp. Med.* 189, 1765-1776) and chemokine mediated interactions (Xie, J. H. et al. (2003) *J Leukoc. Biol.* 73, 771-780). Transfer of DO 11.10 and DO11.10×T-bet$^{-/-}$ CD4+ T cells activated under either Th1 or Th2 polarising conditions revealed unimpaired trafficking of these cells to secondary lymphoid organs in the absence of T-bet since the percentage of transferred T cells in spleen and lymph nodes was similar. Consistent with previously published data (Xie, J. H. et al. (2003) *J Leukoc. Biol.* 73, 771-780), there was substantial trafficking of transferred DO 11.10 CD4+ T cells activated under Th1 conditions to the peritoneum, whereas this migration was abrogated in DO 11.10×T-bet$^{-/-}$ CD4+ T cells demonstrating a profound defect in proinflammatory T cell trafficking.

Example 4

T-bet$^{-/-}$ T Cells Exhibit Impaired Binding to P-Selectin but not E-Selectin

Having observed a defect in migration of T-cells to a peripheral inflammatory site in vivo, it was postulated that T-bet$^{-/-}$ T-lymphocytes might exhibit reduced interactions either with E- and/or P-selectin, or with specific Th1 chemokines. In order to assess this further, the binding of primary wildtype (WT) and T-bet$^{-/-}$ CD4+ T cells that had been activated by ligation of TCR and CD28 under Th1 or Th2 polarising conditions to immobilized recombinant P- and E-selectin under conditions of physiological laminar shear flow was assessed. In the absence of T-bet, Th1 cells displayed markedly reduced binding to P-selectin but normal binding to E-selectin in a shear dependent manner. Th2 cells showed minimal binding to either selectin irrespective of the presence or absence of T-bet. These findings were recapitulated when CD4+ T cells from TCR-transgenic (DO 11.10 vs. DO 11.10×T-bet$^{-/-}$) mice were activated by antigen and antigen-presenting cells. Furthermore, whereas Th1 cell binding was unaffected, Th2 cells from CD2-T-bet transgenic (CD2-Tg mice), a strain that overexpresses T-bet in all T cells, showed a marked increase in P-selectin binding suggesting that T-bet directly effects selectin ligand expression. A small increase in binding of Th2 cells to E-selectin was also noted at low shear although this was considerably less marked than that observed with P-selectin. All P-selectin interactions were blocked by the addition of an anti-PSGL-1 polygonal antibody to the T cells.

Example 5

Impairment of P-Selectin Binding is Due to a Reduction in Tyrosine Sulfation of PSGL-1

As binding to E-selectin was normal (a process critically dependent on fucosylation (Lowe, J. B. (2002) *Immunol Rev.* 186, 19-36)), it was unlikely that carbohydrate modification of PSGL-1 was responsible for the deficit observed in P-selectin binding. The alterations in binding to P-selectin occurred in the context of normal-surface expression of PSGL-1 and the core-2 dependent epitope CD43a, as assessed by flow cytometry (Lim, Y. C., et al. (2001) *J Immunol* 167, 4476-4484; Snapp, K. R., et al. (2001) *Blood* 97, 3806-3811). Using real time RT-PCR, expression of FucTVII mRNA was also similar for WT and T-bet$^{-/-}$ T-cells, thus ruling out a defect in either of these enzymes. Therefore, it was determined whether defects in tyrosine sulfation of PSGL-1 were present in T-bet$^{-/-}$ cells to account for the specific reduction in binding to P-selectin (Wilkins, P. P., et al. (1995) *J Biol. Chem.* 270, 22677-22680). It was found that T-bet$^{-/-}$ CD4+ T cells showed a substantial reduction of PSGL-1 tyrosine sulfation. This reduction was independent of sulfation of glycosyl residues, because the difference in $^{35}$S incorporation persisted even after removal of both O- and N-linked glycans. Expression of tyrosyl protein sulfotransferase-1 (TPST-1) mRNA was the same in both WT and T-bet$^{-/-}$ cells, whereas a 50% reduction in the level of TPST-2 mRNA was observed in T-bet$^{-/-}$ T cells.

Example 6

Expression and Function of CXCR3 but not CCR5 is Impaired in T-bet$^{-/-}$ T Cells In addition to selectin ligand expression, CD4+ Th1 cell migration is dependent on chemokine receptor expression, notably CCR5 and CXCR3. In the absence of T-bet, levels of CXCR3 transcripts were minimal as compared to WT T cells activated under Th1 polarising conditions. These changes were mirrored by surface expression of CXCR3, with no detectable receptor present on the T-bet$^{-/-}$ T cells. In contrast, T-bet CD2-Tg T cells expressed significantly more CXCR3 mRNA than WT T cells when activated under non-polarising or Th2 conditions. Again, the transgenic overexpression of T-bet led to greater surface expression of CXCR3 in these cells. Although these results suggest T-bet may directly regulate expression of CXCR3, its expression has also been reported to be regulated by IFN-γ (Nakajima, C. et al. (2002) *Eur. J Immunol* 32, 1792-1801), a cytokine directly controlled by T-bet. To determine whether the impaired expression of CXCR3 was secondary to the reduced levels of IFN-γ produced by T-bet$^{-/-}$ T cells, T-bet was retrovirally transduced into T-bet$^{-/-}$ and T-bet$^{-/-}$×IFN-γ$^{-/-}$ CD4+ T cells. T-bet transduction into T-bet$^{-/-}$ T cells induced a striking upregulation of CXCR3 mRNA. This induction was entirely independent of IFN-γ production, as marked induction of CXCR3 was seen when T-bet was transduced into T-bet$^{-/-}$×IFN-γ$^{-/-}$ CD4+ T cells. CXCR3 was highly induced on the surface of T-bet$^{-/-}$× IFN-γ$^{-/-}$ CD4+ T cells transduced with T-bet. In marked contrast, levels of CCR5, the other Th1 selective chemokine receptor, were unaffected by the absence of T-bet indicating selective regulation of a Th1 specific chemokine receptor by T-bet. The surface expression of CCR5 was similar on primary CD4+ T cells activated under Th1 polarising conditions on WT, T-bet$^{-/-}$ and T-bet$^{-/-}$×IFN-γ$^{-/-}$ CD4+ T cells, with no detectable CCR5 on T cells of any genotype activated under Th2 polarizing conditions (Table 1).

TABLE 1

CCR5 surface expression (%) and mean fluorescence intensity (MFI) on different genotypes of primary CD4+ cells activated under Th1 or Th2 polarizing conditions.

| Cell Type | CD4+ CCR5+ cells (%) | MFI |
| --- | --- | --- |
| WT Th1 | 7.5 | 464 |
| WT Th2 | <1 | |
| T-bet$^{-/-}$ Th1 | 7.2 | 583 |
| T-bet$^{-/-}$ × IFN-γ$^{-/-}$ Th1 | 5 | 750 |
| T-bet$^{-/-}$ × IFN-γ$^{-/-}$ Th2 | 1.2 | |

Additionally, CCR5 mRNA levels were unchanged in T-bet CD2-Tg T cells. The expression of other chemokine receptors (e.g. CCR4, CXCR4, CCR7) was also unchanged in the absence of T-bet.

The functional absence of CXCR3 was demonstrated by an impaired response to CXCR3 ligands in transwell chemotaxis assays. T-bet$^{-/-}$ T cells failed to migrate in response to the CXCR3 ligand CXCL11 (I-TAC)) or CXCL-10 (IP-10), but migrated comparably to WT CD4+ T cells in response to the CCR5 ligand CCL4 (MIP-1β). T-bet CD2-Tg T cells migrated comparably to WT T cells to MIP-1β under all polarising conditions, showing that transgenic overexpression of T-bet did not directly effect expression of functional CCR5 even under Th2 polarising conditions. Retroviral transduction of T-bet into T-bet$^{-/-}$ and T-bet$^{-/-}$×IFN-γ$^{-/-}$ CD4+ T cells restored transmigration of these cells to the CXCR3 ligands CXCL11 and CXCLIO when compared to transduction with empty retrovirus indicating that T-bet can drive functional expression of CXCR3 by a mechanism independent of its transactivation of the IFN-γ gene.

Chemokines also mediate activation of integrins, resulting in firm adhesion of rolling T-cells (Campbell, J. J. et al. (1998) *Science* 279, 381-384), by inducing high-affinity or high-avidity states via a process of inside-out signaling (Takagi, J., et al. (2002) *Cell* 110, 599). To demonstrate a requirement for T-bet in this process, the attachment of T cells to unstimulated cardiac endothelial cells (ECs) that had been treated with PBS or the CXCR3 ligand, CXCLIO was observed. In this system, all binding is dependent on P-integrin binding to VCAM-1 (Lim, Y. C. et al. (2003) *Am J Pathol* 162, 1591-1601). In the absence of CXCLIO, the binding of WT and T-bet""" CD4+ T cells was identical. In contrast, after the addition of CXCLIO, only WT, and not T-bet$^{-/-}$ T cells, showed increased attachment to ECs under conditions of physiological shear flow.

Murine and human autoimmune diseases are characterized by infiltration of effector T cells to pathological sites. T-bet deficient mice are resistant to a wide range of autoimmune diseases including Type I diabetes, inflammatory colitis and arthritis, lupus nephritis, and experimental autoimmune encephalomyelitis in vivo but the mechanisms responsible have not been firmly established (Lugo-Villarino, G., et al. (2003) *Proc. Natl. Acad. Sci. U.S.A* 100, 7749-7754; Neurath, M. F. et al. (2002) *J. Exp. Med.* 195, 1129; Juedes, A. E., et al. (2004) *J. Exp. Med* 199, 1153-1162; Bettelli, B. et al. (2004) *J Exp. Med* 200, 79-87) it is certainly possible that impaired cellular effector function contributes to such resistance. However, the common finding in all of the above models is a lack of cellular infiltration to inflammatory sites in the absence of T-bet, prompting interest in the trafficking ability of Th1 cells. If migration of effector cells is defective, then, to a certain extent, the competence of effector function becomes relatively less important. This is illustrated by considering the immunosuppressive capacity of the drug FTY720 (Matloubian, M. et al. (2004) *Nature* 427, 355-360), which prevents lymphocyte egress from lymph nodes by targeting sphingosine-1-phosphate and thus impairs T cell trafficking. As demonstrated herein, in the absence of T-bet, primary CD4+ T cells generated under Th1-polarising conditions fail to migrate appropriately in vivo due to defects in multiple specific mechanisms in the T cell trafficking pathway, including sulfation dependent P-selectin binding and CXCR3-dependent arrest and migration.

Of considerable interest with respect to selectin binding is the specificity of a P-selectin defect with preservation of E-selectin binding. It can therefore be inferred that certain STAT4-dependent processes are functionally preserved. It is also noteworthy that there was minimal, if any, binding of T cells activated under Th2 polarising conditions either in the absence or presence of T-bet. Hence, some aspects of Th1 cell development are conserved (binding to E-selectin) excluding the notion that these cells are simply default Th2 cells, since Th2 cells do not bind E-selectin. T-bet appears to control the functional expression of TPST-2 and, possibly, TPST-1. Little is known about the control of these two critical enzymes but as the reduction in mRNA was not absolute, the mechanism of T-bet control of tyrosine sulfation is not at the transcriptional level. However, the expression and cellular location of these enzymes is exquisitely controlled. Active TPSTs in the Golgi do, to a large degree, themselves require tyrosine sulfation in order to function effectively (Moore, K. L. (2003) *J. Biol. Chem.* 278, 24243-24246) and it remains a possibility that T-bet somehow modulates the post-translational functioning of either of these enzymes, more likely TPST-2 (see below). Furthermore, the relative contribution of these two enzymes to the sulfation of PSGL-1 has not been determined and will require further characterization of mice deficient in one or both of these enzymes. Murine PSGL-1 differs from its human counterpart in certain respects, most pertinently that sulfation of only one of two tyrosine residues is required in mouse, compared to two out of three tyrosine residues in human (Liu, W. et al. (1998). *J. Biol. Chem.* 273, 7078-7087; Ramachandran, V. et al. (1999) *Proc Natl Acad Sci USA* 96, 13771-13776; Xia, L. et al. (2003) *Blood* 101, 552-559). Hence, any deficiency in sulfation might be magnified in human T-cells. Nevertheless, interruption in the function of either of these two enzymes represents an intriguing therapeutic strategy.

The data disclosed herein concerning expression and functioning of chemokine receptors reiterates the hypothesis that selective Th1 trafficking responses are impaired in T-bet$^{-/-}$ mice. Previous studies have elucidated a role for overexpressed T-bet in the induction of surface CXCR3 (Sundrud, M. S. et al. (2003) *J Immunol* 171, 3542-3549; Lametschwandtner, G. et al. (2004) *J Allergy Clin. Immunol* 113, 987-994) on long-term polarized Th2 cells and demonstrated an associated increase in chemotactic function. Furthermore, retroviral transduction of T-bet into polarized Th2 clones induces marked secretion of IFN-γ, the cytokine that has been shown to be key in driving the expression of CXCR3. In the light of the present data, the fact that IFN-γ drives expression of CXCR3 may be reinterpreted as IFN-γ acting upstream of T-bet to increase its expression: T-bet then induces expression of CXCR3. This is the first description that deletion of T-bet leads to a reduction in CXCR3 expression with the subsequent abrogation of multiple functions, including lymphocyte arrest on activated endothelium and chemotaxis. These findings are of particular interest since a recent report has suggested that the mechanism of action of CD4+CD25+ regulatory T cells may act as suppressors via inhibition of IFN-γ and CXCR3 expression in vivo (Sarween, N. et al. (2004) *J Immunol* 173, 2942-2951). This raises the intriguing possibility that one mechanism of action of CD4+CD25+ T cells may be via suppression of T-bet with subsequent reduction in IFN-γ and CXCR3 expression and consequent impaired T cell trafficking to inflamed peripheral tissues. The absolute loss in CXCR3 expression would suggest that it is a direct transcriptional target of T-bet. However, an enrichment of the CXCR3 promoter by the use of chromatin immunoprecipitation using real time PCR primers tiled to include 1 Kb upstream of the transcription start site, has not been detected, although this does not preclude T-bet binding outside of this proximal promoter region. Conversely, expression and chemotactic function of CCR5, the other archetypal Th1 chemokine, is completely unaltered. Intriguingly, tyrosine sulfation of this chemokine receptor has also been described for its effective functioning (Farzan, M. et al. (1999) *Cell* 96, 667-676). It is possible therefore that unimpaired TPST-2 function can modulate effective sulfation of CCR5 but is not sufficient for PSGL-1. Taken together, these results demonstrate that T-bet exerts a level of control of the trafficking of Th1-lymphocytes that was not previously recognized by existing paradigms. Specific migration of T cells is a major determinant of the outcome of an appropriate immune response. The experiments presented herein provide evidence that the Th1-specific transcription factor T-bet imprints a migratory program upon developing T cells to ensure appropriate homing to inflammatory sites in vivo via control of P-selectin ligand post-translational biosynthesis and CXCR3 expression and function. This finding has significant implications for the design of rational treatments for autoimmune, neoplastic and infectious diseases, and the prevention of rejection of transplanted organs.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. A method for identifying a compound which modulates stable adherence of a T cell to a vascular endothelial cell, comprising:
   a) contacting a T cell with a test compound;
   b) assaying for modulation of a biological activity of T-bet in the presence of said test compound, wherein a decrease in a biological activity of T-bet by the compound identifies the test compound as a compound that inhibits stable adherence of a T cell to a vascular endothelial cell, and an increase in a biological activity of T-bet by the compound identifies the test compound as a compound that enhances stable adherence of a T cell to a vascular endothelial cell, wherein T-bet binds a consensus T-box site in DNA and induces IFN-γ production in CD4+ cells, and wherein T-bet is encoded by (i) a nucleic acid molecule which hybridizes to the full length complement of the nucleic acid molecule set forth in SEQ ID NO:1 in 6×SSC at 45° C., followed by one or more washes in 0.2×SSC, 0.1% SDS at 65° C.; or ii) a nucleic acid molecule which hybridizes to the full length complement of the nucleic acid molecule set forth in SEQ ID NO:3 in 6×SSC at 45° C., followed by one or more washes in 0.2×SSC, 0.1% SDS at 65° C.; or iii) a nucleic acid molecule encoding a polypeptide with at least 90% amino acid identity to SEQ ID NO:2; or iv)

a nucleic acid molecule encoding a polypeptide with at least 90% amino acid identity to SEQ ID NO:4.

2. The method of claim 1, wherein T-bet biological activity is measured by measuring the ability of T-bet to modulate the expression of CXCR3.

3. The method of claim 2, wherein the expression of CXCR3 is determined by PCR.

4. The method of claim 3, wherein the expression of CXCR3 is determined by a T cell chemotaxis assay.

5. The method of claim 4, wherein the chemotaxis assay further comprises CXCL11 or CXCL10.

6. The method of claim 1, wherein a biological activity of T-bet is the ability of T-bet to modulate $\beta$-integrin dependent binding of the T cell to VCAM-1 on an endothelial cell.

7. The method of claim 6, wherein the assay further comprises CXCL11 or CXCL10.

8. The method of claim 1, wherein the compound modulates the recruitment of a T cell to a site of inflammation.

9. The method of claim 1, wherein the T cell is a Th1 cell.

* * * * *